(12) United States Patent
Miyake

(10) Patent No.: US 7,285,088 B2
(45) Date of Patent: Oct. 23, 2007

(54) ENDOSCOPE APPARATUS

(75) Inventor: Kiyoshi Miyake, Asaka (JP)

(73) Assignee: Olympus Corporation, Tokyo (JP)

( * ) Notice: Subject to any disclaimer, the term of this patent is extended or adjusted under 35 U.S.C. 154(b) by 522 days.

(21) Appl. No.: 10/842,806

(22) Filed: May 11, 2004

(65) Prior Publication Data

US 2005/0054899 A1 Mar. 10, 2005

(30) Foreign Application Priority Data

| May 13, 2003 | (JP) | ............................. | 2003-135021 |
| May 28, 2003 | (JP) | ............................. | 2003-151485 |

(51) Int. Cl.
*A61B 1/00* (2006.01)
*A61B 1/005* (2006.01)

(52) U.S. Cl. ...................... 600/146; 600/152

(58) Field of Classification Search ................ 600/102, 600/146, 147, 152, 136
See application file for complete search history.

(56) References Cited

U.S. PATENT DOCUMENTS

| 4,593,679 | A | * | 6/1986 | Collins ........................ 600/146 |
| 4,941,454 | A | * | 7/1990 | Wood et al. ................. 600/149 |
| 6,119,913 | A | * | 9/2000 | Adams et al. ............ 227/176.1 |
| 6,371,907 | B1 | * | 4/2002 | Hasegawa et al. .......... 600/146 |
| 7,041,053 | B2 | * | 5/2006 | Miyake ....................... 600/146 |
| 7,060,027 | B2 | * | 6/2006 | Maeda et al. ................ 600/150 |
| 2002/0032365 | A1 | * | 3/2002 | Hasegawa et al. .......... 600/102 |
| 2005/0075538 | A1 | * | 4/2005 | Banik et al. ................. 600/141 |

FOREIGN PATENT DOCUMENTS

| JP | 61-122619 | 6/1986 |
| JP | 05-293076 | 11/1993 |
| JP | 06-105800 | 4/1994 |

* cited by examiner

*Primary Examiner*—John P. Leubecker
(74) *Attorney, Agent, or Firm*—Scully, Scott, Murphy & Presser, P.C.

(57) ABSTRACT

An endoscope apparatus comprises: an endoscope in which a bending section is provided in its elongated insertion section; control wires stretching out of the bending section; a drive unit, which is attached to and removed from the endoscope; a pulling apparatus, which is provided in the endoscope for performing bending operations of the bending section by pulling the control wires; an installation device for installing the pulling apparatus in the drive unit; and a transmission device, which is installed in the drive unit and the pulling apparatus so as to be attached and removed at will, separate from the installation device, for transmitting the driving force from the drive source to the pulling apparatus.

21 Claims, 47 Drawing Sheets

C-C

D-D

ENDOSCOPE APPARATUS

BACKGROUND OF THE INVENTION

1. Field of the Invention

The present invention relates to an endoscope apparatus, which has a bending section at the tip side of the insertion section of the endoscope, and has a pulling apparatus for pulling control wires stretching out of this bending section.

Priority is claimed on Japanese Patent Application No. 2003-135021 filed on May 13, 2003, and Japanese Patent Application No. 2003-151485 filed on May 28, 2003, the contents of which are incorporated herein by reference.

2. Description of Related Art

In recent years, endoscopes have become widely used that can observe internal organs in a body cavity by inserting an elongated insertion section in the body cavity, and can perform a range of medical treatments using medical instruments inserted in a medical instrument channel as required. Furthermore, industrial endoscopes are used for observation, inspection and the like of internal damage and deterioration in boilers, gas-turbine engines, pipes in chemical plants and the like, the bodies of automobile engines, and the like.

For an example of this type of endoscope, there is an electric bending system endoscope, which has a bending section at the tip side of the endoscope insertion section, and bends the bending section by pulling control wires stretching out of the bending section using a motor.

There is a type of electric bending system endoscope that has a drive unit that uses a motor arranged on the processor side (control unit incorporating a camera control unit (hereunder CCU)), and a pulling apparatus for pulling control wires arranged in a connector section of the endoscope, wherein by the connector section being connected with the processor, the driving force of the motor is transmitted to the endoscope side so that the bending section can be bent (for example, refer to Japanese Unexamined Patent Application, First Publication No. H05-293076).

In such an electric bending system endoscope, the transmission of the driving force is performed in a connecting section between the drive unit and the pulling apparatus, which are connected together by fitting together a male body formed from a shaft body, and a female body consisting of a hole.

Furthermore, there is a type of endoscope in which the bending section performs bending operations using control wires, wherein a driving force can be transmitted to an endoscope side power transmission section by connecting the endoscope side power transmission section with the motor arranged in the bending motor control unit, and bending operations of the bending section are performed by controlling the pull of the control wires connected to the endoscope side power transmission section using the transmitted driving force (for example, refer to Japanese Unexamined patent Application, First Publication No. H06-105800).

Moreover, there is a type of endoscope in which the bending section performs bending operations by control wires, wherein there is provided a rotor to which the control wires are connected, and a roller which makes contact with this rotor to transmit the driving force of the motor (for example, refer to Japanese Unexamined Patent Application, First Publication No. S61-122619).

SUMMARY OF THE INVENTION

An endoscope apparatus of the present invention includes: an endoscope in which a bending section capable of being bent is provided in an elongated insertion section thereof; control wires stretching out of the bending section; a drive unit, which has a drive source that generates driving force, and is attached to and removed from the endoscope; a pulling apparatus, which is provided in the endoscope for performing bending operations of the bending section by pulling the control wires using the driving force applied; an installation device for installing the pulling apparatus in the drive unit; and a transmission device, which is installed in the drive unit and the pulling apparatus so as to be attached and removed at will, separate from the installation device, for transmitting the driving force from the drive source to the pulling apparatus.

Furthermore, the endoscope apparatus of the present invention includes: an apparatus body; an endoscope in which a bending section capable of being bent is provided in an elongated insertion section therof, and a connector section is provided on a base end of the insertion section; control wires stretching out of the bending section; a drive unit, which is installed in the apparatus body, has a drive source that generates a driving force, and is attached to and removed from the connector section; a pulling apparatus which is installed in the connector section, for performing bending operations of the bending section by pulling the control wires using the driving force applied; an installation device for installing the connector section in the apparatus body; and a transmission device, which is installed in the drive unit and the pulling apparatus so as to be attached and removed at will, separate from the installation device, for transmitting the driving force from the drive source to the pulling apparatus.

Furthermore, the endoscope apparatus of the present invention includes: an apparatus body; an endoscope in which a bending section capable of being bent is provided in an elongated insertion section thereof, and a connector section is provided on a base end of the insertion section; control wires stretching out of the bending section; a drum section, which is installed in the apparatus body, for winding the insertion section; a drive unit, which is installed in the drum section, has a drive source that generates a driving force, and is attached to and removed from the connector section; a pulling apparatus which is installed in the connector section, for performing bending operations of the bending section by pulling the control wires using the driving force applied; and an installation device for installing the connector section in the drum section.

DETAILED DESCRIPTION OF THE INVENTION

Hereunder are descriptions of embodiments of the present invention with reference to the drawings.

FIRST EMBODIMENT

Figure 1:
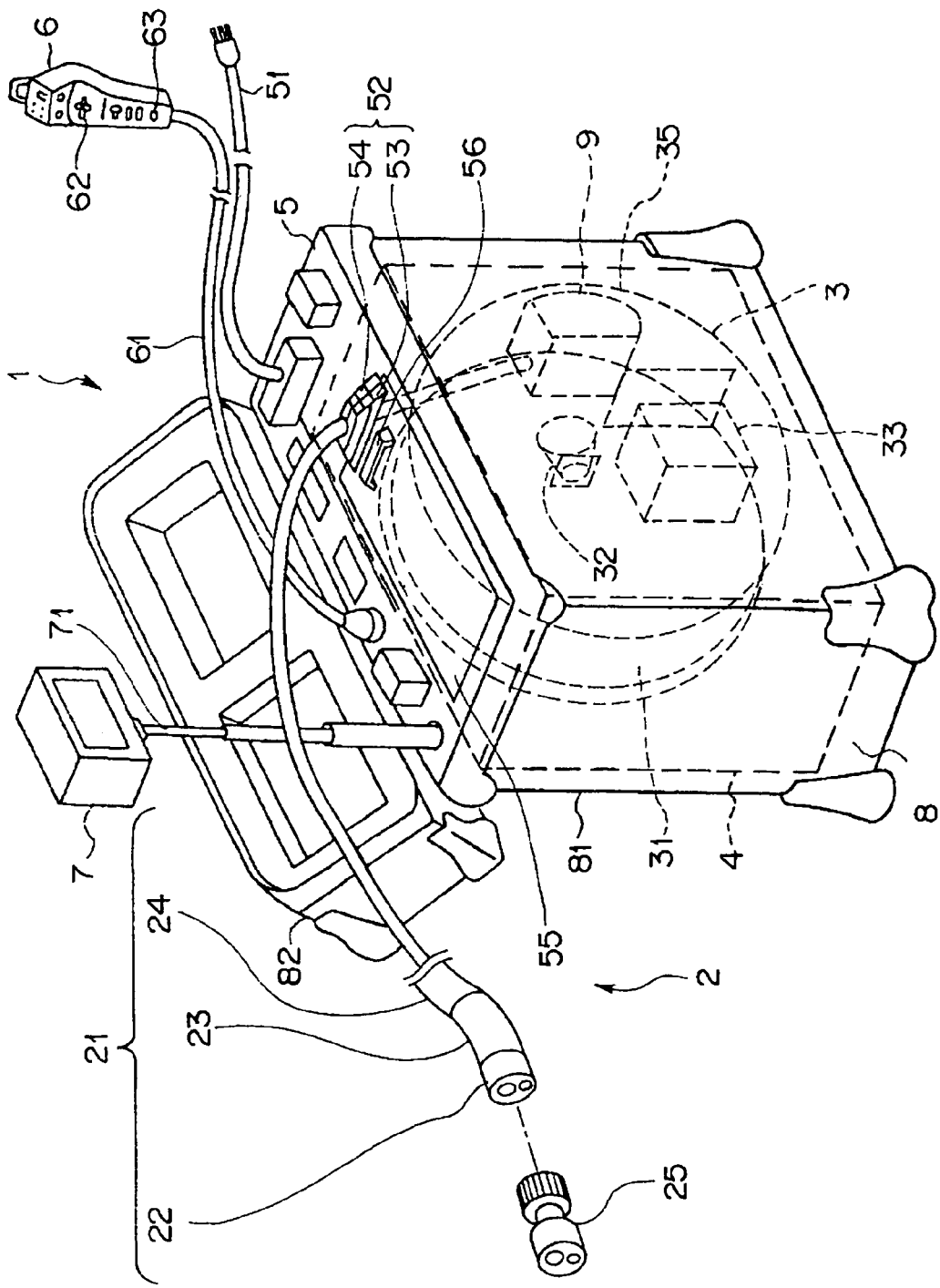
FIG. 1 is a perspective view showing the overall structure of an endoscope apparatus according to a first embodiment of the present invention.
Figure 2:
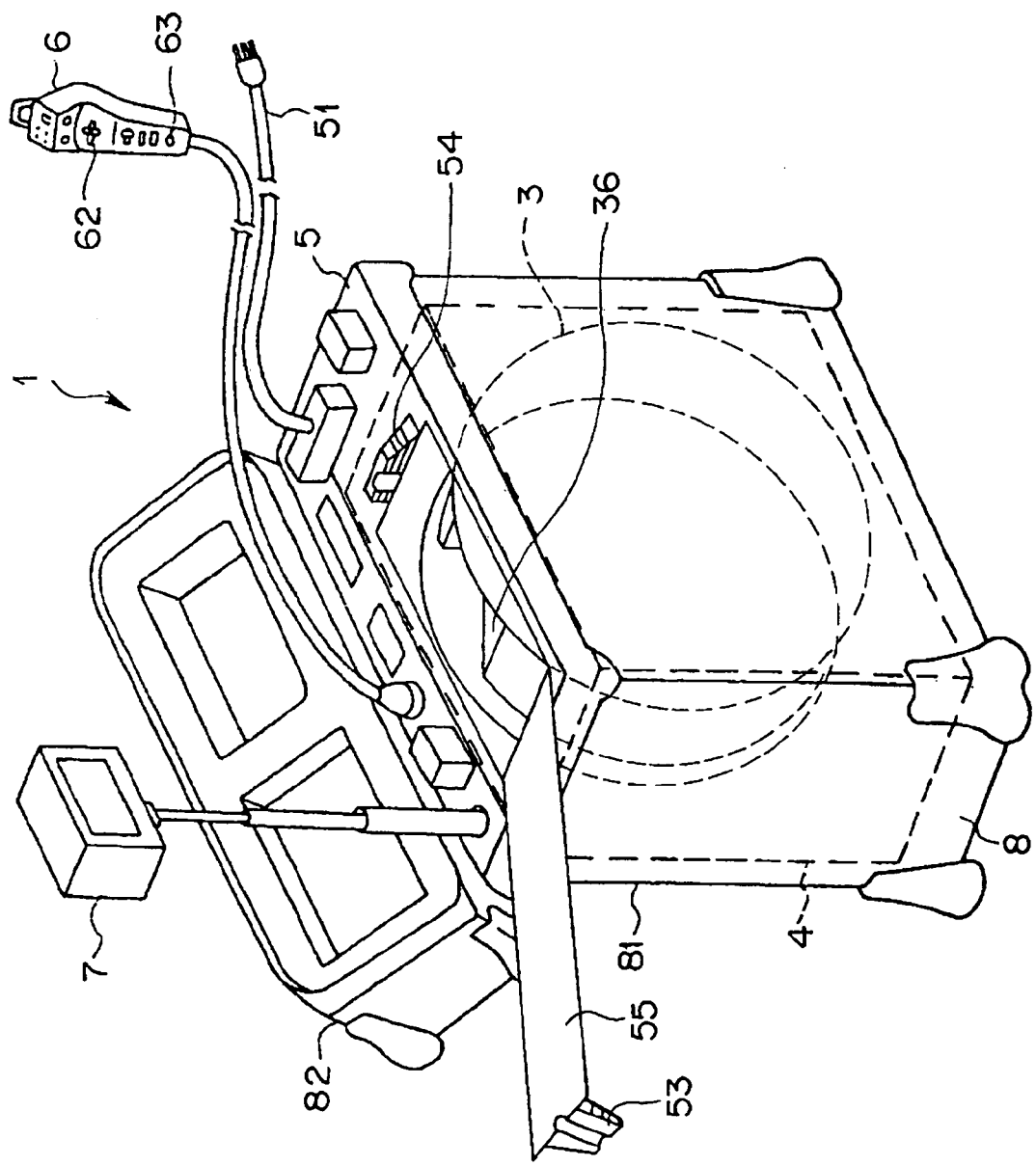
FIG. 2 is a perspective view showing a state in which a cover panel of the endoscope apparatus is opened and the endoscope is removed, according to the first embodiment of the present invention.
Figure 3:
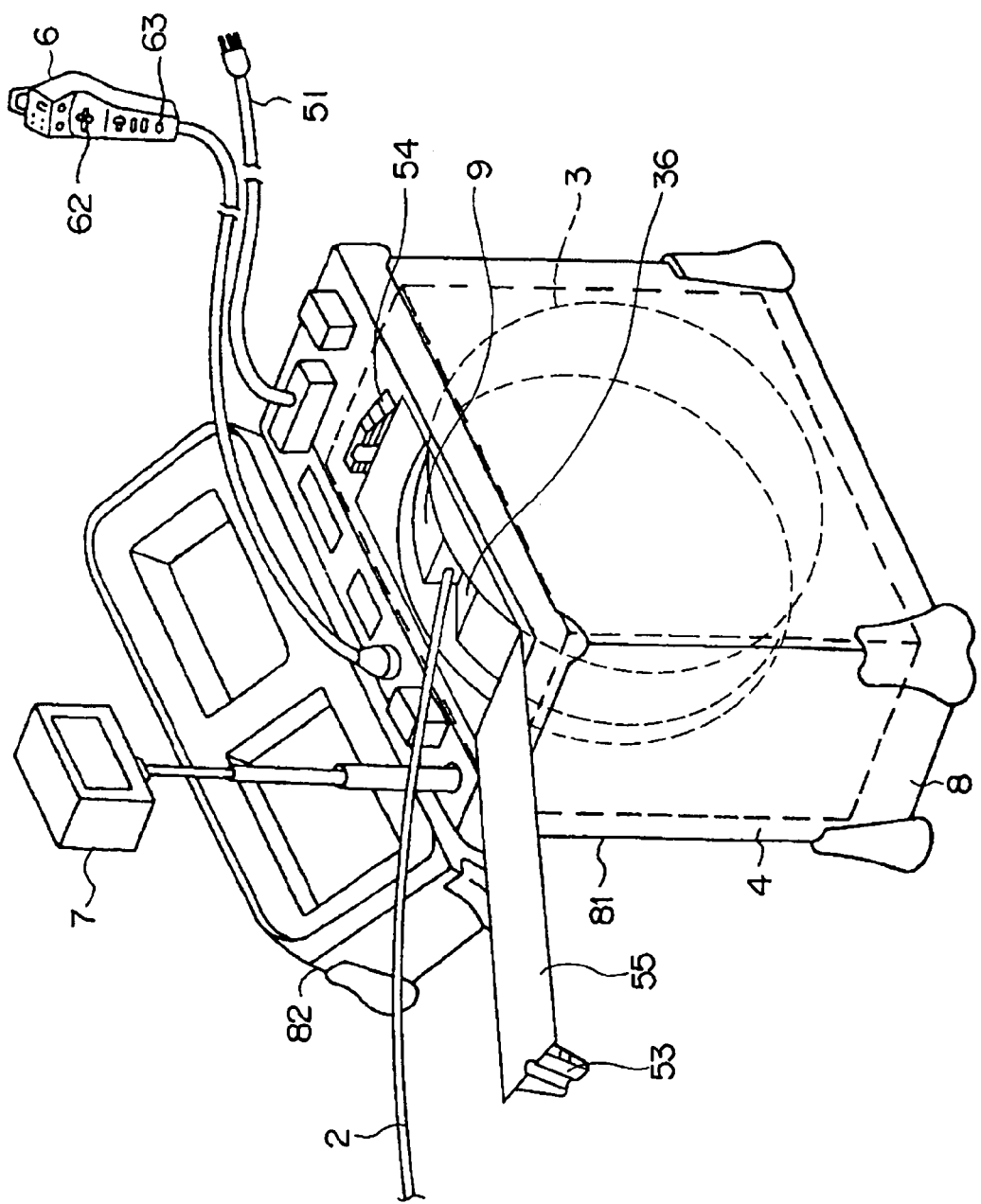
FIG. 3 is a perspective diagram showing a state in which the cover panel of the endoscope apparatus is opened and the endoscope is installed, according to the first embodiment of the present invention.
Figure 4:
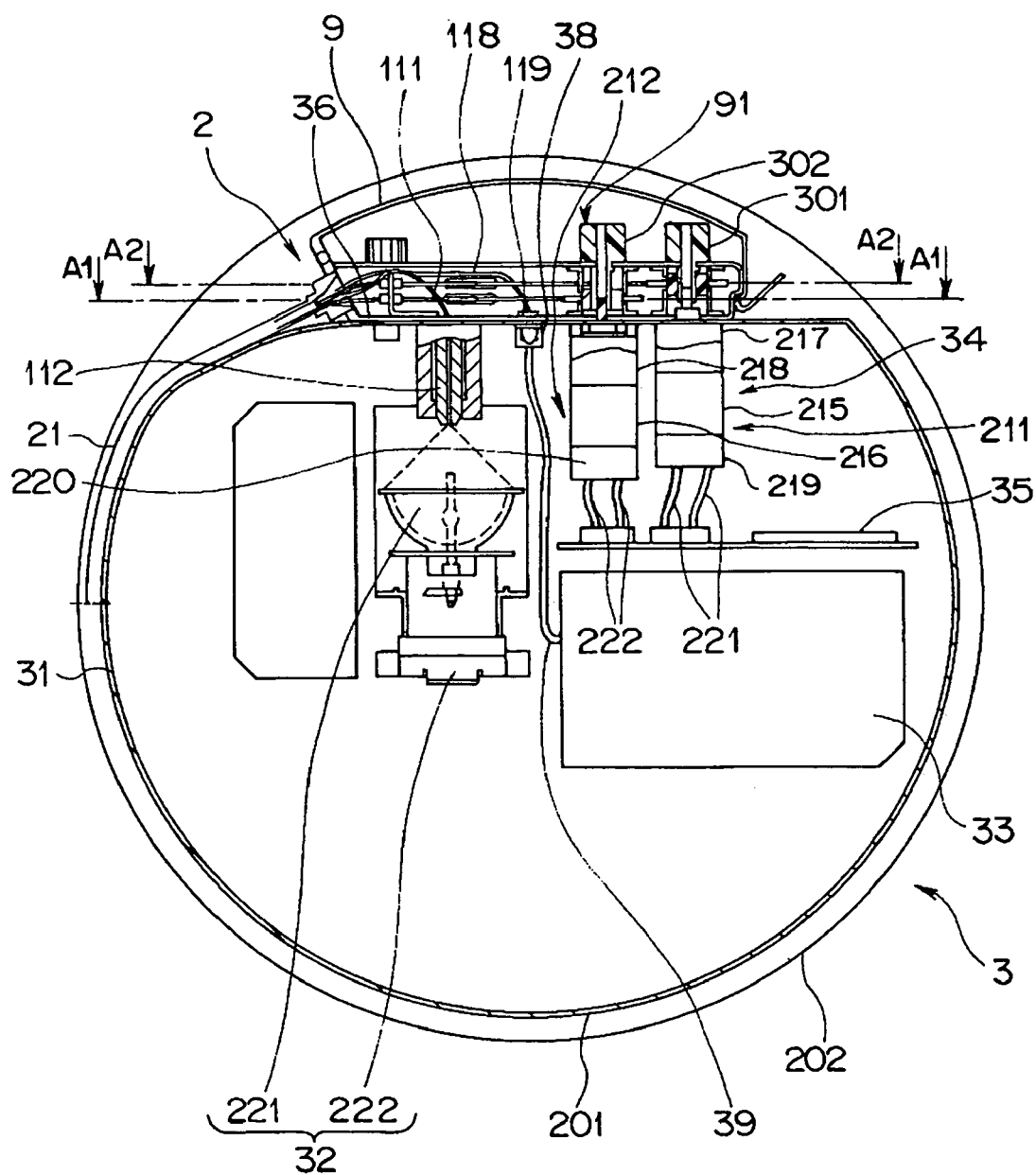
FIG. 4 is a cross-sectional diagram of a drum section according to the first embodiment of the present invention.

FIG. 1 through FIG. 20 are diagrams according to a first embodiment of the present invention. FIG. 1 is a perspective view of the overall structure of an endoscope apparatus. FIG. 2 is a perspective view showing a state in which the cover panel of the endoscope apparatus is opened and the endoscope is removed. FIG. 3 is a perspective diagram showing a state in which the cover panel of the endoscope apparatus is opened and the endoscope is installed. FIG. 4 is a cross-sectional diagram of a drum section.

Figure 5:
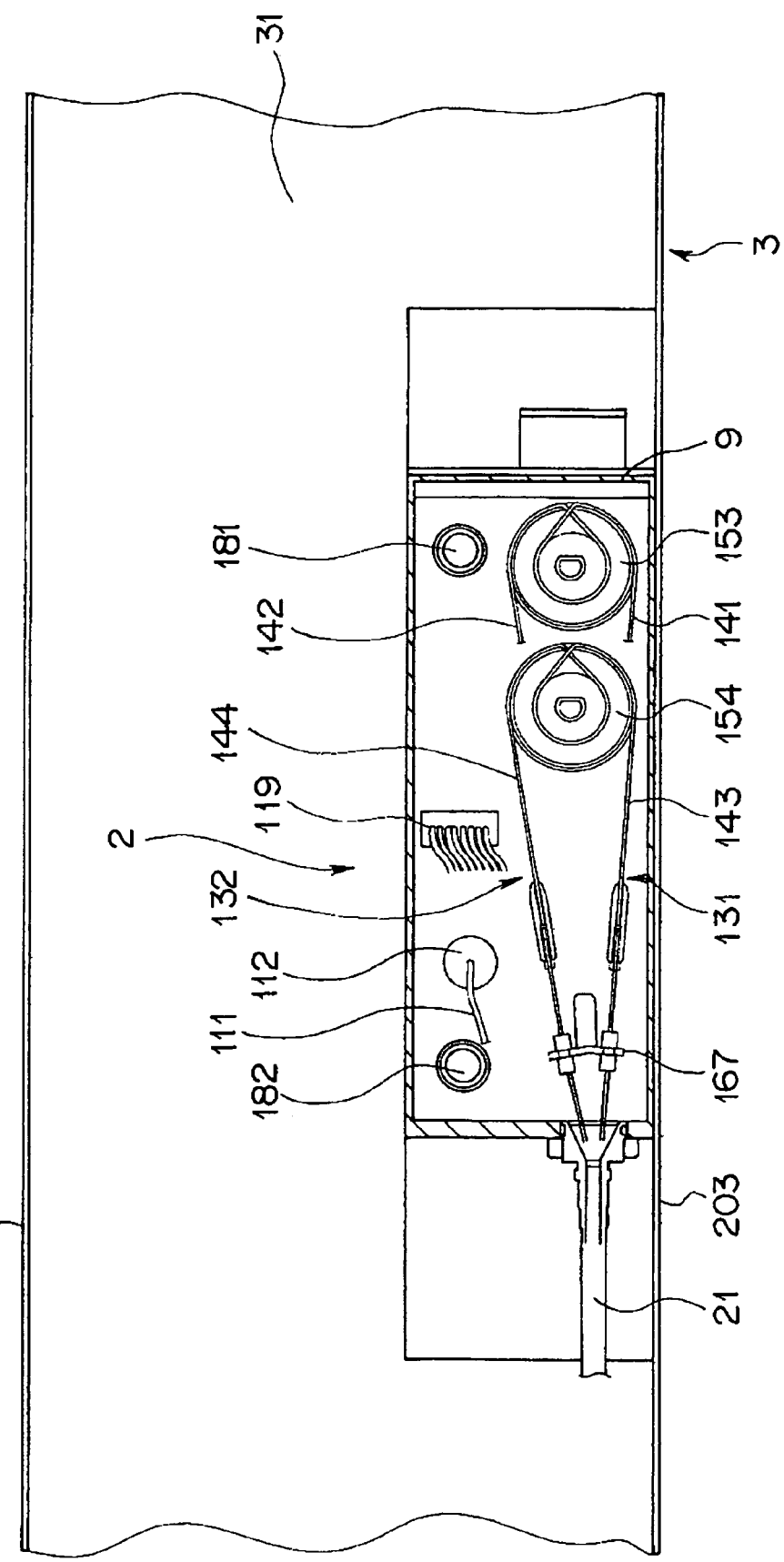
FIG. 5 is an enlarged diagram of a combination of the cross section through line A1-A1 and the cross section through line A2-A2 of FIG. 4, according to the first embodiment of the present invention.
Figure 6:
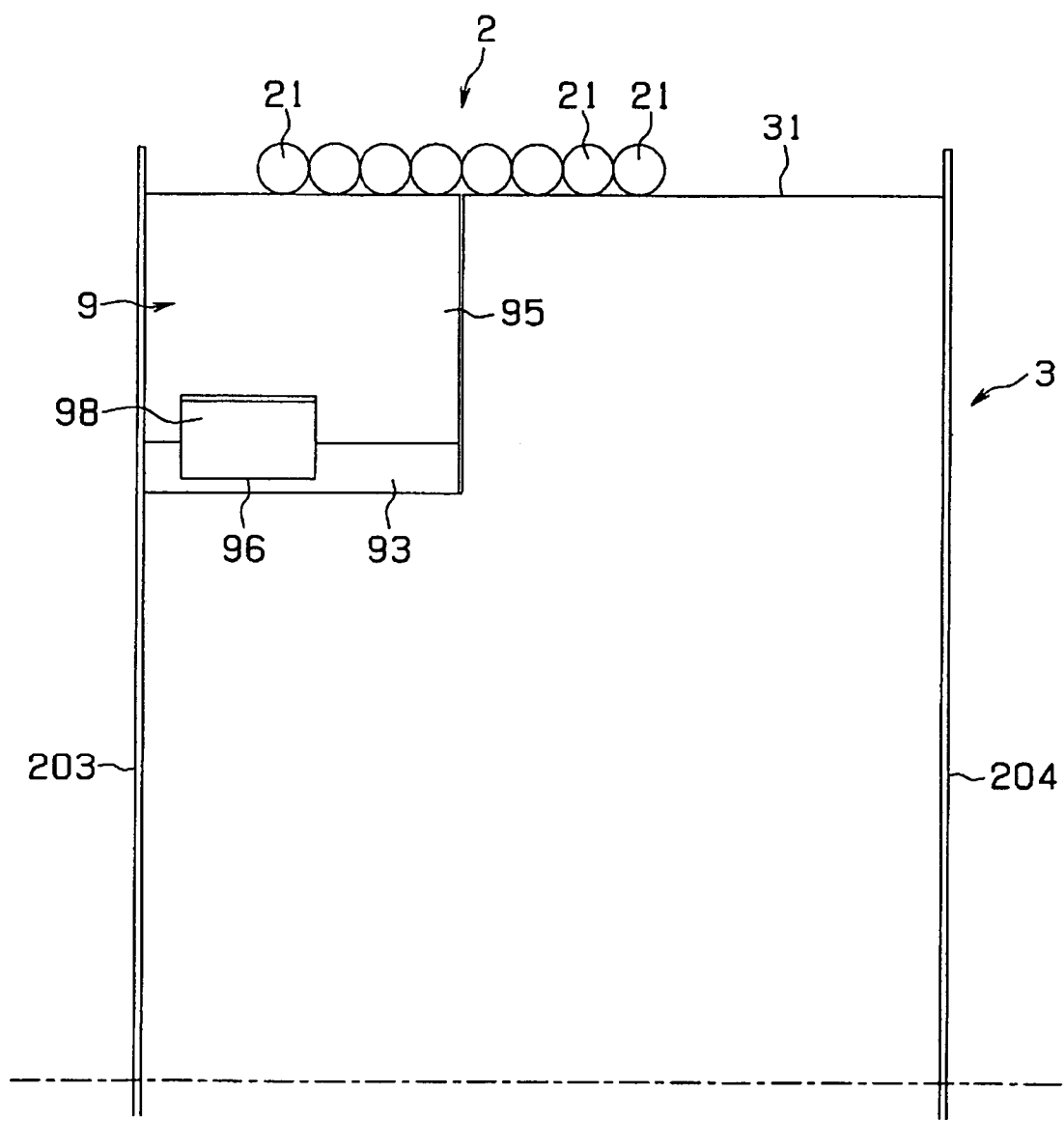
FIG. 6 is a rear view of the drum section according to the first embodiment of the present invention.
Figure 7:
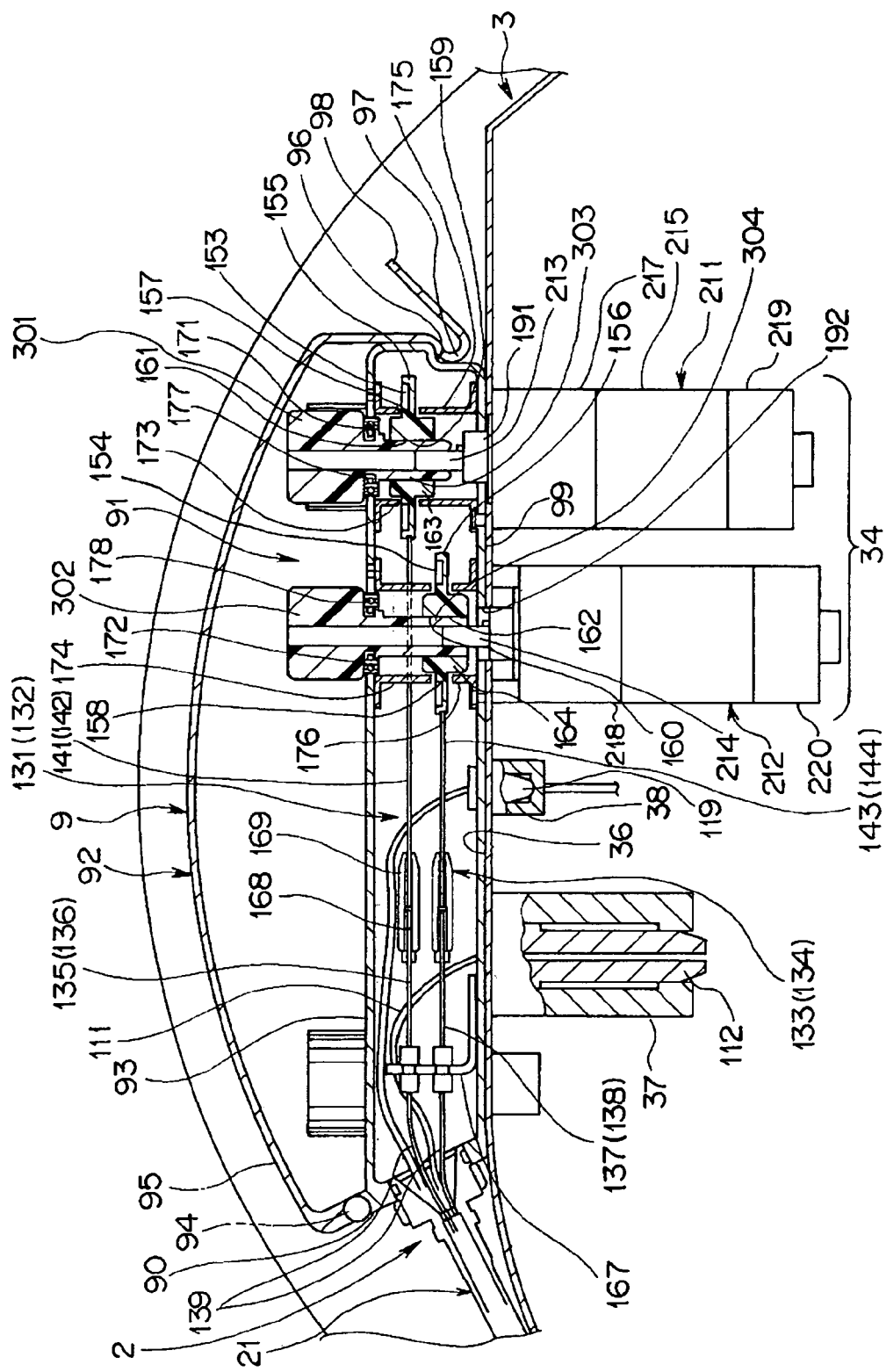
FIG. 7 is an enlarged diagram of a drive unit and a pulling apparatus of FIG. 4, according to the first embodiment of the present invention.

FIG. 5 is an enlarged diagram of a combination of the cross section through line A1-A1 and the cross section through line A2-A2 of FIG. 4. FIG. 6 is a rear view of the drum section. FIG. 7 is an enlarged diagram of a drive unit and a pulling apparatus of FIG. 4.

Figure 8:
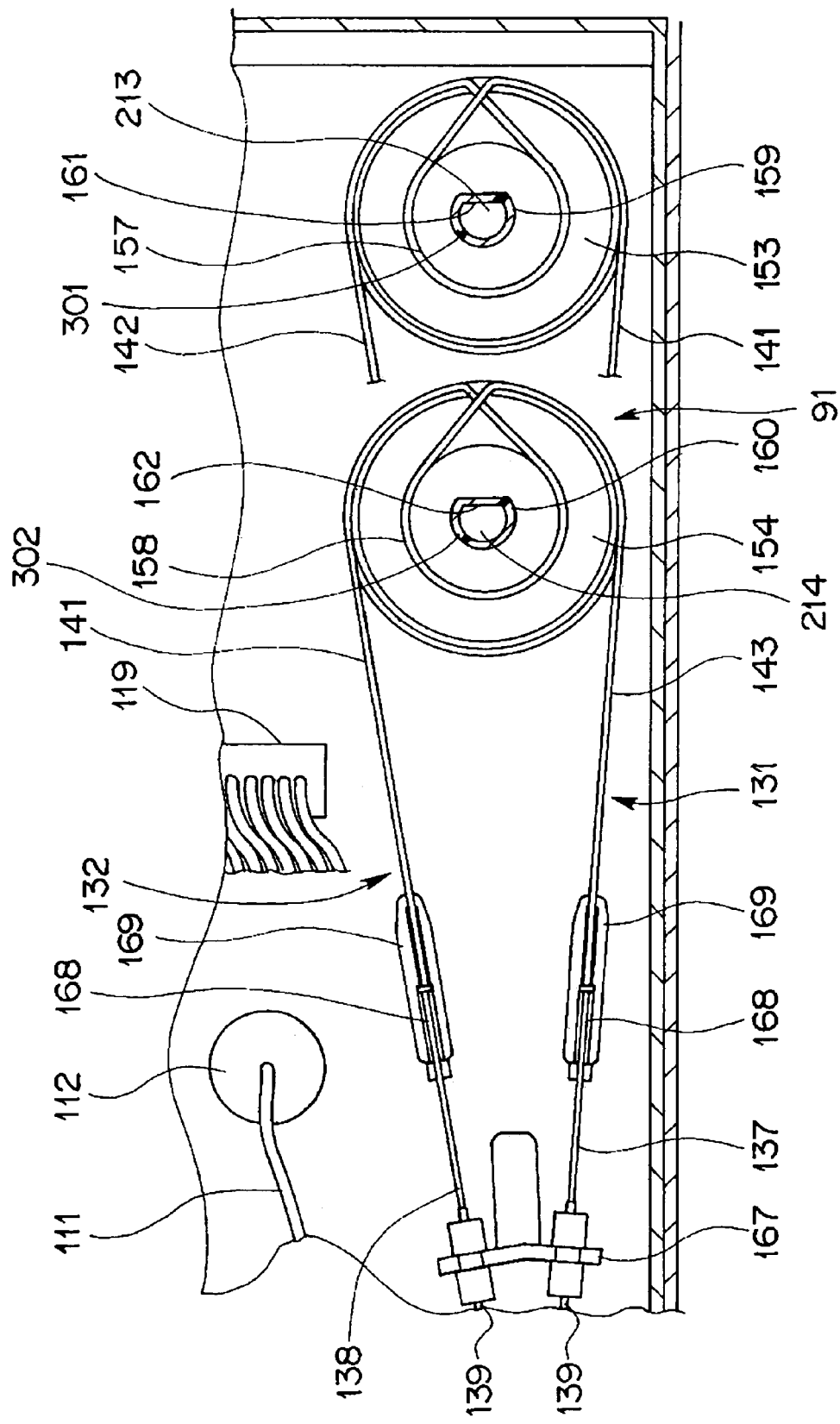
FIG. 8 is an enlarged diagram of the main parts of FIG. 5, according to the first embodiment of the present invention.
Figure 9:
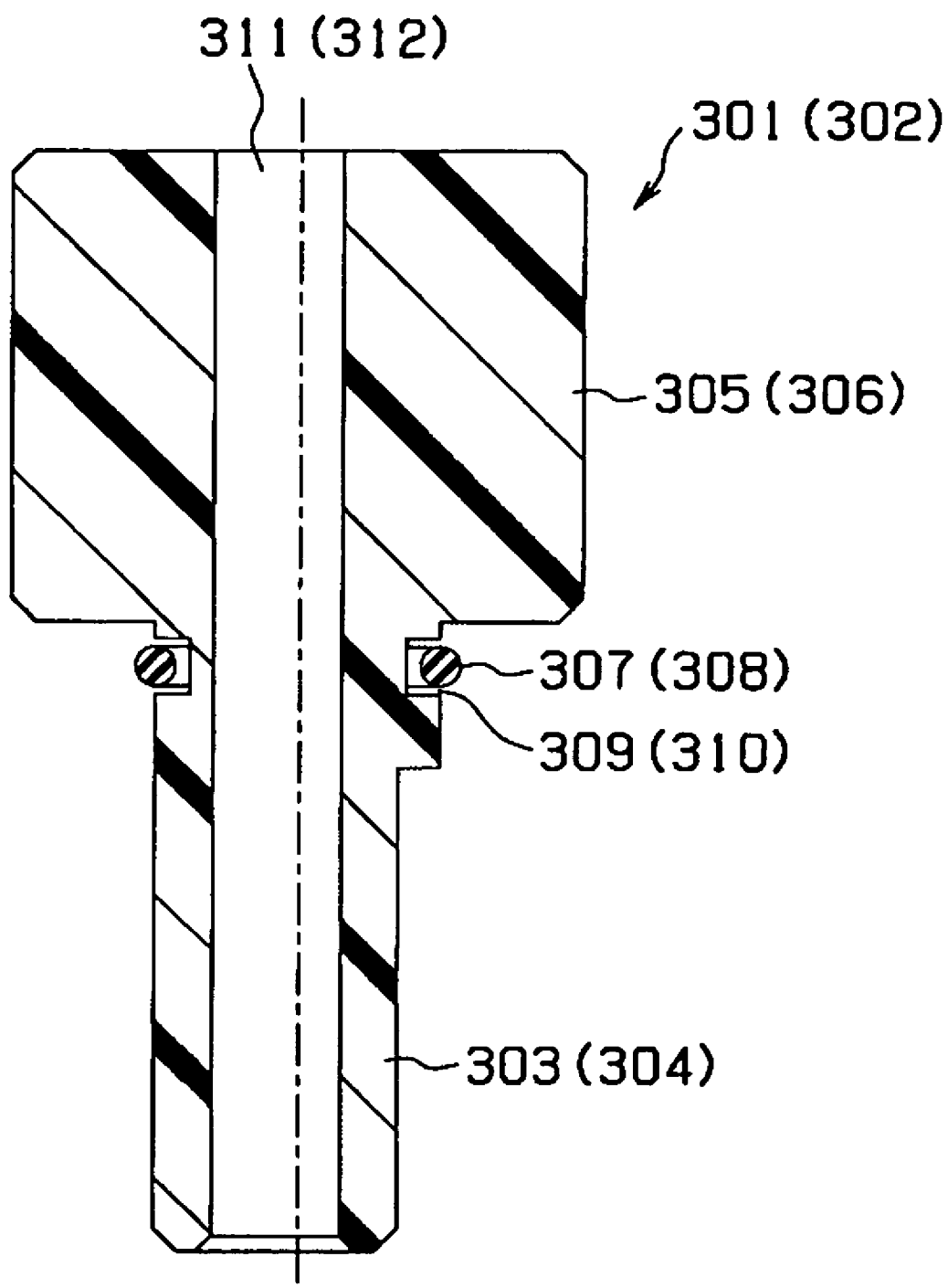
FIG. 9 is an enlarged diagram of a connecting pin, according to the first embodiment of the present invention.
Figure 10:
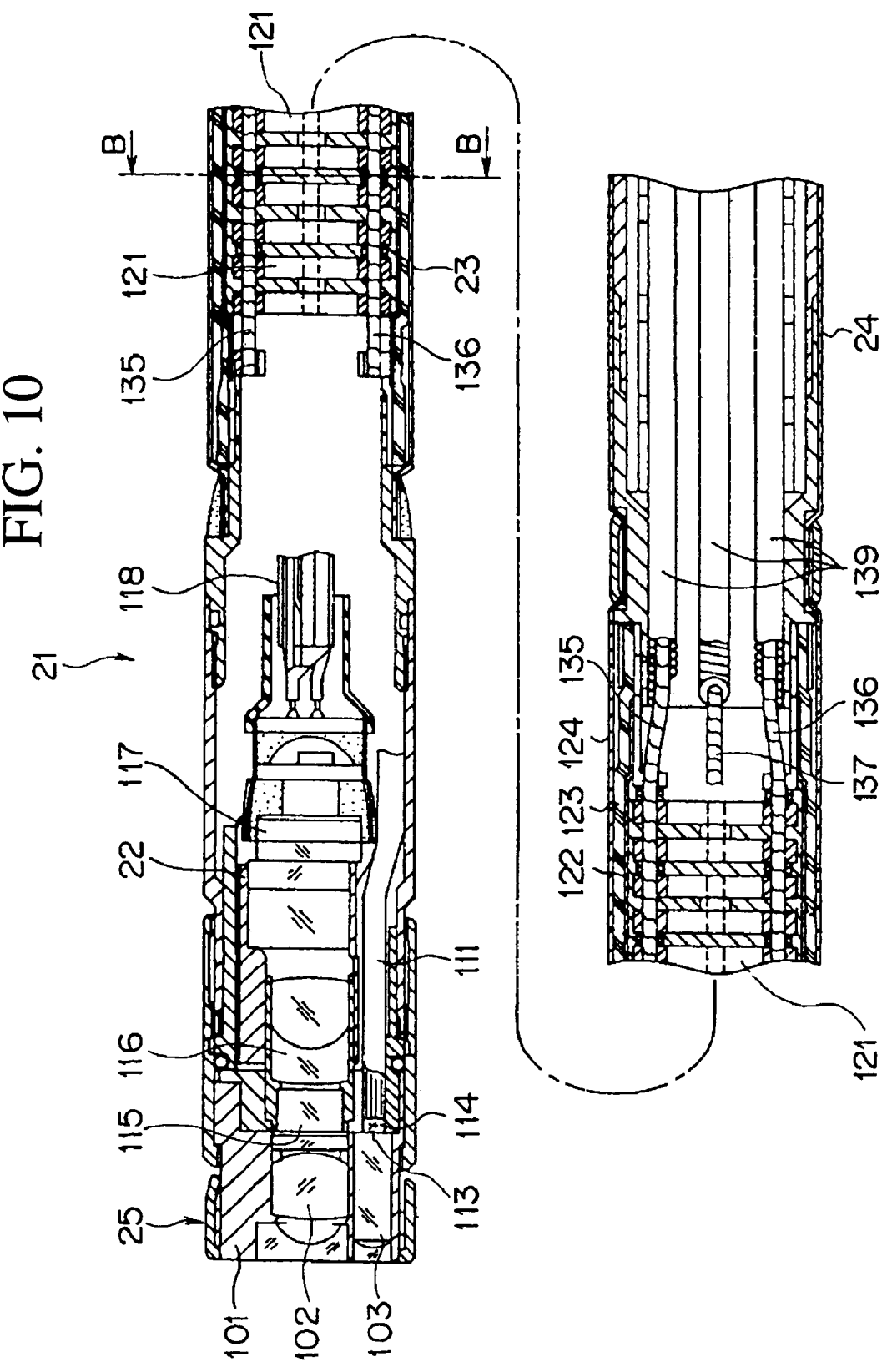
FIG. 10 is a cross-sectional diagram of the insertion section of an endoscope according to the first embodiment of the present invention.
Figure 11:
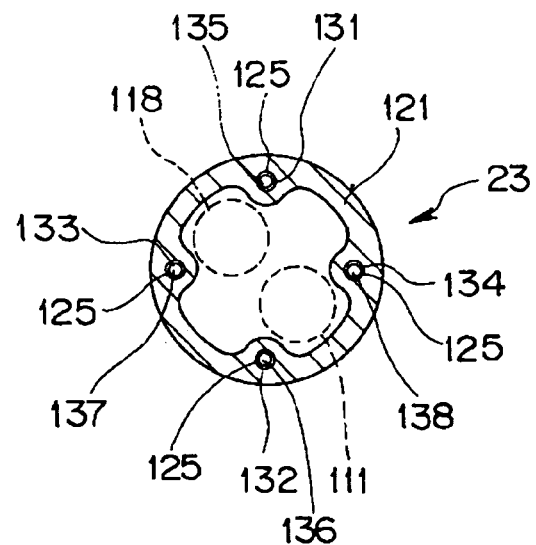
FIG. 11 is a cross-sectional diagram through line B-B of FIG. 10, according to the first embodiment of the present invention.
Figure 12:
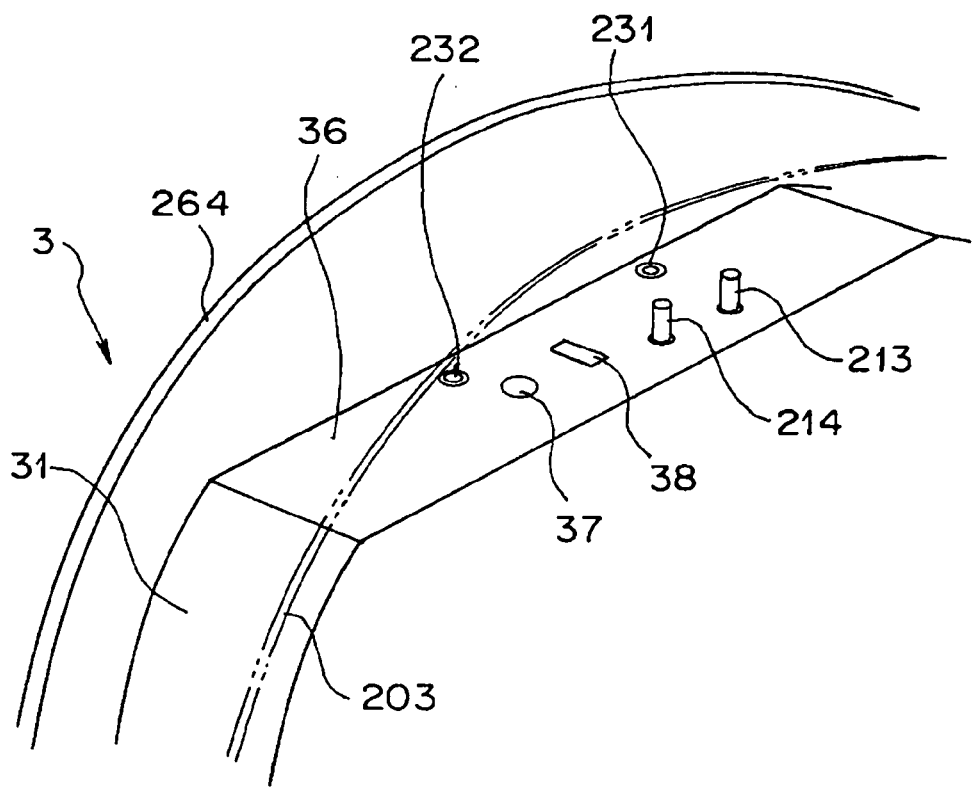
FIG. 12 is a perspective view of a connector installation section according to the first embodiment of the present invention.
Figure 13:
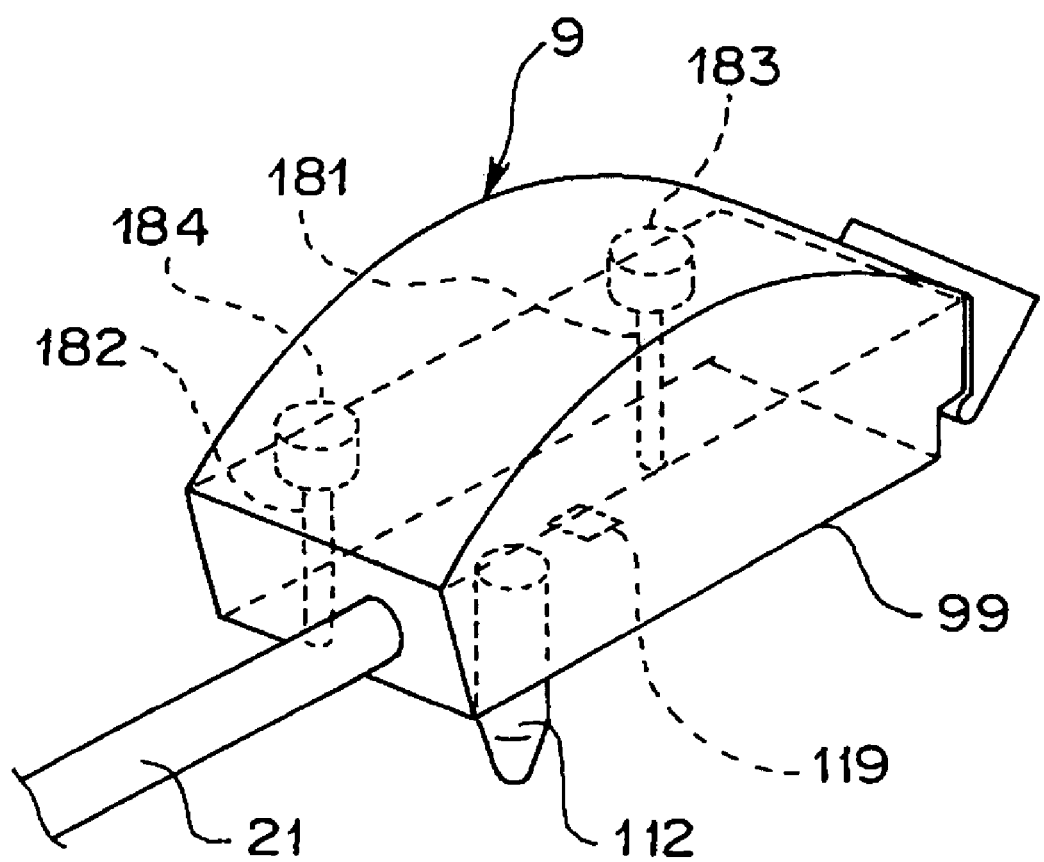
FIG. 13 is a perspective view of a connector section according to the first embodiment of the present invention.
Figure 14:
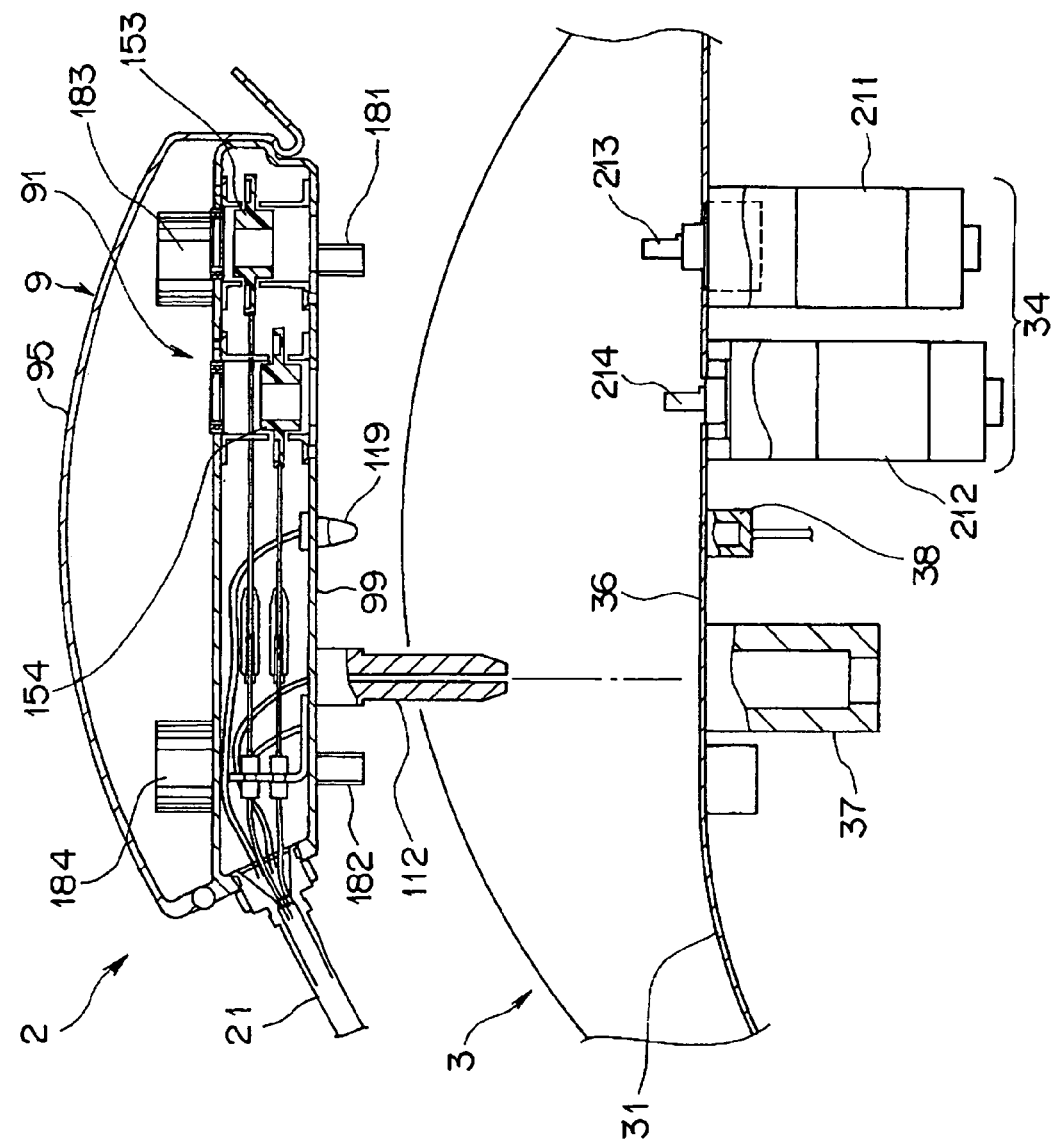
FIG. 14 is a partially enlarged diagram of the main parts in a state before the connector section is installed in the connector installation section, according to the first embodiment of the present invention.
Figure 15:
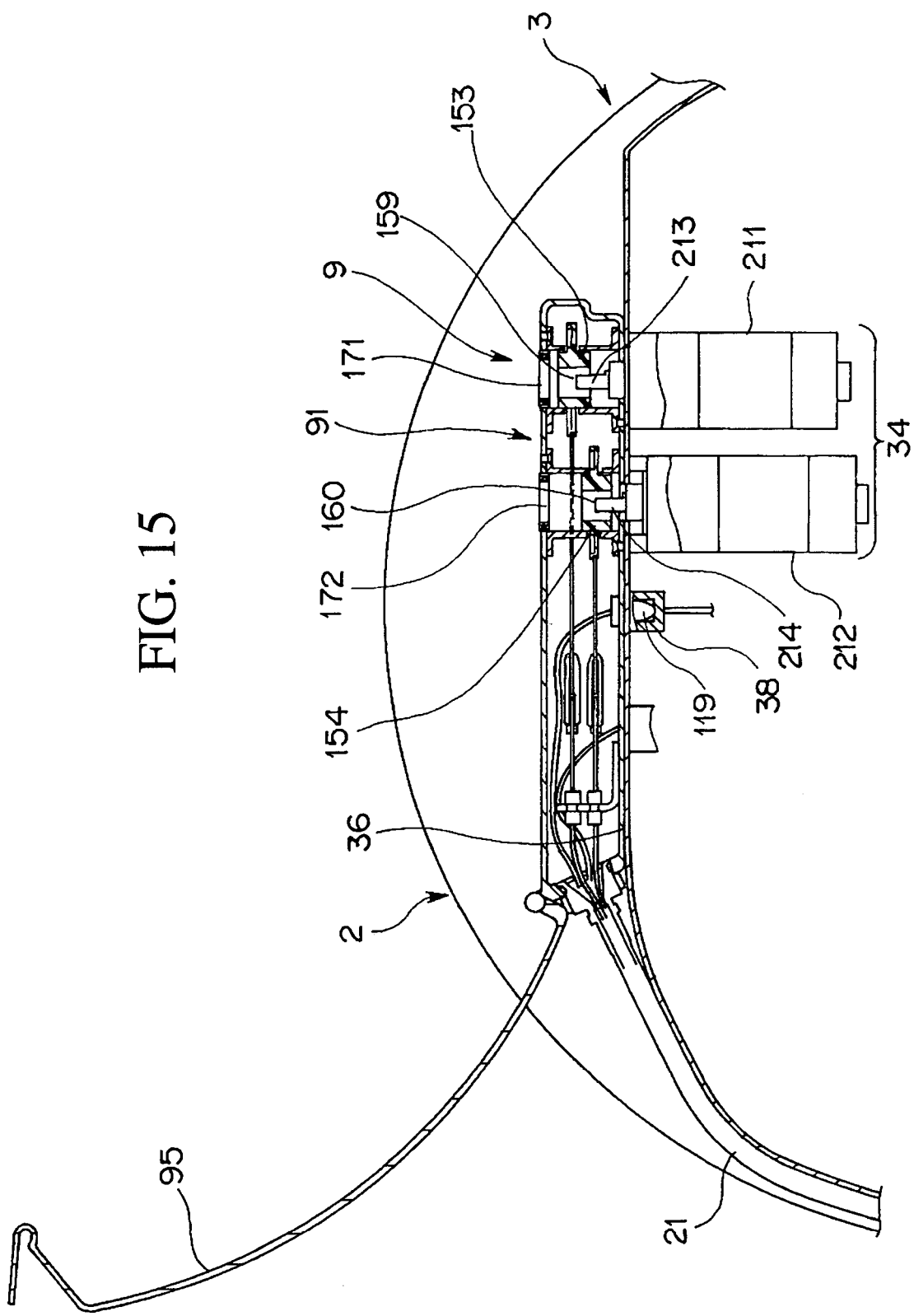
FIG. 15 is a partially enlarged diagram of the main parts in a state in which the connector section is installed in the connector installation section, and the connector case is opened according to the first embodiment of the present invention.
Figure 16:
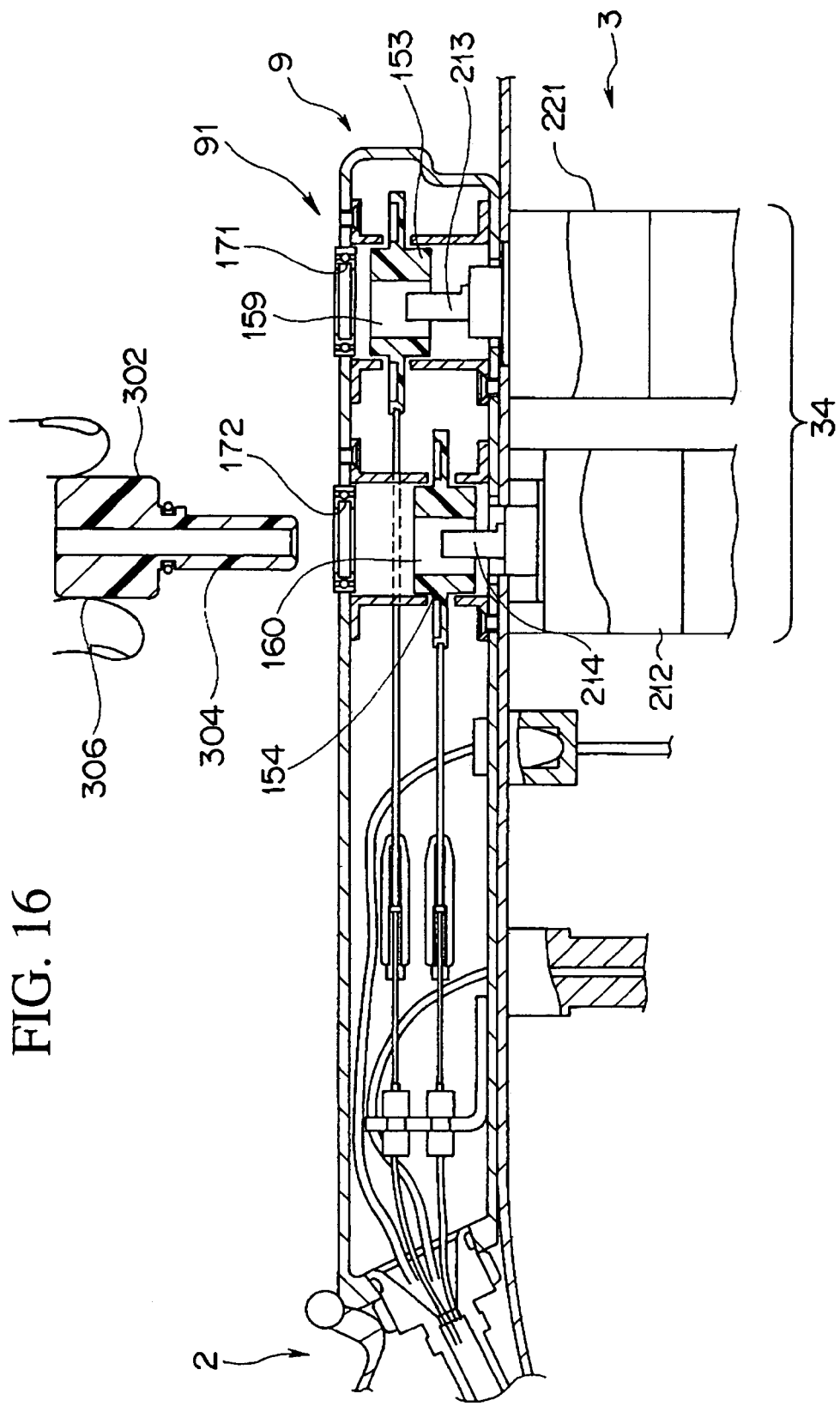
FIG. 16 is a partially enlarged diagram of the main parts in a state before the connecting pin is installed in a pulley section, according to the first embodiment of the present invention.
Figure 17:
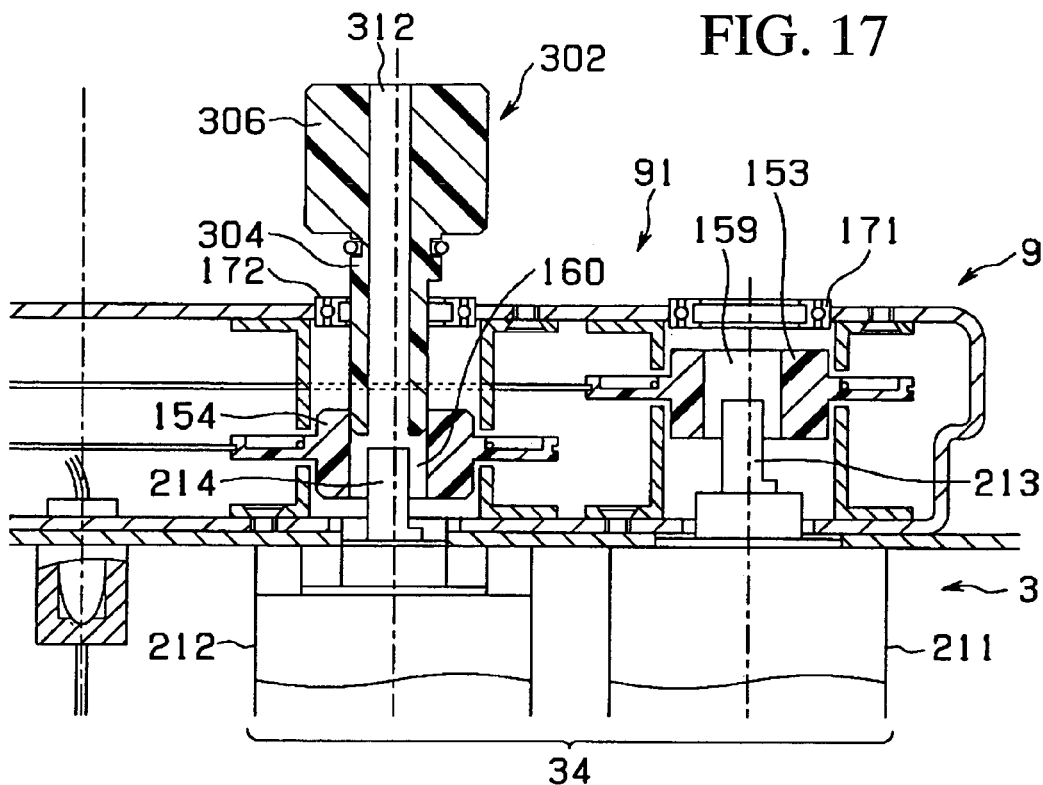
FIG. 17 is an explanatory diagram showing a first state of the operation whereby the link pin is installed in the pulley section, according to the first embodiment of the present invention.
Figure 18:
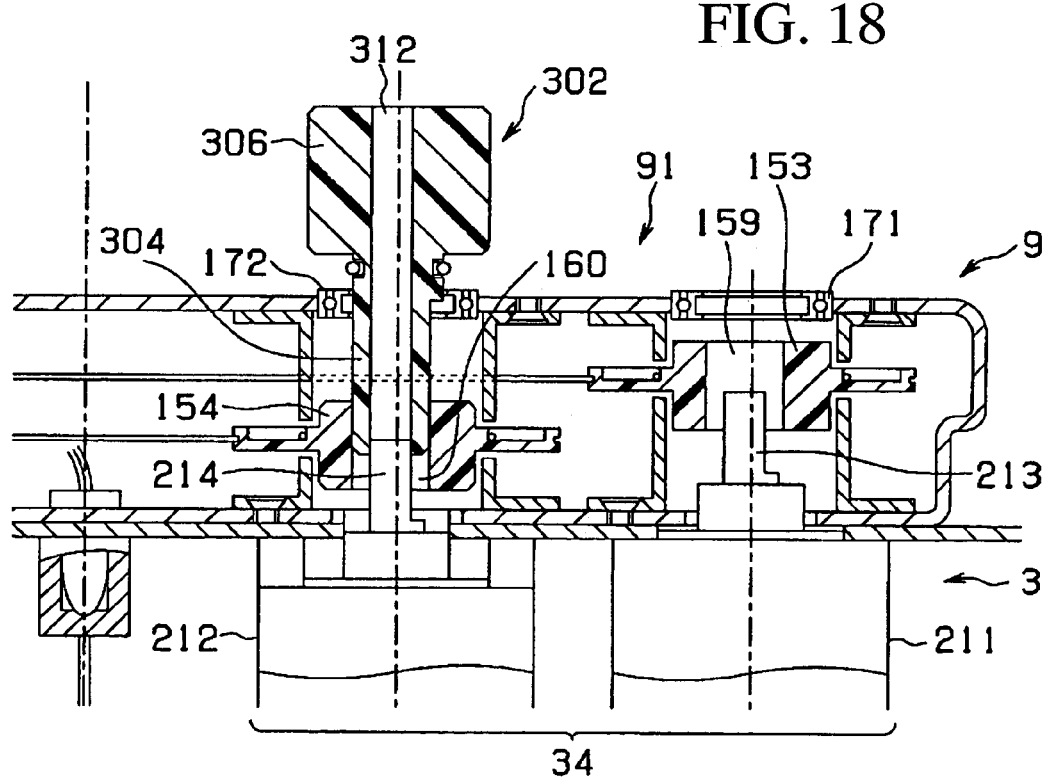
FIG. 18 is an explanatory diagram showing a second state of the operation whereby the connecting pin is installed in the pulley section, according to the first embodiment of the present invention.
Figure 19:
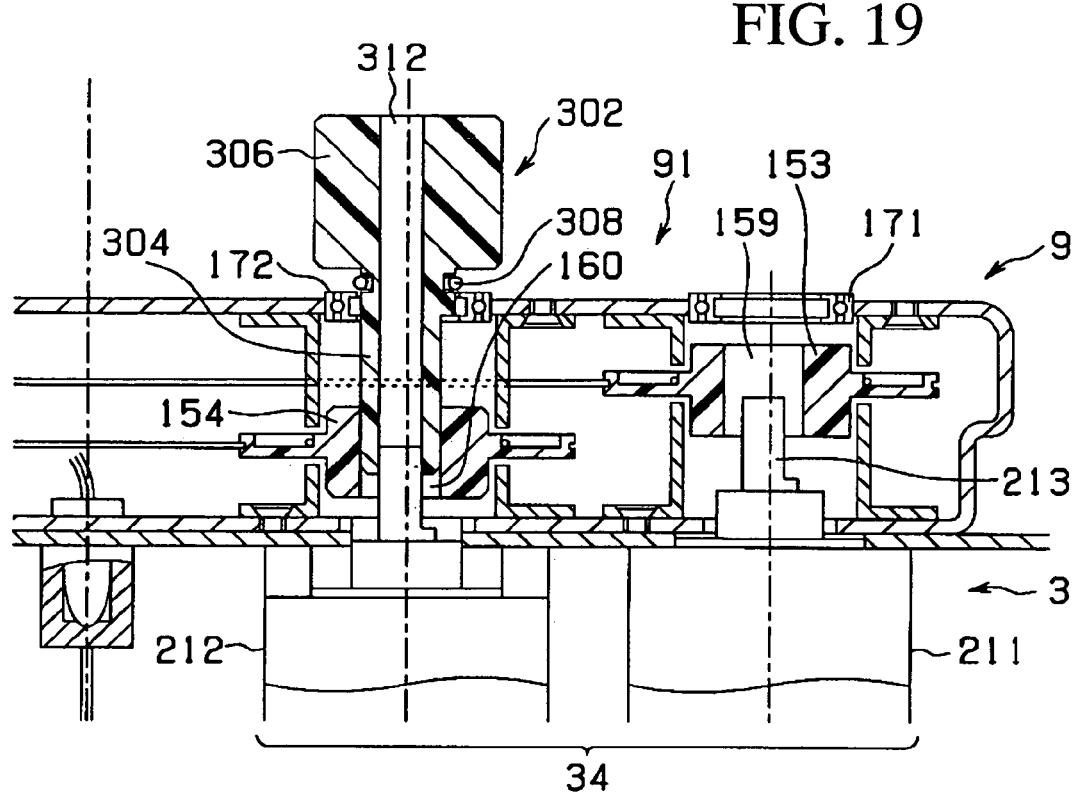
FIG. 19 is an explanatory diagram showing a third state of the operation whereby the connecting pin is installed in the pulley section, according to the first embodiment of the present invention.
Figure 20:
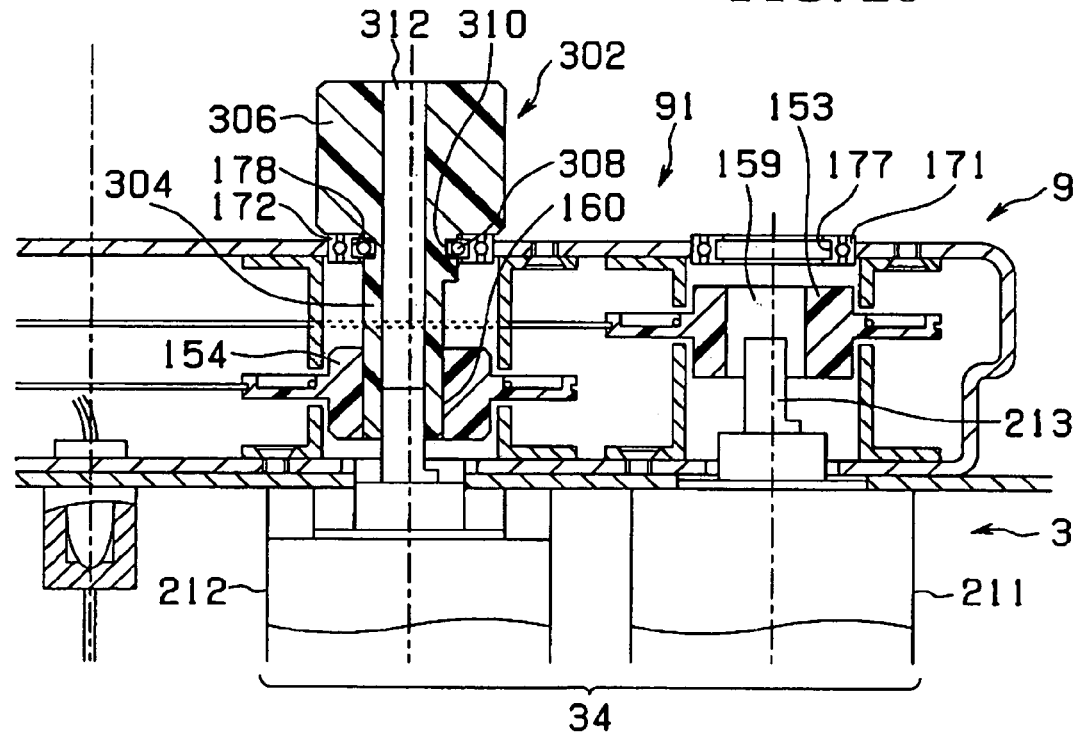
FIG. 20 is an explanatory diagram showing a fourth state of the operation whereby the connecting pin is installed in the pulley section, according to the first embodiment of the present invention.

FIG. 8 is an enlarged diagram of the main parts of FIG. 5. FIG. 9 is an enlarged diagram of a connecting pin. FIG. 10 is a cross-sectional diagram of the insertion section of an endoscope. FIG. 11 is a cross-sectional diagram through line B-B of FIG. 10. FIG. 12 is a perspective view of a connector installation section. FIG. 13 is a perspective view of a connector section. FIG. 14 is a partially enlarged diagram of the main parts in a state before the connector section is installed in the connector installation section. FIG. 15 is a partially enlarged diagram of the main parts in a state in which the connector section is installed in the connector installation section, and the connector case is opened. FIG. 16 is a partially enlarged diagram of the main parts in a state before the connecting pin is installed in a pulley section. FIG. 17 is an explanatory diagram showing a first state of an operation whereby the connecting pin is installed in the pulley section. FIG. 18 is an explanatory diagram showing a second state of the operation whereby the connecting pin is installed in the pulley section. FIG. 19 is an explanatory diagram showing a third state of the operation whereby the connecting pin is installed in the pulley section. FIG. 20 is an explanatory diagram showing a fourth state of the operation whereby the connecting pin is installed in the pulley section.

(Structure)

As shown in FIG. 1, an endoscope apparatus 1 of the present embodiment basically comprises; an industrial endoscope (abbreviated hereunder as endoscope) 2, a drum section 3, a frame section 4, a front panel 5, a remote controller 6, a monitor 7, a storage case 8, and an AC cable 51. The endoscope 2 is provided with a flexible elongated insertion section 21.

The insertion section 21 of the endoscope 2 rolls onto an outer circumference section 31 of the drum section 3.

The frame section 4 holds the drum section 3 such that it can rotate.

The front panel 5, on which a range of switches, connectors, and supply and exhaust ducts is arranged, is provided on top of this frame section 4.

The remote controller 6 is connected to the front panel 5 via a cable 61 such that it can be attached and removed.

The monitor 7 is supported by a telescopic rod 71 such that it can be rotated.

The storage case 8 is provided with a shock absorbing material or the like to absorb any impact force applied to the equipment stored. The storage case 8 comprises a housing 81 forming the case body, and a lid 82.

The AC cable 51 is connected to the front panel 5, which enables mains power to be supplied.

The insertion section 21 of the endoscope 2 extends from the front panel 5 via rubber components 52 to prevent buckling.

This insertion section 21 comprises a tip section body 22, being a rigid body, a bending section 23, and a flexible tube section 24 arranged in line in that order from the tip side. A connector section is arranged in line on the base end side of the insertion section 21.

The bending section 23 is formed such that it can be bent in order to direct the tip section body 22 in a desired direction. The flexible tube section 24 is elongated and is flexible.

A connector section 9 is capable of being attached to and removed from the drum section 3.

The front panel 5 has a cover panel 55 that can be opened and closed, and when it is opened, the drum section 3 can be accessed at will. The components 52 comprise a rubber piece 53 and a rubber piece 54. The rubber piece 53 is provided on the cover panel 55. The rubber piece 54 is provided on the main body of the front panel 5. Furthermore, a handle 56 is provided on the cover panel 55.

Next is a detailed description of the drum section 3 with reference to FIG. 1 and FIG. 4.

As shown in FIG. 4, a light source section 32, a camera control unit (referred to hereunder as CCU) 33, a drive unit 34, an electric bending circuit section 35, and the like, are stored in the internal cavity of the drum section 3.

The optical source section 32 supplies illumination light to a light guide 111, being the illumination transmission device of the endoscope 2.

The CCU 33 performs signal processing for an imager described later, which is provided in the tip section body 22 of the endoscope insertion section 21.

The drive unit 34 generates a driving force to bend the bending section 23 of the endoscope insertion section, and operates a pulling apparatus described later.

The electric bending circuit section 35 comprises a circuit, or the like, which drives the drive unit 34 and controls the bending condition of the bending section 23 based on control instructions from the remote controller 6.

Furthermore, the drum section 3 has a connector installation section 36 for the endoscope 2 in its outer circumference section 31. The connector section 9 incorporates a pulling apparatus 91 as described later.

As shown in FIG. 1, the remote controller 6 is provided with a joystick 62. The joystick 62 is a bending input control section for bending the bending section 23 of the endoscope insertion section 21. Moreover, the remote controller 6 is provided with a power button 63. Furthermore, a range of optical adaptors 25, which alter optical characteristics such as the line of sight, angle of visibility, and the like, can be installed in the tip section body of the endoscope insertion section 21 such that they can be attached and removed at will.

As shown in FIG. 10, the optical adaptor 25 is an adaptor body 101 provided with an adaptor side optical system 102 and an illumination light system 103.

A light guide 111 for transmitting illumination light is inserted in the endoscope insertion section 21.

The base end of this light guide 111 is fixed to a light guide connector 112 as shown in FIG. 4. This light guide connector 112 is assembled onto a light guide connector receiving section 37 in a situation where the connector section 9 is installed in the connector installation section 36. The light guide connector receiving section 37 is connected to the light source section 32 shown in FIG. 4.

As shown in FIG. 10, an illumination window 113 is provided in the tip section body 22. An illumination lens is fixed in the illumination window 113. The tip of the light guide 111 is placed behind the illumination lens 114.

The illumination light supplied from the light source section 32 shown in FIG. 4 is transmitted through the light guide 111, passed through the illumination lens 114 from the tip surface of the light guide 111 shown in FIG. 10, and radiated on a subject such as the inside of a plant and the like via the illumination light system 103 of the optical adaptor 25.

As shown in FIG. 10, an observation window (image pickup window) 115 is provided adjacent to the illumination window 113. An objective optical system 116 is installed in this observation window 115. A charge coupled device type solid-state image sensor (abbreviated to CCD), for example, is arranged in the imaging position of this objective optical system 116 as a solid-state image sensor.

A signal line 118 extending from the CCD 117 is connected to a male image connector 119 installed in the connector section 9. A female image connector 38 to be connected with the male image connector 119 is provided in the drum section 3. This female image connector 38 is connected to the CCU 33 in the drum section 3 via a cable 39. The CCU 33 generates a standard video signal from the signal photoelectrically converted by the CCD 117 shown in FIG. 10, and outputs it to the monitor 7 shown in FIG. 1. In this manner, an endoscope image, being a subject image, is displayed on the screen of the monitor 7.

The bending section 23 is constructed such that a plurality of annular joint wheels 121, connected such that they can turn in the optical axis direction, is covered by a mesh tube 122 and a tube body 123 as shown in FIG. 10 and FIG. 11. The joint wheels 121 at the tip are fixed at the rear part of the tip section body 22.

The light guide 111 and the signal line 118 are arranged in the bending section 23 such that they shift vertically or slightly in the horizontal direction for a vertical bending direction as shown in FIG. 11. Here, vertical bending direction and horizontal bending direction refer to the directions in which the bending section 23 is bent against the lengthwise direction of the insertion section 21. The vertical bending direction and horizontal bending direction are the directions of movement in the two perpendicular planes containing the length direction of the insertion section 21 in a stretched state, and are designated the vertical direction and horizontal direction for convenience. Here, the outside of the tube body 123 shown in FIG. 10 is covered by an outer skin 124 over almost the whole area to the base end of the insertion section 21.

As shown in FIG. 11, holes 125 are formed in locations corresponding to the top, bottom, left and right of the surface of the internal circumference, and divide the internal circumference of the annular section of the joint wheels 121 into four. Insertion section side wires 135, 136, 137 and 138 of bending control wires 131, 132, 133 and 134, being angle wires, are inserted through the holes 125.

The tip sections of the insertion section side wires 135, 136, 137 and 138 are fixed in locations corresponding to the top, bottom, left and right directions respectively of the joint wheel 121 at the tip. Therefore, the bending section 23 is bent in a desired direction by the insertion section side wires 135, 136, 137 and 138 corresponding to each direction being pulled or relaxed; thus the tip section body 22 is directed in a desired direction.

The insertion section side wires 135, 136, 137 and 138 are guided to the base end of the insertion section 21 by guide tubes 139 made of metal, usually stainless steel or the like, as shown in FIG. 10.

Here, the insertion section side wires 135 and 136 are connected to the pulling apparatus side wires 141 and 142 in the connector section 9 as shown in FIG. 7. The pulling apparatus side wires 141 and 142 are connected to each other, and correspond to the two ends of one wire.

The insertion section side wires 137 and 138 are similarly connected to the other pulling apparatus side wires 143 and 144 in the connector section 9. The pulling apparatus side wires 143 and 144 are connected to each other, and correspond to the two ends of one wire. The insertion section side wires 135, 136, 137 and 138, and the pulling apparatus side wires 141, 142, 143 and 144, are designated collectively as the bending control wires 131, 132, 133 and 134 shown in FIG. 11.

As shown in FIG. 4, the drum section 3 comprises a tubular member 201 and a pair of disc members 202.

The tubular member 201 winds the insertion section 21 onto the outer circumference section 31. The pair of disc members 202 enclose the two openings of the tubular member 201.

Here, the disc member 202 which covers the upper side opening in FIG. 4 is the upper plate 203 as shown in FIG. 5 and FIG. 6, and the disc member 202 which covers the lower side opening in FIG. 4 is the lower plate 204 as shown in FIG. 5 and FIG. 6.

As shown in FIG. 6, the drum section 3 winds the insertion section 21 of the endoscope 2 onto the outer circumference section 31 sandwiched between the upper plate 203 and the lower plate 204.

Equipment such as the drive unit 34, the electric bending circuit section 35, the CCU 33, the light source section 32 and the like are built in to the internal cavity of the drum section 3 formed by the tubular member 201, the upper plate 203 and the lower plate 204 as shown in FIG. 4.

The connector section 9 of the base end section of the insertion section 21 is fitted in the connector installation section 36.

The electric bending circuit section 35 shown in FIG. 4 drives motor units 211 and 212 of the drive unit 34, serving as the electric bending apparatuses shown in FIG. 4, based on control instruction signals transmitted from the joystick 62 of the remote controller 6 shown in FIG. 1 in order to bend the bending section 23 shown in FIG. 1 in a desired direction.

Furthermore, as shown in FIG. 4, the light source section 32 comprises a lamp section 221 and a lighting device 222, and supplies illumination light onto the base end surface of the light guide 111.

Here, the drive unit 34, the electric bending circuit section 35, and the light source section 32, are arranged in the drum section 3 as described in FIG. 1, and can be rotated freely with respect to the storage case 8.

Next is a description of the drive unit 34 and the pulling apparatus 91.

Firstly, the pulling apparatus 91 will be described.

As shown in FIG. 4, the connector section 9, which is formed as a housing made of metal or resin, is connected to the base end section of the insertion section 21, and the pulling apparatus 91 is located in this connector section 9.

Since the drive unit 34 and the pulling apparatus 91 bend in both the vertical direction and the horizontal direction, these are a type in which two similar mechanisms are used as a pair. However, in the description, the vertical direction is used as the main example, and since the horizontal direction is similar, its description is omitted to some degree.

As shown in FIG. 7 and FIG. 8, pulley sections 153 and 154, onto which the pulling apparatus side wires 141, 142, 143 and 144 connected to the insertion section side wires 135, 136, 137 and 138 (refer to FIG. 11) are wound, are provided in the pulling apparatus 91.

Furthermore, in the pulley section 153 for vertical bending, the pulling apparatus side wires 141 and 142 are wound into a slot section 155 for winding the pulling apparatus side wires 141 and 142 of this pulley section 153. Parts of the pulling apparatus side wires 141 and 142 are fixed in a stepped section 157 machined in the pulley section 153, by soldering, adhesive, engagement, or the like, so that the pulling apparatus side wires 141 and 142 do not slip out of the pulley section 153.

Similarly, in the pulley section 154 for the horizontal direction, the pulling apparatus side wires 143 and 144 are wound into a slot section 156 for winding the pulling apparatus side wires 143 and 144 of this pulley section 154. Parts of the pulling apparatus side wires 143 and 144 are fixed in a stepped section 158 machined in the pulley section 154, by soldering, adhesive, engagement, or the like, so that the pulling apparatus side wires 143 and 144 do not slip out of the pulley section 154.

D holes 159 and 160, being through holes whose cross sections are D shaped, and which have flat D hole sections 161 and 162, are provided in the pulley sections 153 and 154. The D holes have larger diameters than the output shafts 213 and 214 of the motor units 211 and 212, whose cross sections are similarly D shaped, as described later. Connecting pins 301 and 302 are provided in the connector section 9.

The connecting pins 301 and 302 have connection sections 303 and 304, which engage with the D holes 159 and 160, and also engage with the output shafts 213 and 214.

Here, the connecting pins 301 and 302 have gripping sections 305 and 306 for gripping the connecting pins 301 and 302 as shown in the enlarged diagram of FIG. 9, C rings 307 and 308 which engage bearing parts 171 and 172, and C ring grooves 309 and 310 for holding the C rings 307 and 308, as described later.

Furthermore, the connecting pins 301 and 302 are provided with observation holes 311 and 312 for observing the appearance of the tips of the connecting sections 303 and 304.

Moreover, the pulley sections 153 and 154 have hubs 163 and 164 whose central parts protrude.

Top and bottom support sleeves 173 and 175 which rotationally support the hub 163, for positioning the pulley section 153, are arranged on both sides of the hub 163 in the pulling apparatus 91. Top and bottom support sleeves 174 and 176 which rotationally support the hub 164, for positioning the pulley section 154, are arranged on both sides of the hub 163 in the pulling apparatus 91.

Since the support sleeves 173, 174, 175 and 176 rotationally support the hubs 163 and 164, in a state where there is a certain degree of clearance between the hubs 163 and 164 and the support sleeves 173, 174, 175 and 176, there is some backlash in the pulley sections 153 and 154 due to the clearance around the shaft centers of the hubs 163 and 164.

Furthermore, as shown in FIG. 7 and FIG. 8, the aforementioned guide tubes 139 lead to the connector section 9, and their ends are engaged and retained by an engagement plate 167.

Moreover, the insertion section side wires 135, 136, 137 and 138, and the pulling apparatus side wires 141, 142, 143 and 144, are connected at an intermediate location between the engagement plate 167 and the pulley sections 153 and 154, and the connection is made by a male screw ferrule 168 having a male thread, and a female screw ferrule 169.

The male screw ferrule 168 and the female screw ferrule 169 are provided with a chemical loosening prevention device such as lock paint or the like. However, heat shrink tubes may be provided to cover the male screw ferrule 168 and the female screw ferrule 169.

The pulling apparatus side wires 141, 142, 143 and 144 use thicker wires than those of the insertion section side wires 135, 136, 137 and 138. That is, a thick and flexible wire with high resistance against repeated bending is used for the pulling apparatus side wires 141, 142, 143 and 144.

To be specific, wire with 1×3 or 1×7 strands of about 0.2 to 0.5 mm in diameter is used for the insertion section side wires 135, 136, 137 and 138 of the present embodiment, and wire with 7×7 strands, 3×7 strands, 7×19 strands or the like, whose diameter is larger than the insertion section side wires 135, 136, 137 and 138, is used for the pulling apparatus side wires 141, 142, 143 and 144.

Next is a description of a connector case 92 forming the outer enclosure of the connector section 9.

As shown in FIG. 7, the connector case 92 has a connector case body 93, a hinge section 94, and a curved panel 95.

The curved panel 95 can be opened and closed by the hinge section 94.

The curved panel 95 has a convex engagement section 97. The connector case body 93 is provided with a concave engagement section 96. The convex engagement section 97 can be engaged with the concave engagement section 96.

This convex engagement section 97 is formed by part of the curved panel 95 being bent, and the bent part is the convex engagement section 97. The end of the convex engagement section 97 opens and closes the curved panel 95, and is also a lever 98 for disengaging the concave engagement section 96 and the convex engagement section 97.

Furthermore, the connector case 92 is provided with male screws 181 and 182 as shown in FIG. 13, which screw into threaded holes 231 and 232 provided in the connector installation section 36 as shown in FIG. 12. As shown in FIG. 13, fixing knobs 183 and 184, which turn the male screws 181 and 182, are provided at the ends of the male screws 181 and 182.

As shown in FIG. 7, the pulling apparatus 91 is located in the connector case body 93.

Bearing parts 171 and 172 are provided on the top side of the connector case body 93. The bearing parts 171 and 172, into which the connecting pins 301 and 302 are inserted, support the connecting pins 301 and 302 as they rotate and engage the C rings 307 and 308.

These bearing parts 171 and 172 have engagement grooves 177 and 178 for engaging the C rings 307 and 308.

Furthermore, the base 99 of the connector case body 93 is provided with holes 191 and 192 for inserting output shafts 213 and 214 as described later.

Moreover, the base 99 is provided with a light guide connector 112, and a male image connector 119, which are to be connected respectively with the light guide connector receiving section 37 and the female image connector 38 provided in the connector installation section 36, such that they protrude, as shown in FIG. 4, FIG. 7 and FIG. 13.

Next is a description of the drive unit 34.

As shown in FIG. 7, the drive unit 34 is provided with two motor units 211 and 212 as driving sources.

The two motor units 211 and 212 are installed so as to manage the bending directions of the bending section 23. That is, the motor unit 211 is for the vertical bending direction, and the motor unit 212 is for the horizontal bending direction.

The motor units 211 and 212 comprise motor sections 215 and 216 and reduction gear sections 217 and 218 formed by gear trains such as spur gears, planetary gears, or the like, which transmit the driving force from their motor sections 215 and 216 to the output shafts 213 and 214. Furthermore, encoders 219 and 220 for detecting the rotation of the motor sections 215 and 216 are arranged in line in the motor units 211 and 212.

As shown in FIG. 4, cables 221 and 222, which lead from the positive terminals and the negative terminals of the motor sections 215 and 216, and which carry signals from the two encoders, are connected to the electric bending circuit section 35.

Using such a construction, the endoscope 2 is provided in the elongated insertion section 21, with a bending section 23 that can be bent at will, The bending control wires 131, 132, 133 and 134 are provided such that they extend from the bending section 23.

The drive unit 34 has drive sources (motor units 211 and 212) for generating driving forces, and is a drive section that can be attached to and removed from the endoscope 2 at will.

The pulling apparatus 91 pulls the bending control wires 131, 132, 133 and 134 by the driving forces applied, and is a pulling section for bending the bending section 23.

The female screw sections 231 and 232, the male screw sections 181 and 182, and the fixing knobs 183 and 184, are fixing devices for fixing the pulling apparatus 91 to the drive unit 34.

The connecting pins 301 and 302 are arranged such that they can be attached to and removed from the drive unit 34 and the pulling apparatus 91, separately from the fixing devices, and are transmission devices for transmitting the driving force from the drive source to the pulling apparatus 91.

The drive unit 34 has male output shafts 213 and 214 from the motor units 211 and 213, and the pulling apparatus 91 has female D holes 159 and 160 in the pulley sections 153 and 154.

The connecting pins 301 and 302 are connecting sections for connecting the male and female components.

(Operation of the Invention)

Hereunder is a description of the operation of the endoscope apparatus 1 of the first embodiment.

Normally, as shown in FIG. 1, it is used in a state where the connector section 9 is connected to the drum section 3.

The operation of the endoscope apparatus 1 as it is set up in the state of FIG. 1 will be described.

Firstly, as shown in FIG. 2, the lid 82 of the storage case 8 is opened, the cover panel 55 is opened, and the drum section 3 is rotated until its connector installation section 36 can be observed from above. Then, the industrial endoscope 2 to be used is fitted to the connector installation section 36 of the drum section 3.

At this time, as shown in FIG. 14, the connector section 9 is installed from above the connector installation section 36. Then, the light guide connector 112 of the connector section 9 as shown in FIG. 4, FIG. 7, FIG. 13 and FIG. 14 is fitted in the light guide connector receiving section 37 on the drum section 3 as shown in FIG. 4, FIG. 7, FIG. 12 and FIG. 14.

Next, the male image connector 119 on the connector section 9 as shown in FIG. 4, FIG. 7 and FIG. 13, is plugged into the female image connector 38 on the drum section 3 as shown in FIG. 4, FIG. 7 and FIG. 12.

Then, the male screw sections 181 and 182 as shown in FIG. 13 make contact with the threaded holes 231 and 232 of the connector installation section 36 as shown in FIG. 12. Thus, the connector section 9 is fastened onto the connector installation section 36 by opening the curved panel 95 and turning the fixing knobs 183 and 184. In this manner, the connector section 9 is installed in the connector installation section 36.

Next, as shown in FIG. 15, it is arranged such that the bearing parts 171 and 172 can be observed.

Here is a description of the connection between the output shaft 214 and the pulley section 154 on the horizontal bending direction side.

As shown in FIG. 16, an operator grips the gripping section 306 of the connecting pin 302, and inserts the connecting section 304 through the bearing section 172.

Then, the operator pushes the connecting pin 302 into the D hole 160, rotating it until it fits in the D shape of the connecting section 304. In this manner, as shown in FIG. 17, the end of the connecting section 304 reaches the D hole 160.

At this time, the operator can make the connecting pin 302 reach the D hole 160 easily by manipulating it while checking the connecting section 304 by visual observation from above. Furthermore, the operator makes the end of the connecting pin 302 contact the pulley section 154, and pushes it into the pulley section 154 while turning the connecting pin 302 slightly, thus enabling the connecting section 304 in the D hole 160 to be inserted easily.

Next, by pushing and adjusting as it rotates in a state where the connecting pin 302 fits in the pulley section 154, such that the end of the connecting section 304 fits the D shape of the output shaft 214, the end of the connecting section 304 reaches the output shaft 214 as shown in FIG. 18.

At this time, by the operation being performed while observing the end of the output shaft 214 visually through the observation hole 312, it is easy for the connecting pin 302 to reach the output shaft 214.

Furthermore, when the connecting pin 302 is pushed in a state where the D hole 160 and the output shaft 214 are engaged with the connecting section 304, the C ring 308 makes contact with the bearing section 172 as shown in FIG. 19.

Then, the connecting pin 302 is pushed further, the C ring 308 deforms toward the C ring groove 310, and the C ring 308 drops into the engagement groove 178 of the bearing section 172 as shown in FIG. 20.

Thus, the output shaft 214 and the pulley section 154 on the horizontal bending direction side are connected, so that the driving force of the motor section 216 can be transmitted.

Furthermore, by doing the same for the output shaft 213 and the pulley section 153 on the vertical bending direction side, the connection between the drive unit 34 and the pulling apparatus 91 is completed.

In this manner, assembly of the connector section 9 onto the connector installation section 36 is completed.

Then, as shown in FIG. 1, the cover panel 55 is closed such that the insertion section 21 is sandwiched by the rubber pieces 53 and 54. The cover panel 55 and the front panel 5 are provided with a fixing device, which is not shown in the figure, and the construction is such that it is not opened and closed except when required.

The apparatus is now ready for use.

Here, in a case where the industrial endoscope 2 is not used after it is assembled, the drum section 3 is rotated so that the insertion section 21 is wound into the drum section 3, and the lid 82 is closed. That is, in a state other than when it is used, such as when it is being stored, moved, or the like, the insertion section 21 is wound onto the outer circumference of the drum section 3.

Next is a description of the operation when it is used. Although there is some duplication, the description is up until the apparatus is ready for use. Firstly, as shown in FIG. 1, the lid 82 of the storage case 8 is opened, the AC cable 51 is connected to a socket, and the remote controller 6 is taken out. Afterwards, the insertion section 21 is gripped near the tip section body 22, and the insertion section 21 pulled out slowly. Then, the drum section 3 is rotated by the pulling force, the insertion section 21 is pulled out, and the preparation of the insertion section 21 is complete at the point of time when the whole of the insertion section 21 is pulled out.

Next, an optical adaptor 25 required for examination is selected, the optical adaptor 25 is fitted on the tip section body 22, and the power button 63 provided on the remote controller 6 is turned on. Thus, examination is now possible.

Next is a description of the bending operation. The driving operation will be described for the drive unit 34, being an electric bending apparatus, by control by the remote controller 6.

By manipulating the joystick 62 of the remote controller 6 in a desired vertical or horizontal direction, a signal corresponding to the tilt angle of this joystick 62 is transmitted to the electric bending circuit section 35. Then, in this electric bending circuit section 35, the rotation of the output shafts 213 and 214 corresponding to the control signal is calculated mathematically, and rotation instruction signals corresponding to the calculated result are transmitted to the motor units 211 and 212.

The motor sections 215 and 216 rotate according to the rotation instruction signals transmitted from the electric bending circuit section 35. The rotations of each of the motor sections 215 and 216 are transmitted to the output shafts 213 and 214 via the reduction gear sections 217 and 218, and the output shafts 213 and 214 rotate. Then, the pulley sections 153 and 154 rotate as the output shafts 213 and 214 rotate. At this time, the rotations of the motor sections 215 and 216 are detected by the encoders 219 and 220; thus, in other words, the rotations of the output shafts 213 and 214 are detected by the encoders 219 and 220.

That is, the motor sections 215 and 216 operate in a state where the rotary positions of the output shafts 213 and 214 are always monitored by the encoders 219 and 220. Accordingly, the electric bending circuit section 35 controls such that the operations of the motor sections 215 and 216 are stopped at the point where the values calculated by the processing of the electric bending circuit section 35 match the rotary positions of the output shafts 213 and 214 detected by the encoders 219 and 220.

Accordingly, when the joystick 62 is manipulated, the bending section 23 is bent as described above, and the tip section body 22 is pointed in a desired direction at the time of examination so that an object can be observed.

In the case where the bending control wires 131, 132, 133 and 134 are pulled by a large amount, such as when the bending section 23 is bent at its maximum bending angle, the motor sections 215 and 216 rotate the output shafts 213 and 214, in other words the pulley sections 153 and 154 connected by the connecting pins 301 and 302, by a large amount under the control of the electric bending circuit section 35, selecting the pulling apparatus side wires 141, 142, 143 and 144, and winding them.

Next is a description of the bending operations performed as the pulley sections 153 and 154 rotate.

As described above, since the pulley sections 153 and 154 rotate as the joystick 62 is manipulated, the ends of the pulling apparatus side wires 141, 142, 143 and 144 rolled onto and connected to the pulley sections 153 and 154 move back and forth.

That is, since the insertion section side wires 135, 136, 137 and 138 connected by the male screw ferrule 168 and the female screw ferrule 169 move back and forth, the bending section 23 is bent in the direction in which the insertion section side wires 135, 136, 137 and 138 are pulled.

By combining movements in the vertical direction and the horizontal direction, bending operations can be performed in any desired direction in the vertical or horizontal directions.

Accordingly, the bending section 23 is bent in a desired direction using the joystick 62, and any desired location may be examined in detail.

After the required bending operation is performed, and the plant or the like is examined, the insertion section 21 is withdrawn from the object to be examined, the insertion section 21 is wound onto the drum section 3, and the lid 82 is closed, thus completing the tidy up of the endoscope apparatus 1.

In the case where an industrial endoscope 2 configuration with a different diameter and insertion length is required, it is possible to return to the set up stage and assemble a connector section 9 of another industrial endoscope 2 with a different insertion section 21 onto the connector installation section 36. By making the connector section 9 common to all use, it is possible to reconfigure the industrial endoscope 2.

(Effects)

According to the first embodiment as described above, the drive unit 34 and the pulling apparatus 91 are separated, and industrial endoscopes 2 can be attached to and removed from the drum section 3 interchangeably; thus it is possible to select a suitable endoscope to use for an examination. In addition, when the drive unit 34 and the pulling apparatus 91 are assembled, there is a large amount of clearance at the connecting sections 303 and 304 between the two shaft bodies, being the protruding output shafts 213 and 214 and the D holes 159 and 160 joined with the output shafts 213 and 214, so it is easy to connect the output shafts 213 and 214 and the pulley sections 153 and 154.

Especially, in the operation of installing the connector section 9 from above, the D holes 159 and 160 and the output shafts 213 and 214 of the pulley sections 153 and 154 tend to be in a location that cannot be seen by an operator. Therefore, the smaller the clearance, and the greater the number of fittings, the more difficult it is to fit the shafts and the holes in the hidden area together. In order to make it easier to fit the shafts and the holes together in this situation, it is necessary to increase the clearance between them to allow more play. However, if there is too much play, it causes backlash between the pulley sections and the output shafts, and the reverse operation of the output shafts is not reflected linearly in the reverse operation of the pulley section, which can easily lead to a drop in bending performance.

However, as described above, by designing in play between the D holes 159 and 160 and the output shafts 213 and 214, and minimizing the play with the connecting pins 301 and 302, this problem is solved.

That is, the play between the D holes 159 and 160 and the output shafts 213 and 214 has an effect in that it improves the installation of the connector section 9 into the connector installation section 36, and the connecting pins 301 and 302 that close up the space, maintain the bending performance.

As a result, in the case where driving force is transmitted from a drive unit 34 capable of being attached to and removed from the endoscope 2 to the pulling apparatus 91 for bending the bending section 23 of the endoscope 2, the driving force can be transmitted stably, thus enabling the stability and accuracy of the bending operation of the bending section 23 to be improved.

SECOND EMBODIMENT

Figure 21:
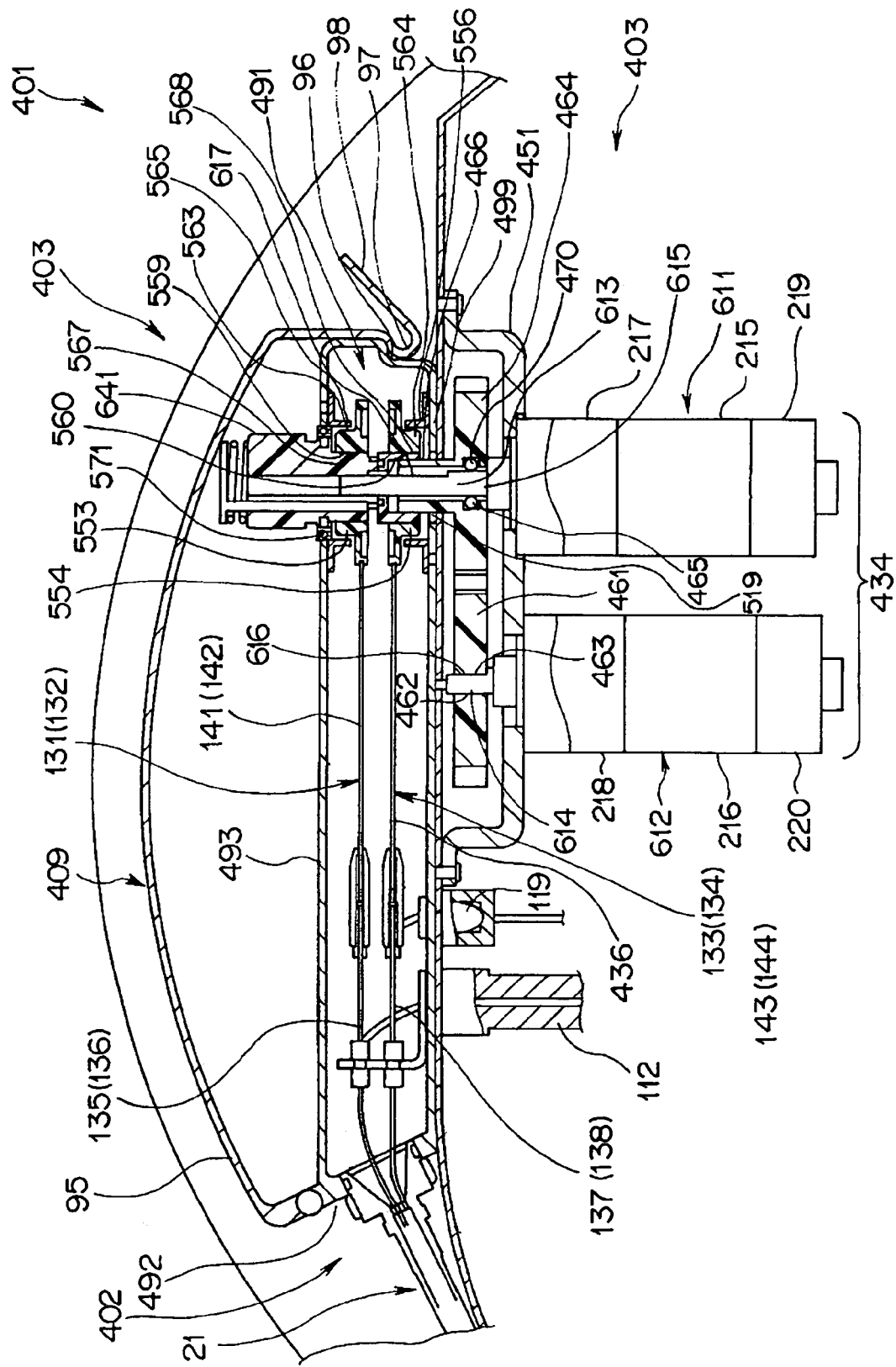
FIG. 21 is a cross-sectional diagram of a drum section according to a second embodiment of the present invention.
Figure 22:
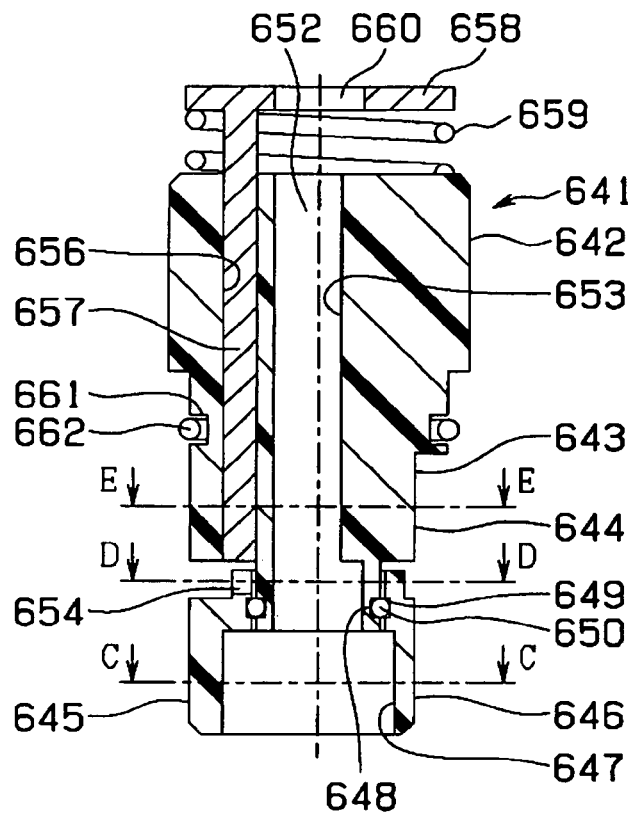
FIG. 22 is a cross-sectional diagram of a connecting device according to the second embodiment of the present invention.
Figure 23:
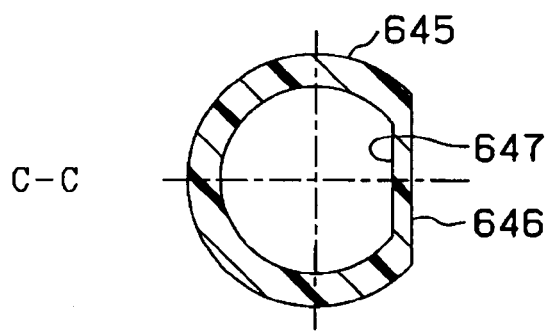
FIG. 23 is a cross-sectional diagram through line C-C of FIG. 22, according to the second embodiment of the present invention.
Figure 24:
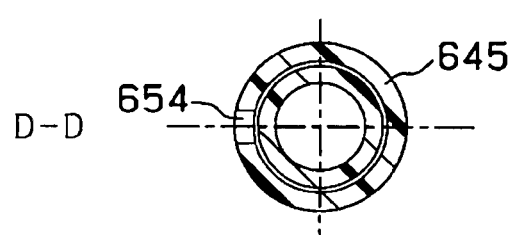
FIG. 24 is a cross-sectional diagram through line D-D of FIG. 22, according to the second embodiment of the present invention.
Figure 25:
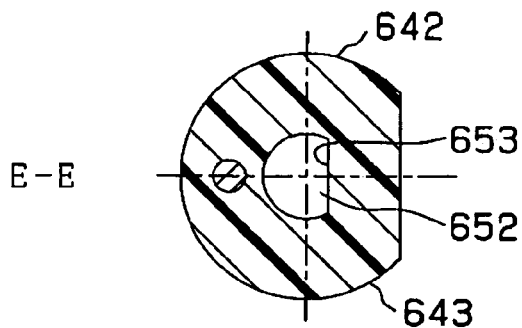
FIG. 25 is a cross-sectional diagram through line E-E of FIG. 22, according to the second embodiment of the present invention.
Figure 26:
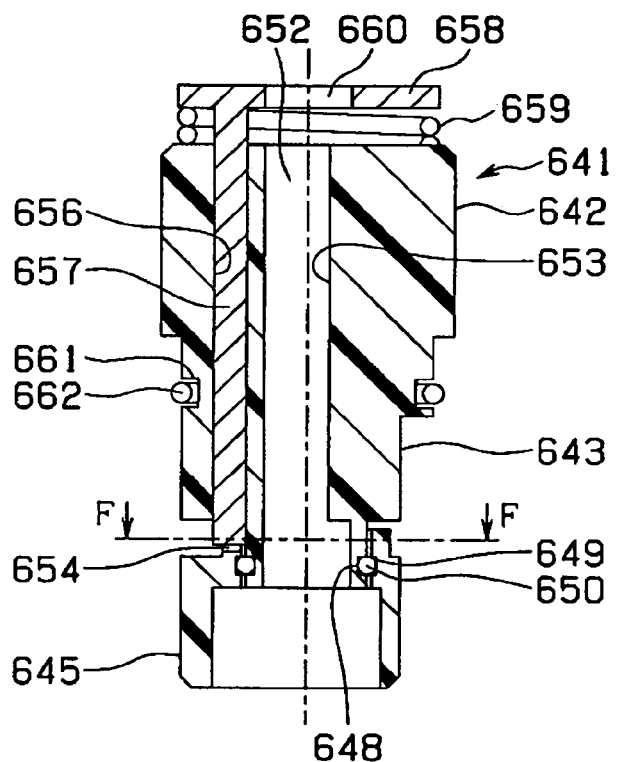
FIG. 26 is a cross-sectional diagram of a connecting pin in the case where a press section is pressed, according to the second embodiment of the present invention.
Figure 27:
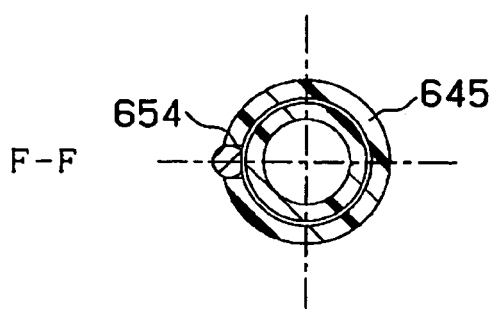
FIG. 27 is a cross-sectional diagram through line F-F of FIG. 26 according to the second embodiment of the present invention.
Figure 28:
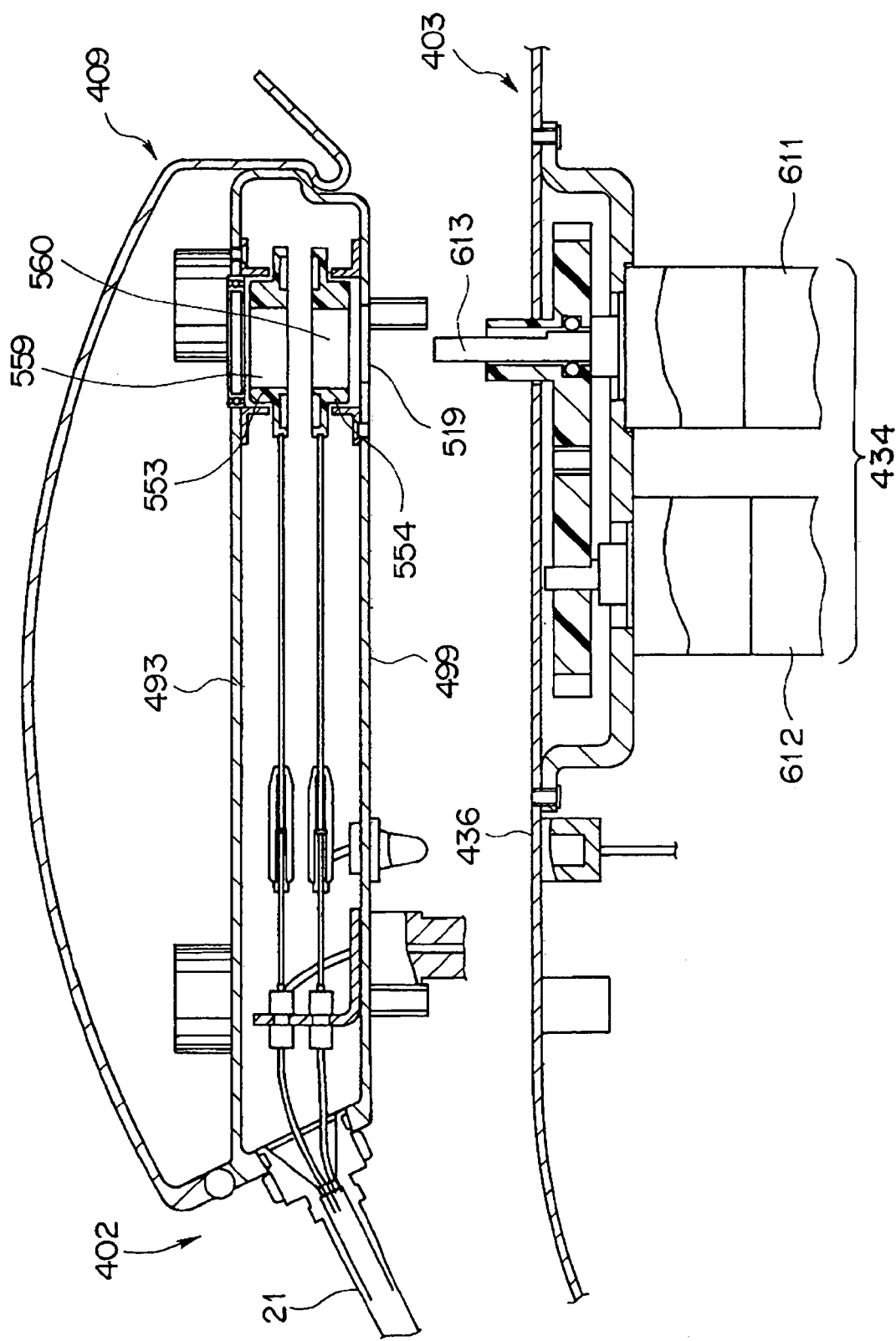
FIG. 28 is a partially enlarged diagram of the main parts in a state before a connector section is installed in the connector installation section, according to the second embodiment of the present invention.
Figure 29:
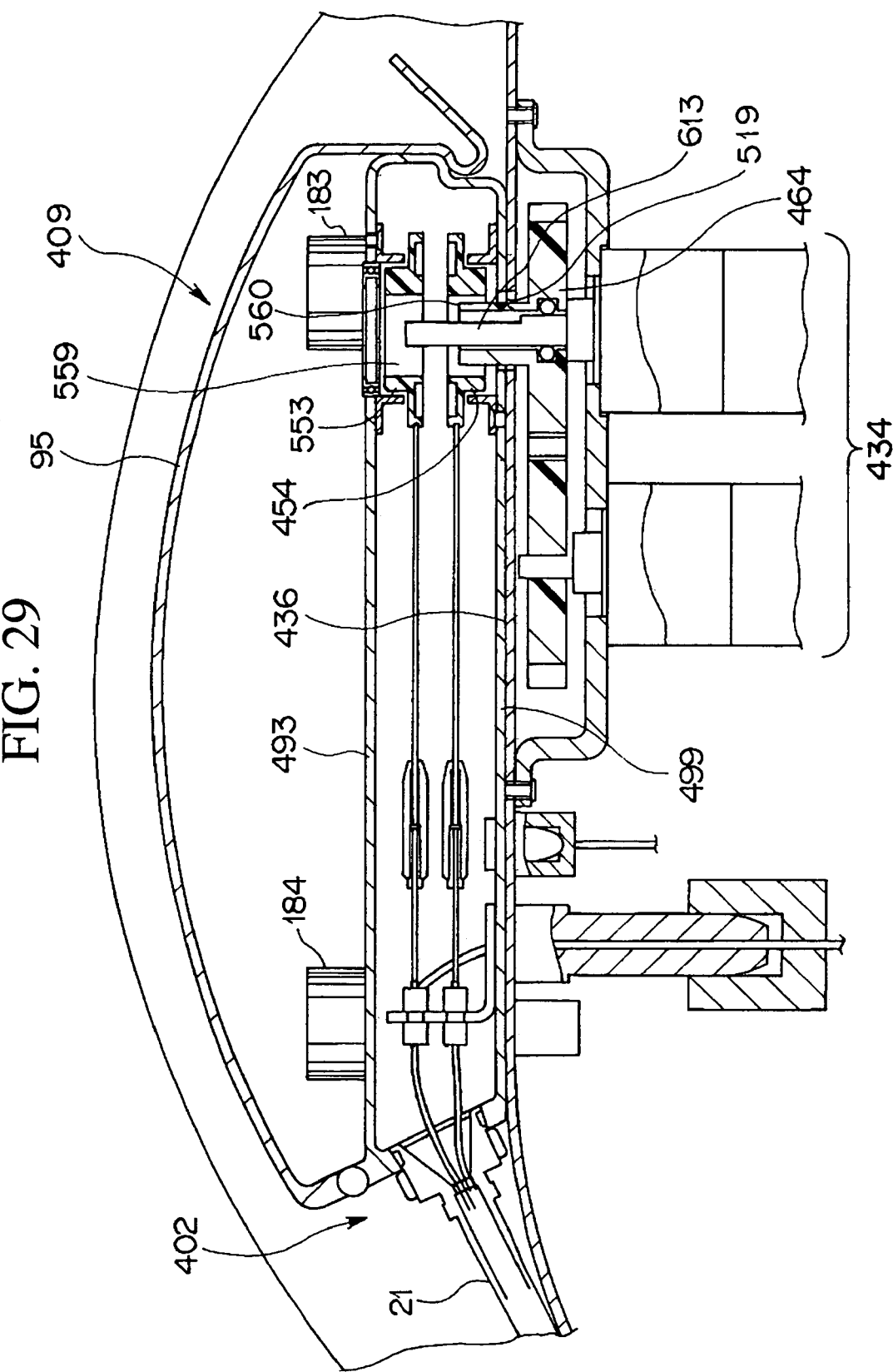
FIG. 29 is a partially enlarged diagram of the main parts in a state in which the connector section is installed in the connector installation section, according to the second embodiment of the present invention.
Figure 30:
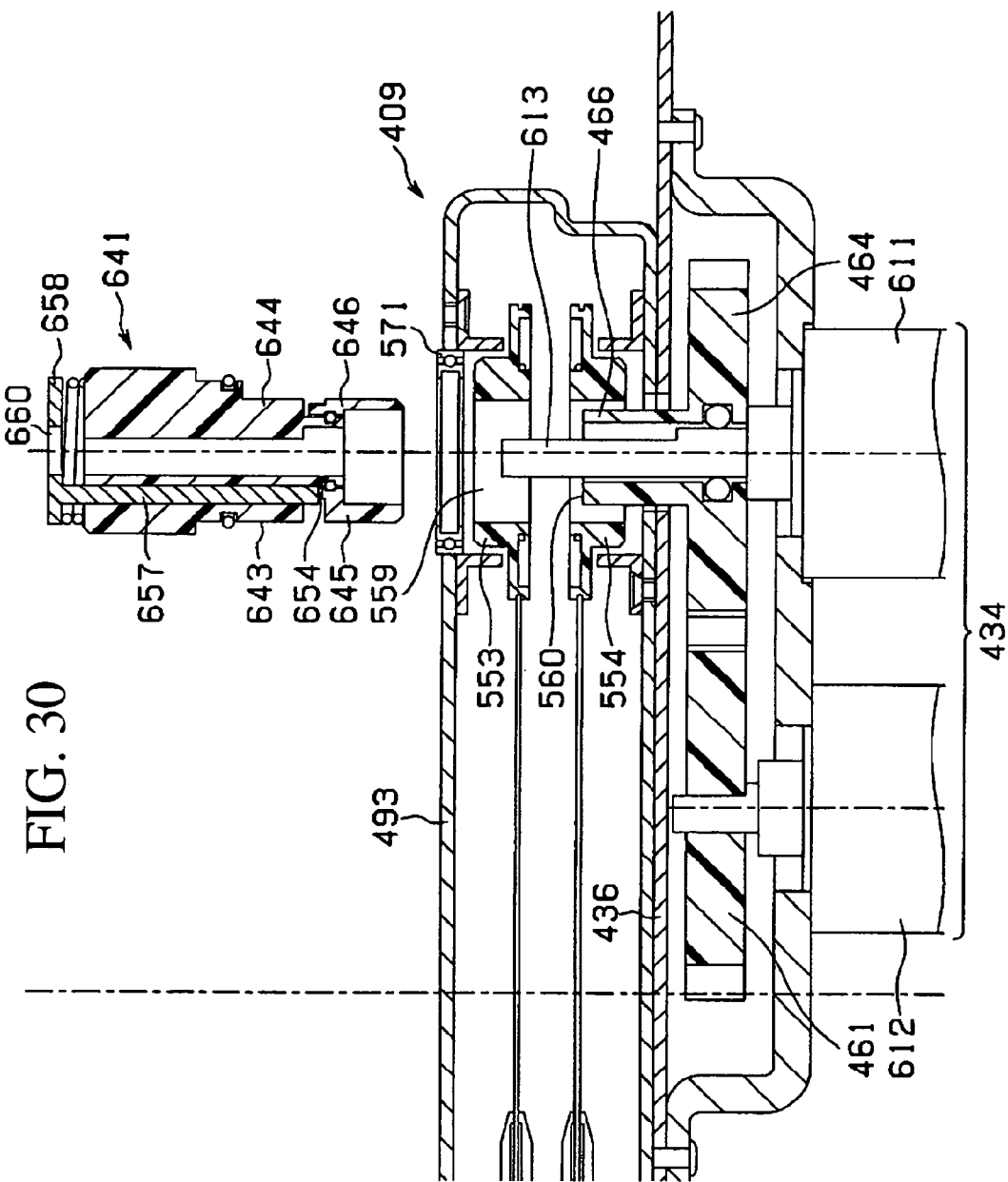
FIG. 30 is a partially enlarged diagram of the main parts in a state before a connecting device is installed in a pulley section, according to the second embodiment of the present invention.
Figure 31:
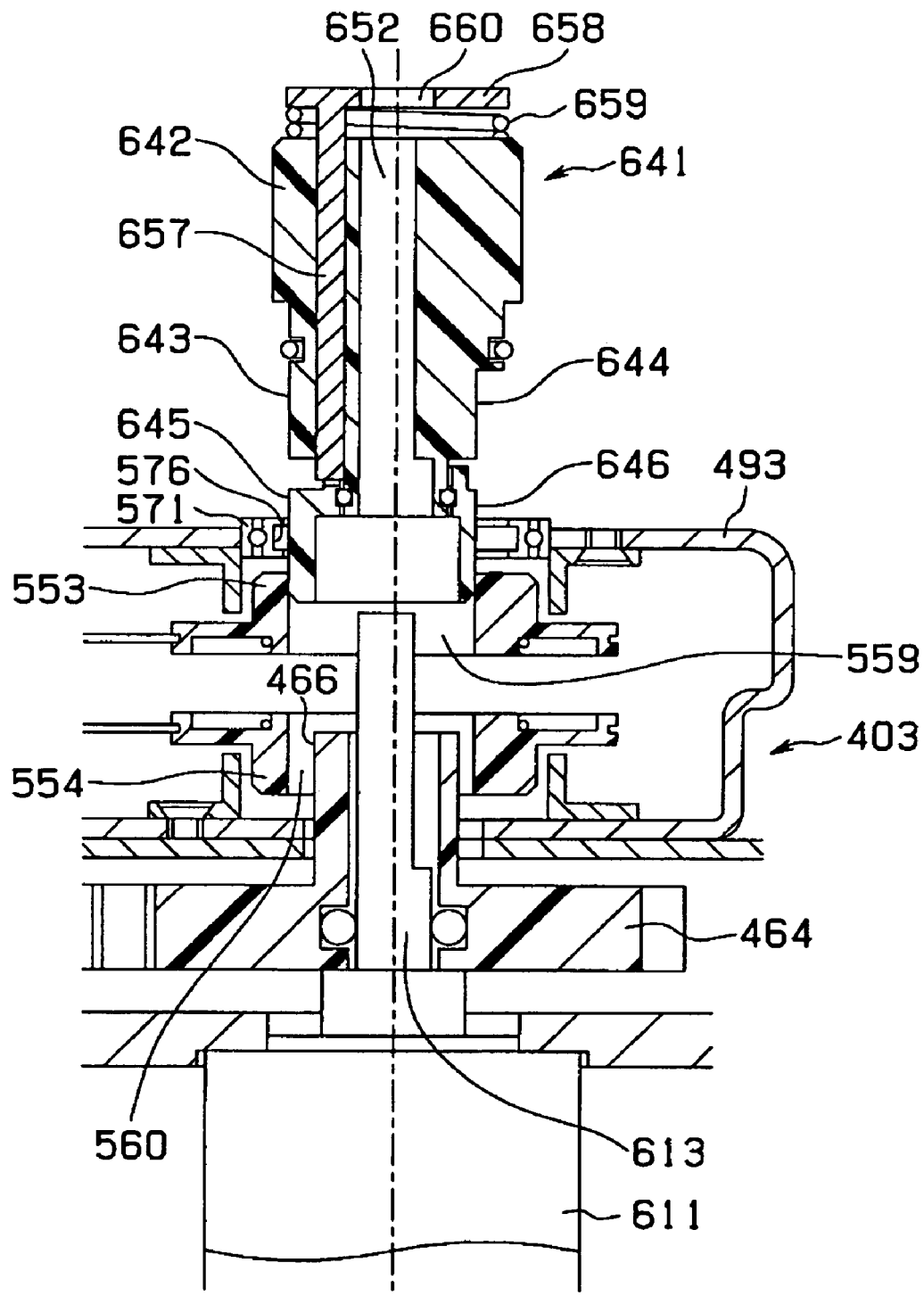
FIG. 31 is an explanatory diagram showing a first state of the operation whereby the connecting device is installed in the pulley section, according to the second embodiment of the present invention.
Figure 32:
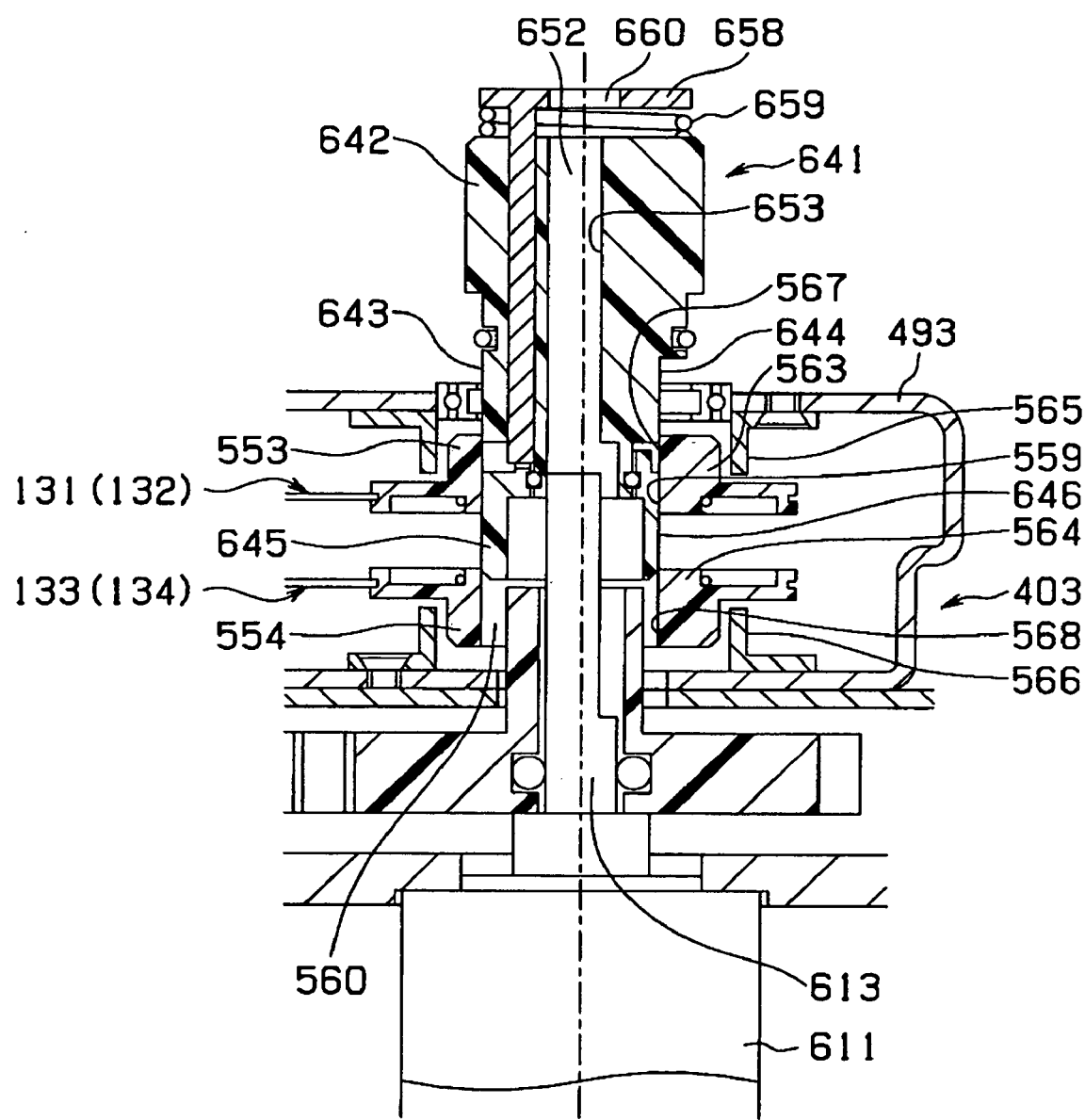
FIG. 32 is an explanatory diagram showing a second state of the operation whereby the connecting device is installed in the pulley section, according to the second embodiment of the present invention.
Figure 33:
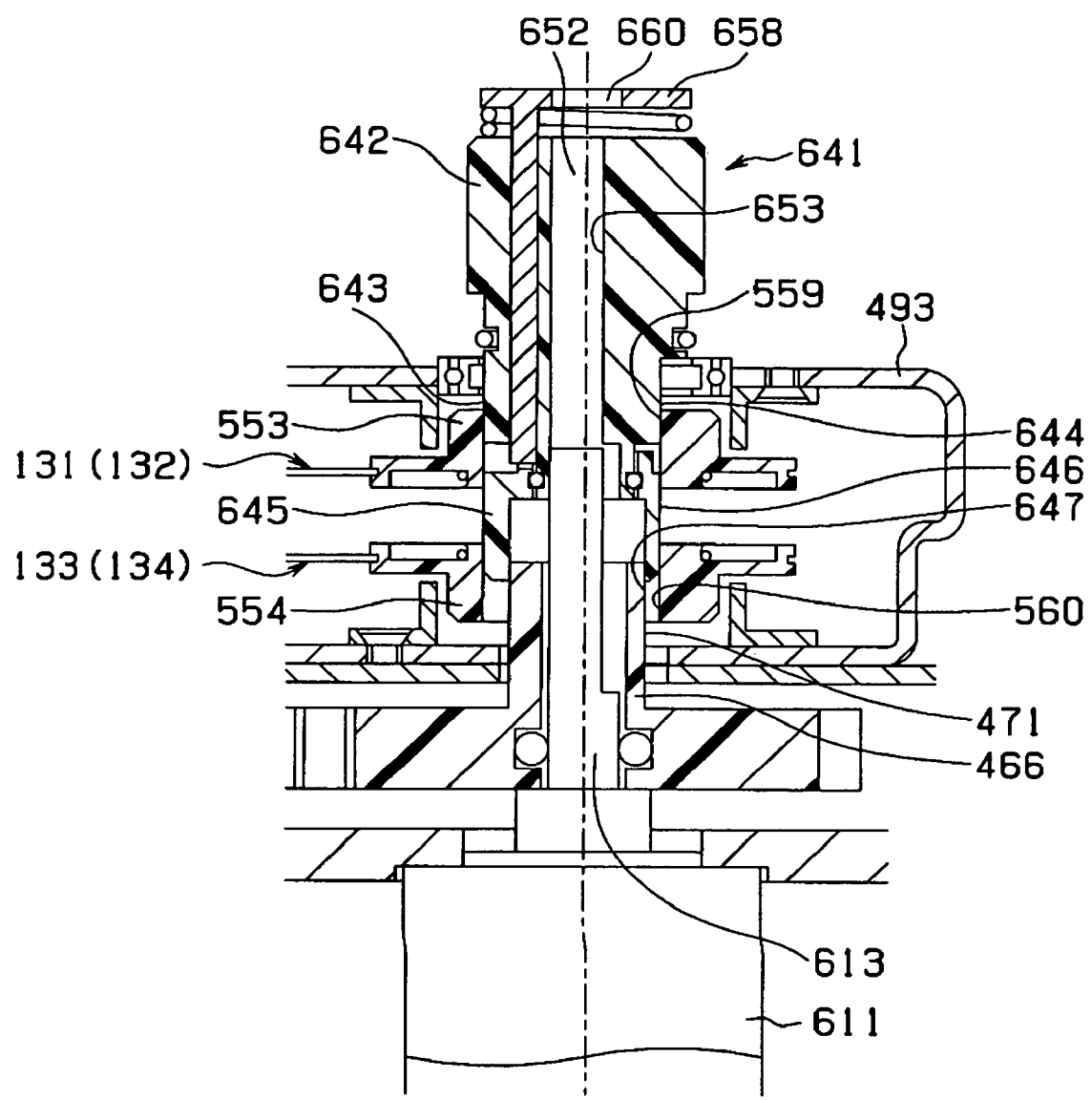
FIG. 33 is an explanatory diagram showing a third state of the operation whereby the connecting device is installed in the pulley section, according to the second embodiment of the present invention.
Figure 34:
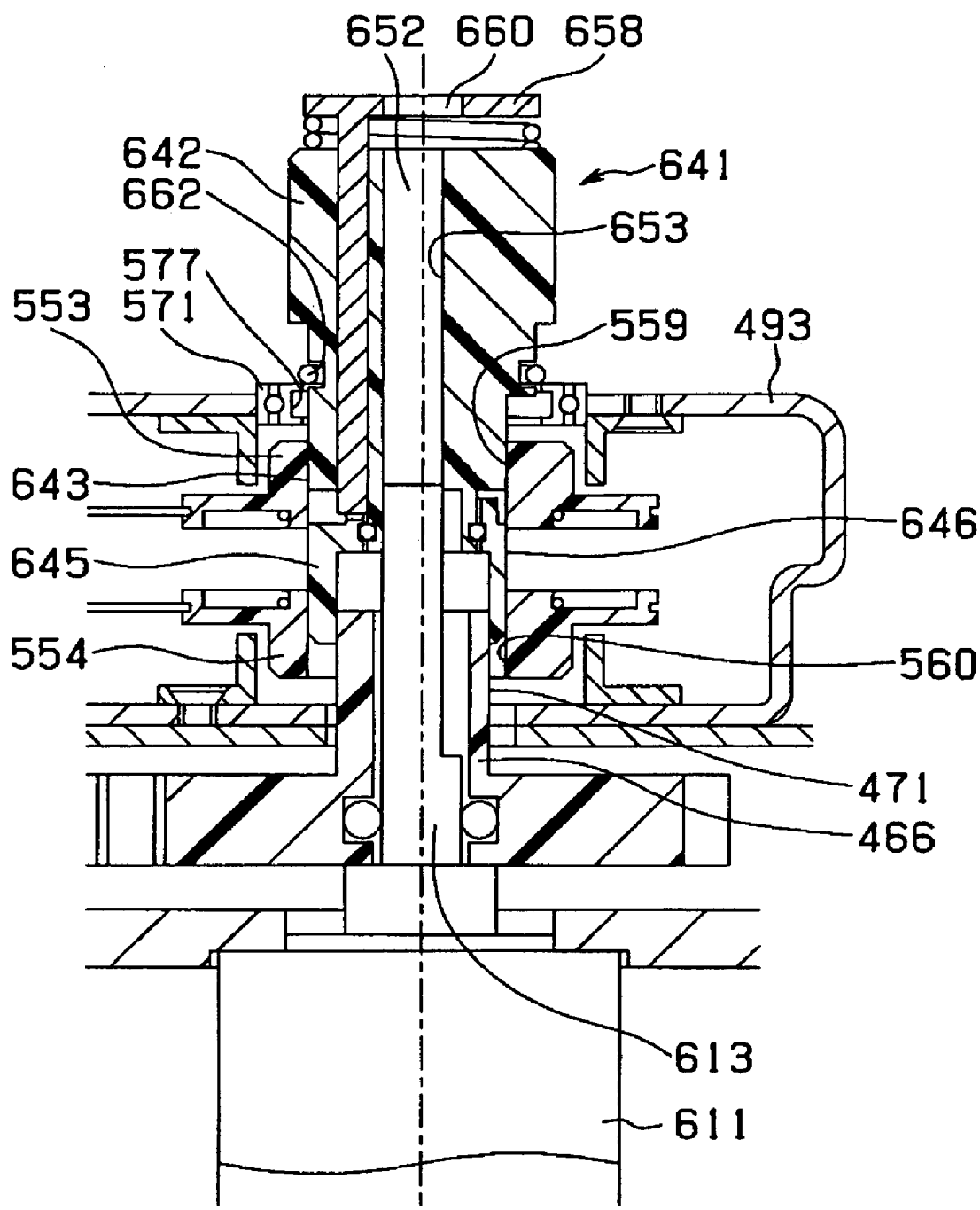
FIG. 34 is an explanatory diagram showing a fourth state of the operation whereby the connecting device is installed in the pulley section, according to the second embodiment of the present invention.
Figure 35:
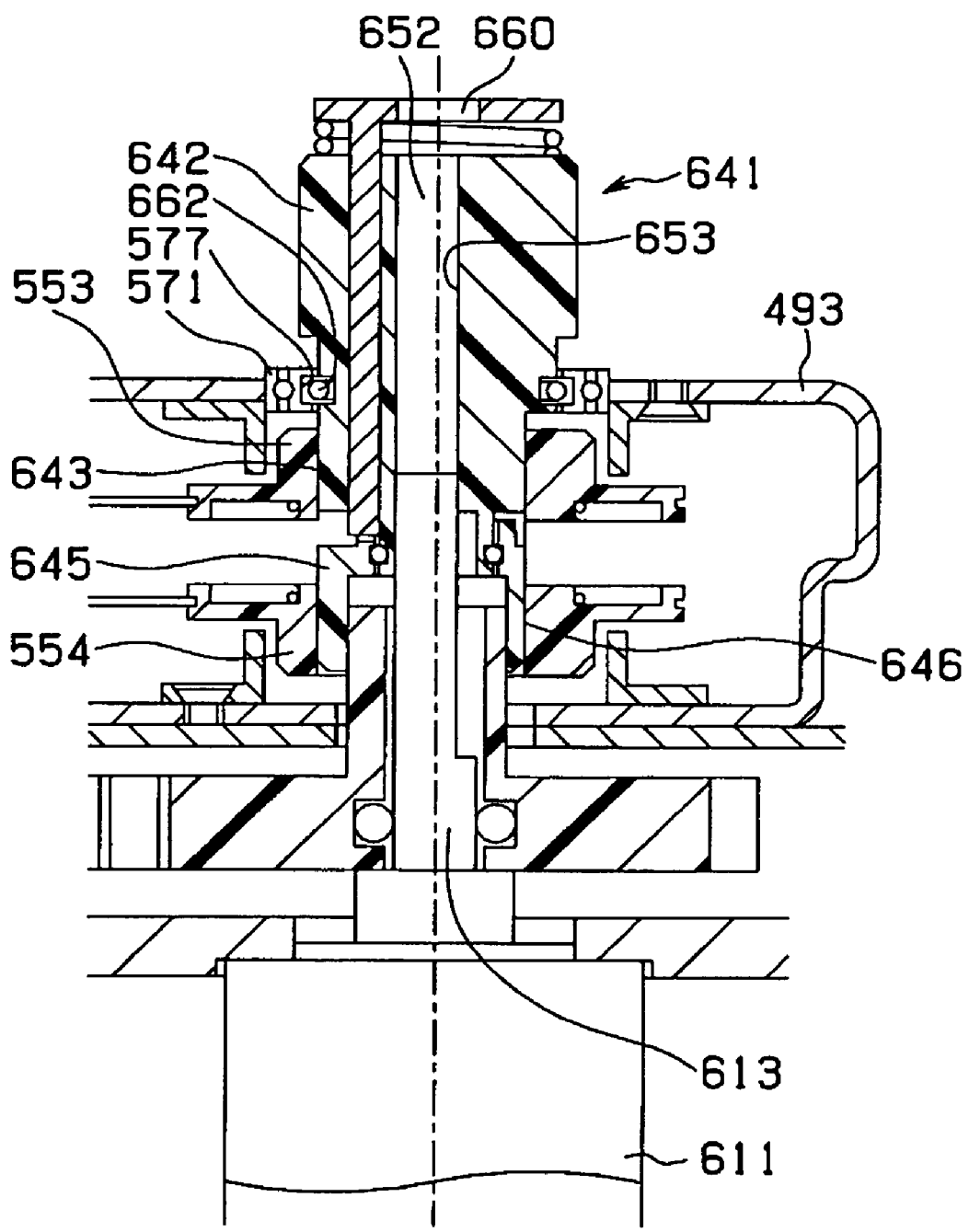
FIG. 35 is an explanatory diagram showing a fifth state of the operation whereby the connecting device is installed in the pulley section, according to the second embodiment of the present invention.
Figure 36:
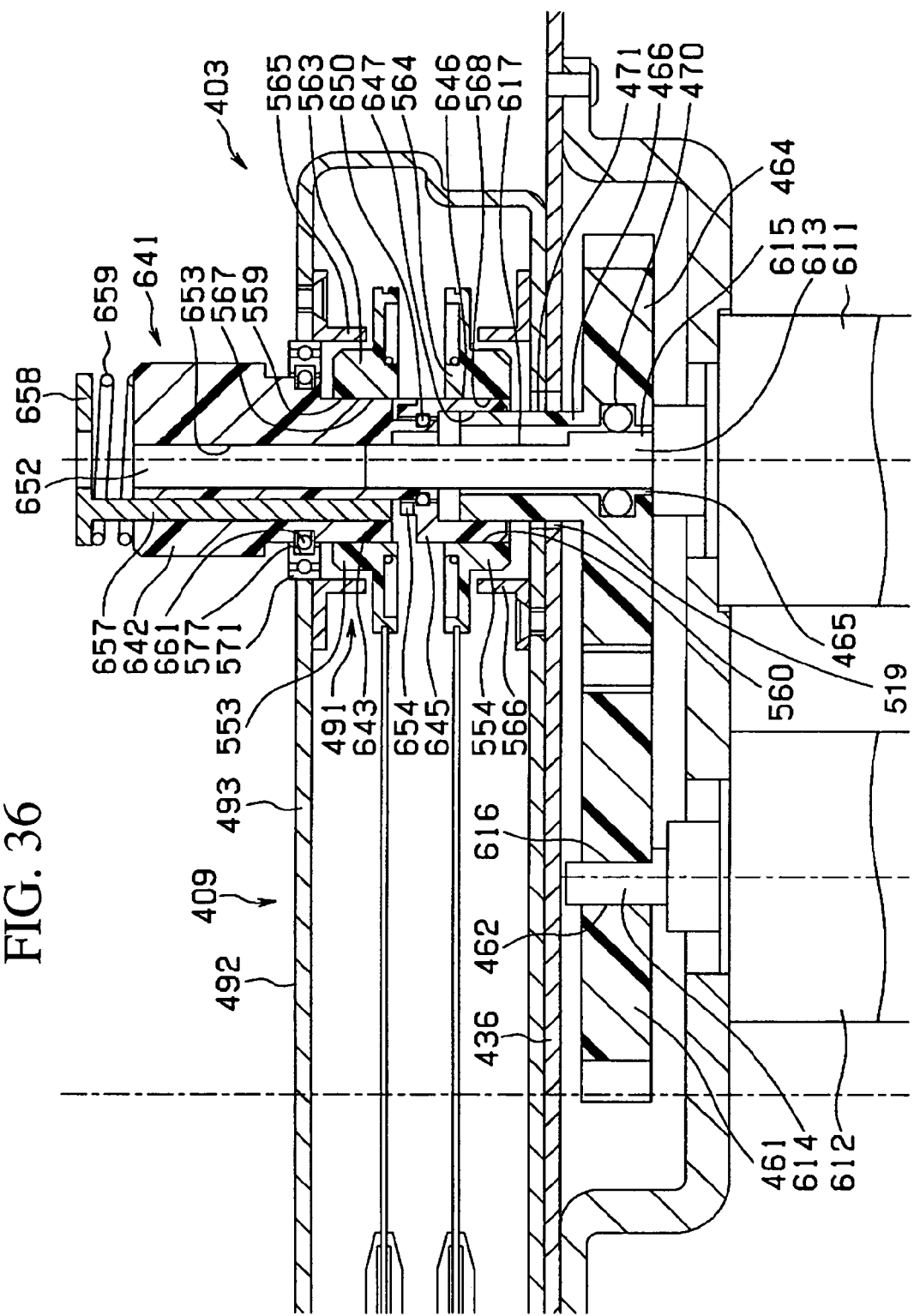
FIG. 36 is an explanatory diagram showing a sixth state of the operation whereby the connecting device is installed in the pulley section, according to the second embodiment of the present invention.

FIG. 21 to FIG. 36 are diagrams associated with a second embodiment of the present invention. FIG. 21 is a cross-sectional diagram of a drum section. FIG. 22 is a cross-sectional diagram of a connecting device. FIG. 23 is a cross-sectional diagram through line C-C of FIG. 22. FIG. 24 is a cross-sectional diagram through line D-D of FIG. 22. FIG. 25 is a cross-sectional diagram through line E-E of FIG. 22. FIG. 26 is a cross-sectional diagram of a connecting pin in the case where a press section is pressed. FIG. 27 is a cross-sectional diagram through line F-F of FIG. 26. FIG. 28 is a partially enlarged diagram of the main parts in a state before the connector section is installed in the connector installation section. FIG. 29 is a partially enlarged diagram of the main parts in a state in which the connector section is installed in the connector installation section. FIG. 30 is a partially enlarged diagram of the main parts in a state before a connecting device is installed in a pulley section. FIG. 31 is an explanatory diagram showing a first state of the operation whereby the connecting device is installed in the pulley section. FIG. 32 is an explanatory diagram showing a second state of the operation whereby the connecting device is installed in the pulley section. FIG. 33 is an explanatory diagram showing a third state of the operation whereby the connecting device is installed in the pulley section. FIG. 34 is an explanatory diagram showing a fourth state of the operation whereby the connecting device is installed in the pulley section. FIG. 35 is an explanatory diagram showing a fifth state of the operation whereby the connecting device is installed in the pulley section. FIG. 36 is an explanatory diagram showing a sixth state of the operation whereby the connecting device is installed in the pulley section.

Here, the same symbols are used for structures with the same operations and effects as in the above-described first embodiment, and the descriptions are omitted.

(Construction)

As shown in FIG. 21, in a drive unit 434 of a drum section 403 of an endoscope apparatus 401, a motor unit 611 for the vertical bending direction, and a motor unit 612 for the horizontal bending direction, are arranged in parallel in a motor unit retaining frame 451. In motor unit 612 of the motor units 611 and 612, an output shaft 614 is provided with a first stage gear 461.

The output shaft 614 and the first stage gear 461 are fitted together by press fitting the output shaft 614, whose cross section is D shaped, into a first stage gear D hole 462 whose cross section is D shaped. Furthermore, the construction is such that the output shaft 614 and the first stage gear 461 are prevented from rotating relative to each other by contact between a flat output shaft section 616, which forms a flat section on the output shaft 614, and a flat first stage gear section 463, which is provided in the first stage gear D hole section 462, and forms a flat section.

Furthermore, a final stage gear 464 engages with this first stage gear 461. An output shaft 613 as described later is inserted in the final stage gear hole section 465 provided in the final stage gear 464. Here, there is sufficient clearance between the final stage gear hole section 465 and the output shaft 613. The rounded output shaft face 615 of the output shaft 613 and the final stage gear hole section 465 are supported by a plurality of balls 470; thus the construction of the final stage gear hole section 465 and the output shaft 613 is in the form of a ball bearing.

Furthermore, this final stage gear 464 has a protruding output sleeve 466 with a D shaped cross section that fits together with the connecting device 641 as described later.

Moreover, the output shaft 613 is longer than the output shaft 614, and the construction is such that it has a rounded output shaft face 615 on the gear section 217 side, and a flat output shaft section 617 on the tip side, and it is connected to the pulley section 553 by the connecting device 641 on the tip side of the output shaft 613.

To be specific, as shown in FIG. 36, the output shaft 613 fits in a press section observation hole 652 in the connecting device 641, and the flat output shaft section 617 and a flat main body observation hole section 653, which forms a flat face in the D hole of the press section observation hole 652, make contact.

Next is a description of the pulley sections 553 and 554.

As shown in FIG. 21 and FIG. 36, a pulley section 553 for the vertical bending direction, and a pulley section 554 for the horizontal bending direction, are stacked as a pulling apparatus 491 in the vertical direction on the page.

The pulley sections 553 and 554 are provided with D holes 559 and 560, which fit together with a connecting device 641 as described later. Furthermore, the pulley sections 553 and 554 have support sleeves 565 and 566 for supporting hubs 563 and 564 such that they can rotate. Here, since the support sleeves 565 and 566 support the hubs 563 and 564 as they rotate, in a state where there is a certain degree of clearance between the hubs 563 and 564 and the support sleeves 565 and 566, there is some play in the pulley sections 553 and 554 due to the clearance around the shaft centers of the hubs 563 and 564.

The D holes 559 and 560 are provided with flat D hole sections 567 and 568 forming flat faces in the D holes.

Furthermore, the base 499 of the connector case body 493 is provided with an output shaft insertion hole 519 as described later, in which the output shaft 613 is inserted.

Next is a detailed description of the connecting device 641, using FIG. 21 through FIG. 27 and FIG. 36.

As shown in FIG. 21 through FIG. 27, the connecting device 641 has a connecting device body 642. The connecting device body 642 is provided with a vertical direction pulley connecting section 643 which fits in the above-described D hole 559. The vertical direction pulley connecting section 643 is provided with a pulley connecting flat section 644 which makes contact with the flat D hole section 567 of the D hole 559 of FIG. 21.

A horizontal direction pulley connecting section 645 is provided at the tip end, such that it can rotate. Here, a pulley connecting flat section 646, which contacts the flat face 568 of the D hole 560 of FIG. 21, is provided on the outer circumference of the horizontal direction pulley connecting section 645. An output sleeve connecting flat section 647, which is connected to an output sleeve 466 as shown in FIG. 36, and contacts an output sleeve flat section 471, is provided on the internal circumference.

A slot section 648 provided in the connecting device body 642, and a slot section 649 provided in the horizontal direction pulley connecting section 645, are supported and engaged by a plurality of balls 650 on the connecting device side. Thus, this horizontal direction pulley connecting section 645 is in the form of a ball bearing.

Furthermore, as shown in the cross section D-D of FIG. 24, the horizontal direction pulley connecting section 645 is provided with a locking slot 654, and the end of a locking key 657, which is fitted through a locking key path 656 provided in the connecting device body 642 as shown in FIG. 22, is engaged at will in this locking slot 654.

Here, as shown in FIG. 22, this locking key 657 has a press section 658 on the base end side, and the press section 658 is supported by a spring section 659.

The connecting device body 642 and the press section 658 have a main body observation hole 652 and a press section observation hole 660 respectively to observe the tip end. This main body observation hole 652 is provided with a main body observation hole flat section 653 which fits onto the output shaft flat section 617 of the above-described output shaft 613.

Furthermore, in the connecting device body 642, a C ring 662, which engages in an engagement slot 577 of a bearing part 571 provided in the connector case body as shown in FIG. 36, clips into a C ring slot 661.

(Operation of the Invention)

Hereunder is a description of the operation of the endoscope apparatus 401 of the second embodiment.

As shown in FIG. 28, the connector section 409 is positioned above the connector installation section 436 of the drum section 403, and as shown in FIG. 29, the output shaft 613 is inserted in the output shaft insertion hole 519.

Then, the curved panel 95 is opened, male screws 181 and 182 (refer to FIG. 13) are screwed into the threaded holes 231 and 232 (refer to FIG. 12) by the fixing knobs 183 and 182 to fasten the connector section 409 onto the connector installation section 436.

Then, as shown in FIG. 30, the connecting device 641 is prepared in a position facing the bearing part 571.

At this time, as shown in FIG. 26, the press section 658 is pushed by an operator to engage the end of the locking key 657 in the locking slot 654, so that the pulley connecting flat section 644 and the pulley connecting flat section 646 of the connecting device 641 face in the same direction, and the horizontal direction pulley connecting section 645 does not rotate.

In this situation, as shown in FIG. 31, the horizontal direction pulley connecting section 645 is inserted into the bearing part 571, and furthermore pushed toward the D hole 559 of the pulley section 553.

At this time, it is inserted while confirming the direction of the pulley connecting flat section 646 and the direction of the flat D hole section 567 of the D hole 559 from above the bearing part 571.

Next, by inserting it further, as shown in FIG. 32, the end of the horizontal direction pulley connecting section 645 reaches the D hole 560 of the pulley section 554. At this time, the direction of the D hole 560 may shift slightly from the direction of the D hole 559 due to the tensions of the bending control wires 131, 132, 133 and 134 and the play between the hubs 563 and 564 and the support sleeves 565 and 566. However, by moving the connecting device body 642 slightly in the direction of rotation, the direction of the pulley connecting flat section 646 of the horizontal direction pulley connecting section 645 matches the direction of the flat D hole section 568 of the D hole 560, so that the horizontal direction pulley connecting section 645 can be inserted in the D hole 560.

At this time, the vertical direction pulley connecting section 643 is inserted in the D hole 559 following the horizontal direction pulley connecting section 645. In this case, since the horizontal direction pulley connecting section 645 maintains the direction of the flat D hole section 567 of the D hole 559, the vertical direction pulley connecting section 643 can be inserted in the D hole 559 easily.

Furthermore, as shown in FIG. 33, the horizontal direction pulley connecting section 645 reaches the output sleeve 466. Then, the horizontal direction pulley connecting section 645 covers the output sleeve 466, and fits together with it while adjusting the direction of the output sleeve connecting flat section 647 and the output sleeve flat section 471.

At this time, the direction of the horizontal direction pulley connecting section 645 and the direction of the output sleeve flat section 471 may shift slightly due to the tensions of the bending control wires 131, 132, 133 and 134 and the play between the hubs 563 and 564 and the support sleeves 565 and 566. However, by rotating the connecting device body 642 slightly in the horizontal direction, the direction of the output sleeve flat section 471 matches the direction of the output sleeve connecting flat section 647, so that the horizontal direction pulley connecting section 645 fits together with the output sleeve 466. At this time, the horizontal direction pulley connecting section 645 and the D hole 560 are in the process of fitting together, and the vertical direction pulley connecting section 643 and the D hole 559 are in the process of fitting together. Therefore, in the case when the connecting device body 642 is rotated, the horizontal direction pulley connecting section 645 covers the output sleeve 466 while the connecting device 641 rotates the pulley sections 553 and 554.

Next, as the mating of the horizontal direction pulley connecting section 645 and the output sleeve 466 proceeds further, the output shaft 613 is inserted in the main body observation hole 652 as shown in FIG. 34, and the C ring 662 contacts the bearing part 571. By continuing to push the connecting device 641, the C ring 662 deforms elastically, so that this C ring 662 is inserted into the engagement slot 577 of the bearing part 571 and engages with it as shown in FIG. 35.

Afterwards, when the pressing of the press section 658 is discontinued, the press section 658 is pushed up by the spring section 659 as shown in FIG. 36, and the locking key 657 ascends accordingly. Then, the engagement of the locking slot 654 and the locking key 657 is cancelled, and the horizontal direction pulley connecting section 645 and the vertical direction pulley connecting section 643 can be rotated relative to each other freely.

Next is a description of the bending operation.

The vertical bending direction will be described using FIG. 21 and FIG. 36.

By manipulating the joystick 62 (refer to FIG. 1) of the remote controller 6 (refer to FIG. 1) in a desired vertical direction, a signal corresponding to the tilt angle of this joystick 62 (refer to FIG. 1) is transmitted to the electric bending circuit section 35 (refer to FIG. 1). Then, in this electric bending circuit section 35 (refer to FIG. 1), the rotation of the output shaft 613 corresponding to the control signal is calculated mathematically, and a rotation instruction signal corresponding to the calculated result is transmitted to the motor unit 611 as shown in FIG. 36.

As shown in FIG. 36, the motor section 215 (refer to FIG. 7) of the motor unit 611 rotates according to the rotation instruction signal transmitted from the electric bending circuit section 35 (refer to FIG. 1). The rotation of this motor section 215 is transmitted to the output shaft 613 via the reduction gear section 217 (refer to FIG. 7), and the output shaft 613 rotates. Since the output shaft flat section 617 rotates as the output shaft 613 rotates, the main body observation hole flat section 653, which the output shaft flat section 617 contacts, is pushed; thus the connecting device body 642 rotates. As a result, the vertical direction pulley connecting section 643 of the connecting device body 642 rotates, which pushes the flat D hole section 567 that the pulley connecting flat section 644 contacts; thus the D hole 559, that is the pulley section 553, rotates.

At this time, since the rotation of the motor section 215 is detected by the encoder 219 (refer to FIG. 7), it means that the rotation of the output shaft 613, that is the rotation of the pulley section 553, is detected by the encoder 219 (refer to FIG. 7).

Next is a description of the horizontal bending direction.

By manipulating the joystick 62 (refer to FIG. 1) of the remote controller 6 (refer to FIG. 1) in a desired horizontal direction, a signal corresponding to the tilt angle of this joystick 62 (refer to FIG. 1) is transmitted to the electric bending circuit section 35 (refer to FIG. 1). Then, in this electric bending circuit section 35 (refer to FIG. 1), the rotation of the output shaft 614 corresponding to the control signal is calculated mathematically, and a rotation instruction signal corresponding to the calculated result is transmitted to the motor unit 612 as shown in FIG. 36.

As shown in FIG. 36, the motor section 216 (refer to FIG. 7) of the motor unit 612 rotates according to the rotation instruction signal transmitted from the electric bending circuit section 35 (refer to FIG. 1). The rotation of this motor section 216 (refer to FIG. 7) is transmitted to the output shaft 614 via the reduction gear section 218 (refer to FIG. 7), and the output shaft 614 rotates. Then, the first stage gear 461 connected to the output shaft 614 rotates as the output shaft 614 rotates, and the final stage gear 464 engaged with the first stage gear 461 rotates.

Then, the output sleeve 466 extending from this final stage gear 464 rotates.

Here, the output sleeve 466 is fitted together with and connected to the horizontal direction pulley connecting section 645 such that the output sleeve flat section 471 and the pulley connecting flat section 6 make contact. Therefore, the rotation of the final stage gear 464 is transmitted to the horizontal direction pulley connecting section 645 via the output sleeve 466.

At this time, although the final stage gear 464 is retained on the output shaft 613 via the balls 470, the balls 470 play a role as ball bearings, thus the final stage gear 464 is not influenced by the rotation of the output shaft 613. Furthermore, the final stage gear 464 is connected with the first stage gear 461 and the reduction gear section 218 (refer to FIG. 7). Therefore, although the transmitted driving force must be higher than a certain amount in order for the output shaft 613 to rotate the final stage gear 464, the first stage gear 461, and the reduction gear section 218, the driving force cannot be transmitted due to the loss of driving force at the balls 470.

Since the flat D hole section 568, which contacts the pulley connecting flat section 646 of the horizontal direction pulley connecting section 645, rotates, the D hole 560, that is the pulley section 554, rotates in synchronization with the rotation of the final stage gear 464.

Accordingly, the motor section 216 (refer to FIG. 7) of the motor unit 612 rotates the pulley section 554.

At this time, since the rotation of the motor section 216 (refer to FIG. 7) of the motor unit 612 is detected by the encoder 220 (refer to FIG. 7), it means that the rotation of the output shaft 614, that is the rotation of the pulley section 554, is detected by the encoder 220 (refer to FIG. 7).

By combining the operations of the vertical direction and the horizontal direction in this manner, when the joystick 62 (refer to FIG. 1) is manipulated, the bending section 23 (refer to FIG. 1) is bent and the tip section body 22 (refer to FIG. 1) is pointed in a desired direction at the time of examination so that an object can be observed.

As a device for allowing sliding between the output shaft 613 and the output sleeve 466, instead of the above-described balls 470, a lubricant or the like may be coated on the output shaft 613 and the output sleeve 466.

Furthermore, both may be formed using a metal powder injection molding process, and the porosities created in the powder at the time of molding may be impregnated with oil to improve lubricity.

(Effects)

Using the second embodiment, it is possible to transmit the driving force from the output shafts 613 and 614 of the motor units 611 and 612 of the drive unit 434 to the pulley sections 553 and 554 efficiently by the connecting device 641; thus it is possible to obtain the same effects as the first embodiment.

THIRD EMBODIMENT

Figure 37:
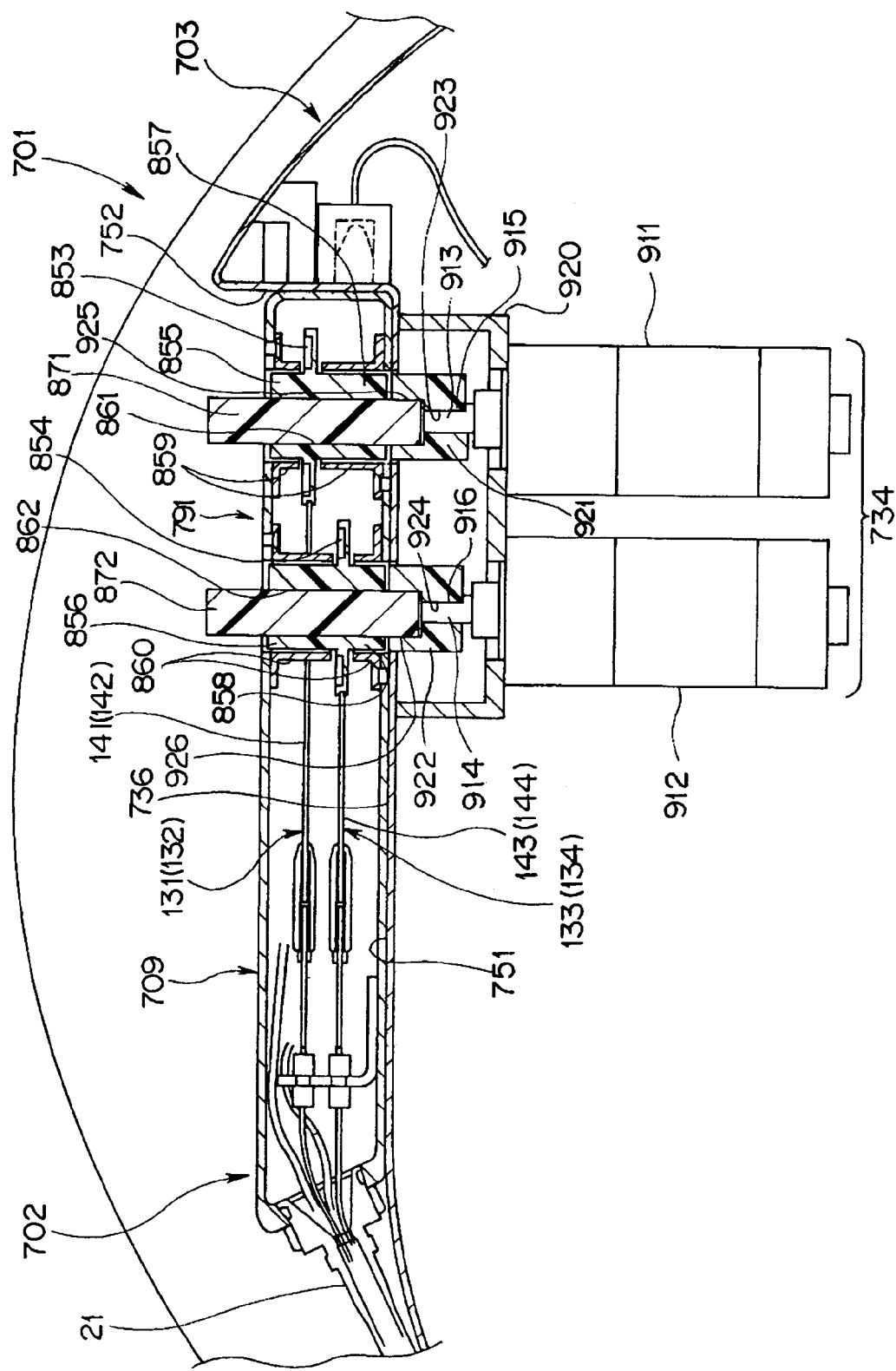
FIG. 37 is a cross-sectional diagram of a drum section, according to a third embodiment of the present invention.
Figure 38:
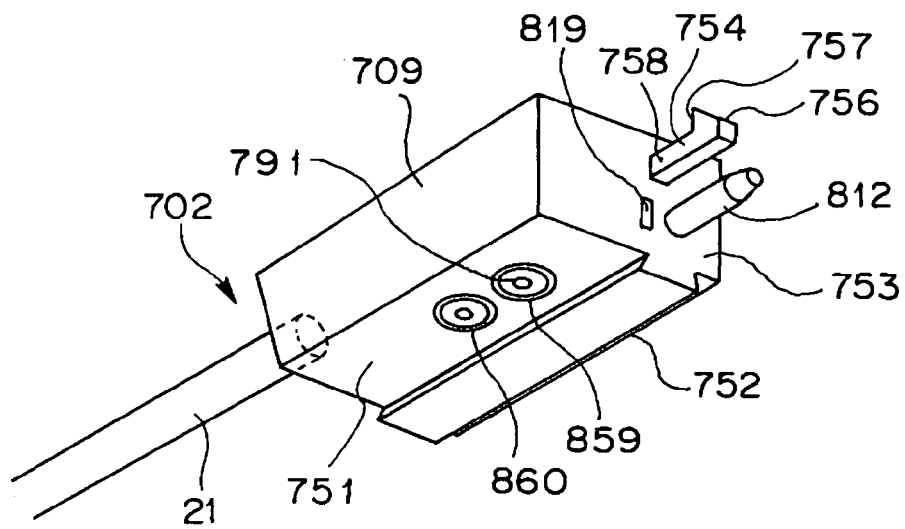
FIG. 38 is a perspective view of a connector section according to the third embodiment of the present invention.
Figure 39:
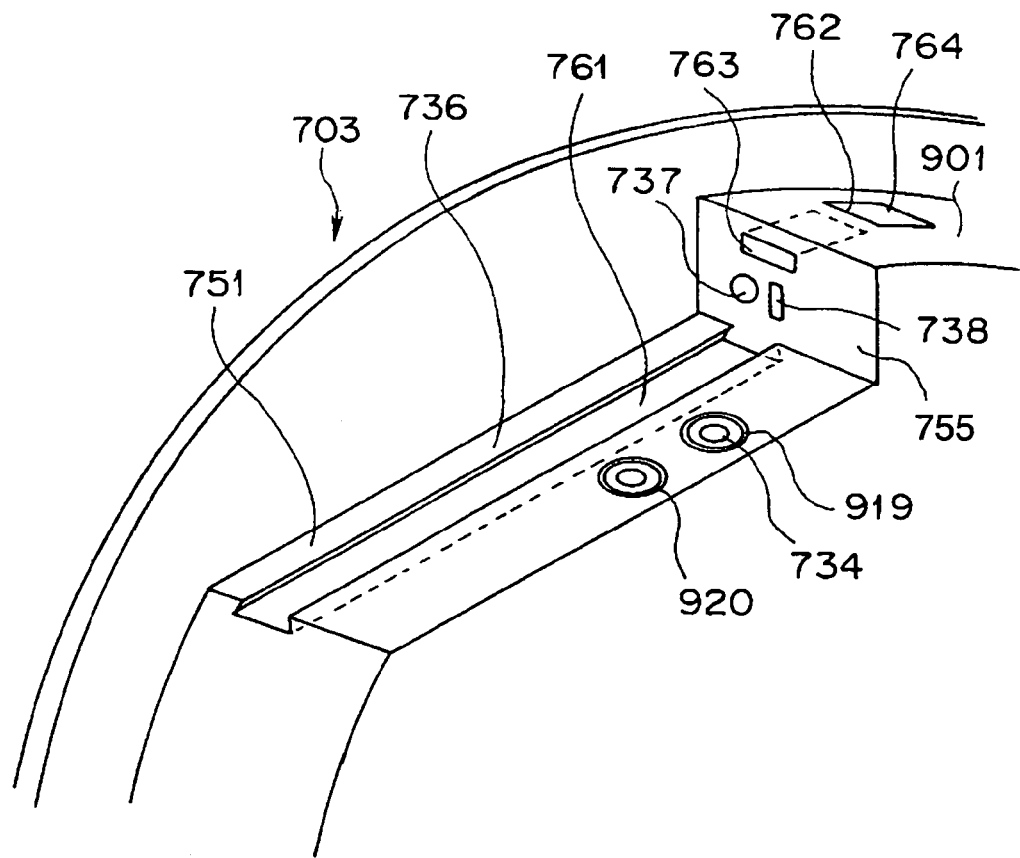
FIG. 39 is a perspective view of a connector installation section according to the third embodiment of the present invention.
Figure 40:
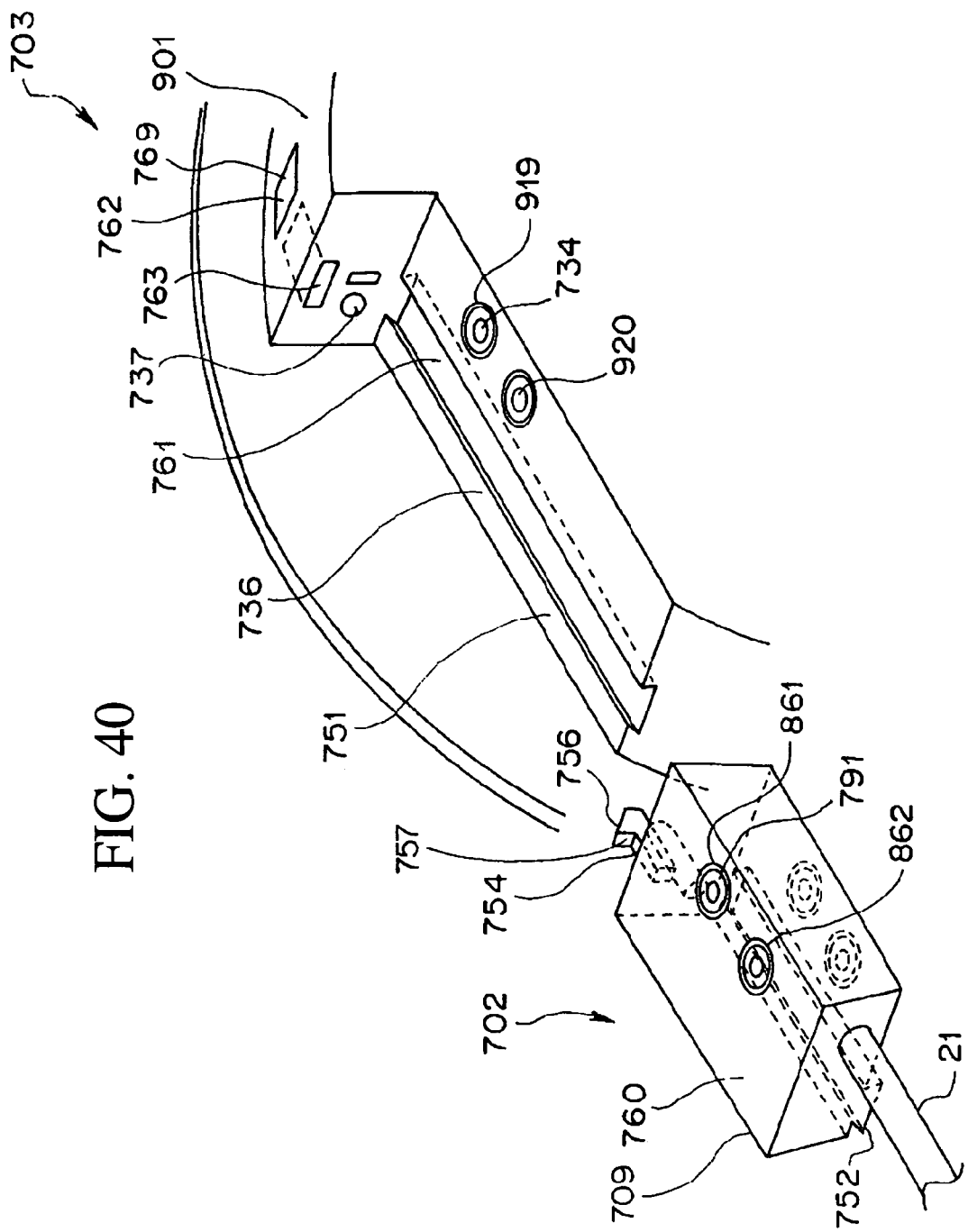
FIG. 40 is a perspective view in a state before the connector section is installed in the connector installation section, according to the third embodiment of the present invention.
Figure 41:
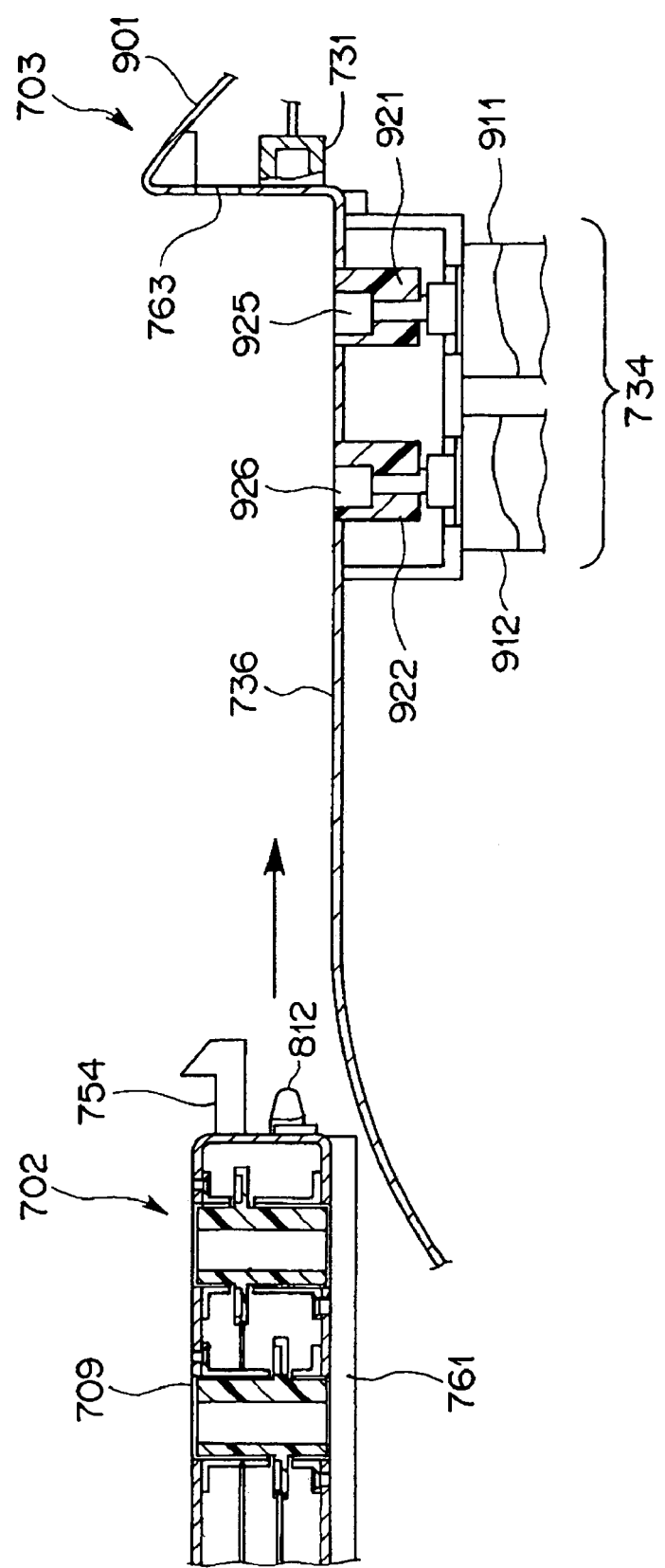
FIG. 41 is a partially enlarged diagram of the main parts in a state before the connector section is installed in the connector installation section, according to the third embodiment of the present invention.
Figure 42:
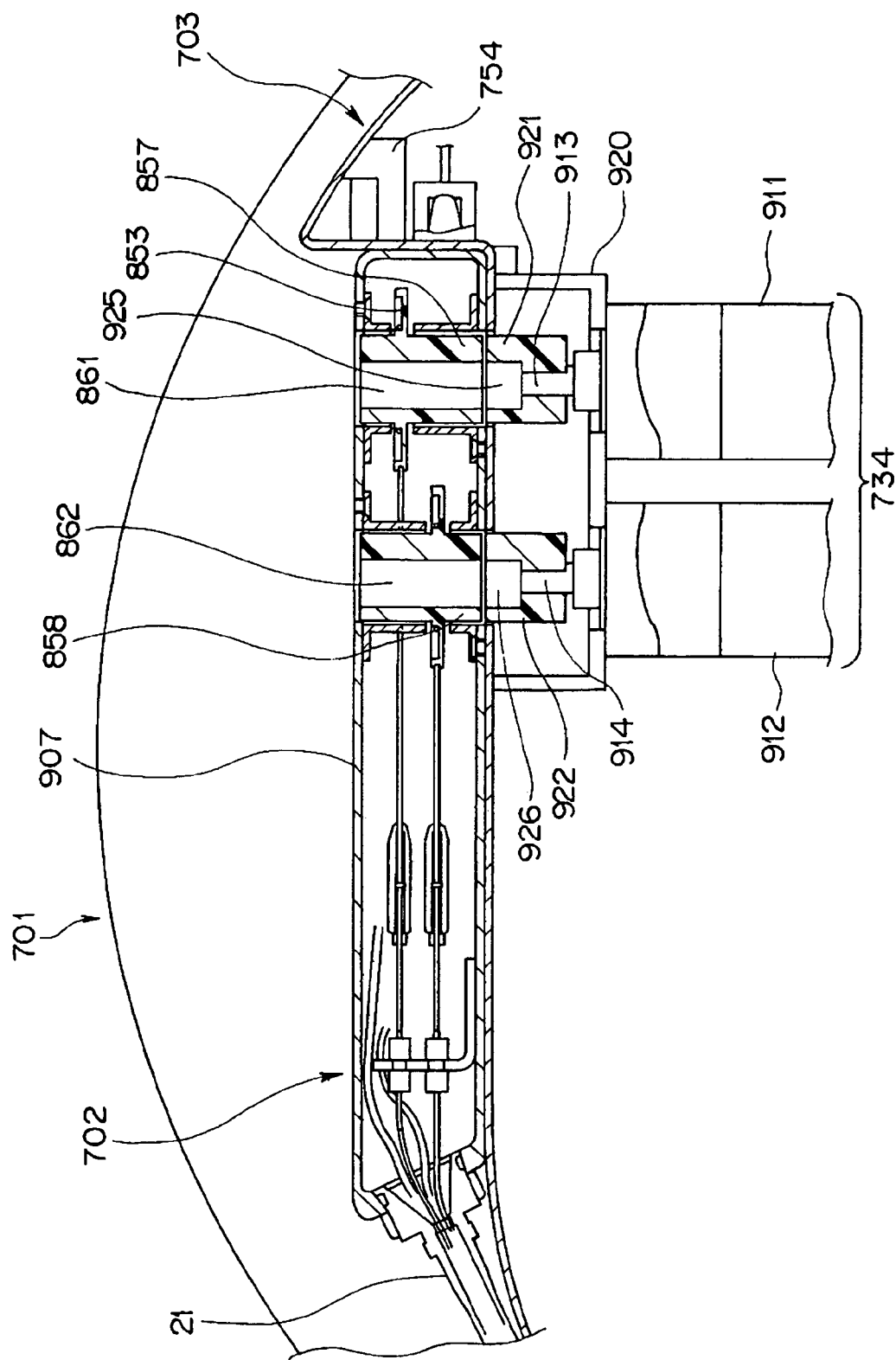
FIG. 42 is a partially enlarged diagram of the main parts in a state before a connecting device is installed in a pulley section, according to the third embodiment of the present invention.
Figure 43:
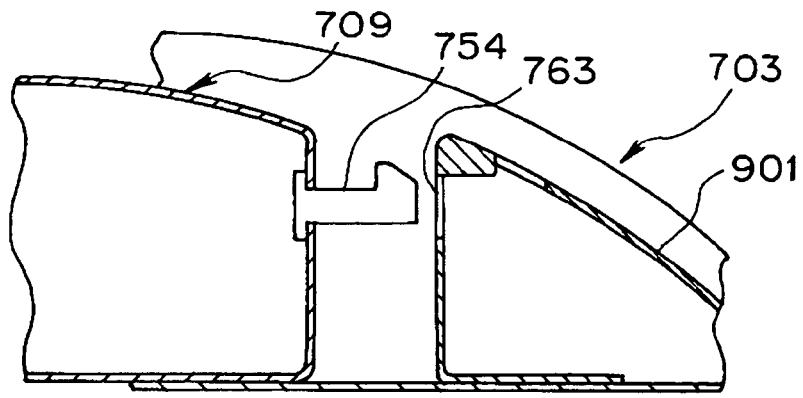
FIG. 43 is a first cross-sectional diagram showing the structure whereby the connector section is fixed in the connector installation section, according to the third embodiment of the present invention.
Figure 44:
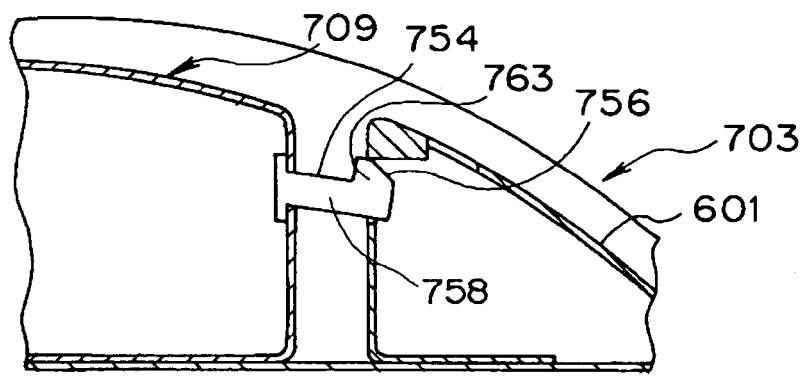
FIG. 44 is a second cross-sectional diagram showing the structure whereby the connector section is fixed in the connector installation section, according to the third embodiment of the present invention.
Figure 45:
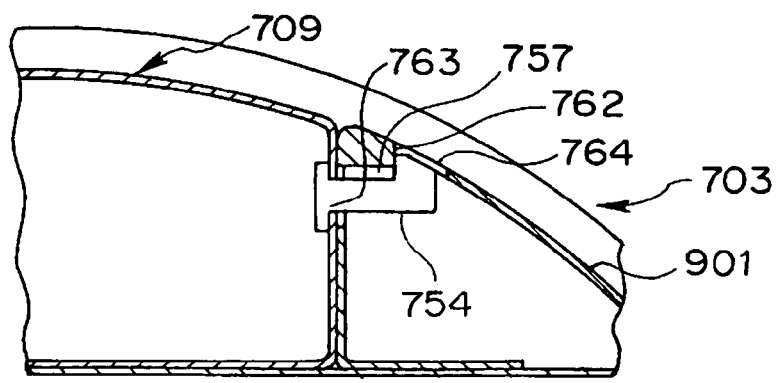
FIG. 45 is a third cross-sectional diagram showing the structure whereby the connector section is fixed in the connector installation section, according to the third embodiment of the present invention.
Figure 46:
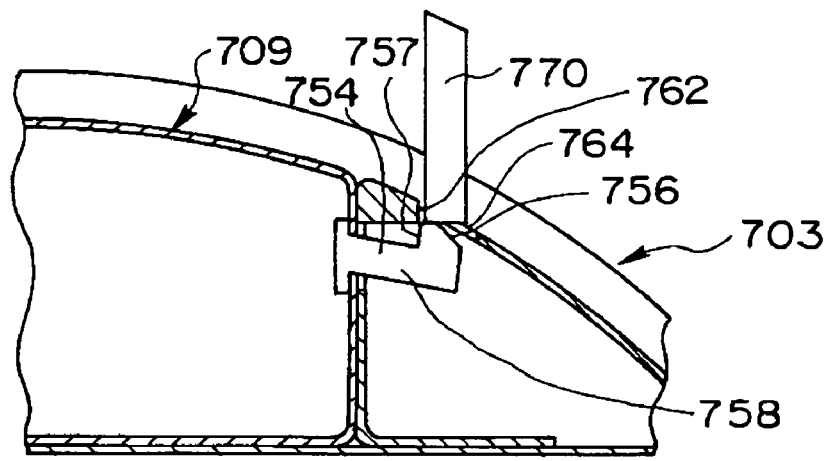
FIG. 46 is a cross-sectional diagram showing the structure whereby the connector installation section and the connector section are separated, according to the third embodiment of the present invention.

FIG. 37 through FIG. 46 are diagrams associated with a third embodiment of the present invention. FIG. 37 is a cross-sectional diagram showing a drum section and a connector section. FIG. 38 is a perspective view of the connector section. FIG. 39 is a perspective view of a connector installation section. FIG. 40 is a perspective view in a state before the connector section is installed in the connector installation section. FIG. 41 is a partially enlarged diagram of the main parts in a state before the connector section is installed in the connector installation section. FIG. 42 is a partially enlarged diagram of the main parts in a state before a connecting device is installed in a pulley section. FIG. 43 is a first cross-sectional diagram showing the structure whereby the connector section is installed in the connector installation section. FIG. 44 is a second cross-sectional diagram showing the structure whereby the connector section is installed in the connector installation section. FIG. 45 is a third cross-sectional diagram showing the structure whereby the connector section is installed in the connector installation section. FIG. 46 is a cross-sectional diagram showing the structure whereby the connector installation section and the connector section are separated.

Here, the same symbols are used for structures with the same operations and effects as in the above-described first embodiment, and the descriptions are omitted.

(Construction)

As shown in FIG. 37, in an endoscope apparatus 701 of the third embodiment, a connector installation section 736 is installed in a part of a drum section 703, in the form of a notch similarly to the first embodiment. The base end section of an industrial endoscope 702 has a connector section 709, which is to be installed in the connector installation section 736.

The connector installation section 736 has a flat installation face 751 and an installation wall 755.

As shown in FIG. 38, the bottom face 751 of this connector section 709 contains a slide section 752 that engages in a slide slot 761 provided in the flat installation face 751 of the connector installation section 736 as shown in FIG. 39. Furthermore, the base end face 753 of the connector section 709 has a latch 754 that latches in a latch section 762 as described later.

This latch 754 has a sloping section 756, a wall section 757, and a bar section 758.

As shown in FIG. 38, the sloping section 756 forms a slope at the end of the hook section 754, and guides the latch 754 to be inserted in an engagement window 763 as shown in FIG. 40.

As shown in 38, the wall section 757 of the latch 754 latches in the latch section 762 of the latch 754 shown in FIG. 39.

As shown in 38, the bar section 758 acts as a cantilever to support the sloping section 756 and the wall section 757.

The latch 754 may be formed from a metal such as stainless steel or aluminum, formed from a resin such as ABS, PMMA, or PC, or formed from a soft resin such as urethane, vinyl chloride, or the like, in one piece.

Furthermore, the bar section 758, the sloping section 756, and the wall section 757 of the latch 754 may be formed from different materials.

As shown in FIG. 38, a light guide connector 812 and a male image connector 819 are arranged on the base end face 753 of the connector section 709. Connector side apertures 859 and 860, and a pulling apparatus 791, part of which can be observed from the connector side apertures, are arranged on the bottom face 751 of the connector section 709.

As shown in FIG. 40, connector side apertures 861 and 862 are formed on the top face 760 of this connector section 709. The pulling apparatus 791 can be observed from the connector side apertures 861 and 862.

As shown in FIG. 39, the slide slot 761 and drum side apertures 919 and 920, inside of which a drive unit 734 is arranged, are provided on the flat installation face 751 of the connector installation section 736.

The installation wall 755 of the connector installation section 736 is provided with a light guide connector receiving section 737 to be assembled with the light guide connector 812 shown in FIG. 38, a female image connector 738 to be assembled with the male image connector 819, and the engagement window 763 in which the latch 754 shown in FIG. 38 is inserted. A latch section 762 is provided at the back of the engagement window 763, in which the latch 754 engages when it is inserted.

Furthermore, a disengagement window 764 is provided near the latch section 762 of a tubular element 901, which enables the latch 754 latched in the latch section 762 to be pressed in order to disengage it.

Next is a description of the drive unit 734 and the pulling apparatus 791.

Here, the driving mechanism and the pulling mechanism of the vertical and horizontal directions of the present invention have the same structures as in the first and second embodiments. Therefore, they are omitted here, and only the vertical direction will be described.

As shown in FIG. 37, in the drum section 703, motor units 911 and 912 are retained by a motor unit retaining frame 920, forming a drive unit 734. Rotors 921 and 922 are installed in output shafts 913 and 914 of the motor units 911 and 912. The rotors 921 and 922 have output shaft installation holes 923 and 924, which contact output shaft flat surface sections 915 and 916 of the output shafts 913 and 914, and fit together with them.

Furthermore, the connector section 709 is provided with pulley sections 853 and 854 onto which pulling apparatus side wires 141, 142, 143 and 144 are wound, forming the pulling apparatus 791.

The pulley section 853 is supported in a bearing section 859 by hub sections 855 and 857, which protrude from both of its faces, such that it can rotate.

The pulley section 854 is supported in a bearing section 860 by hub sections 856 and 858, which protrude from both of its faces, such that it can rotate.

The pulley sections 853 and 854 have pulley section D holes 861 and 862, which face the rotors 921 and 922 respectively, have the same sizes as the rotor D hole sections 925 and 926, and pass through the pulley sections 853 and 854.

Separate from the pulley sections 853 and 854 and the rotors 921 and 922, are connecting rods 871 and 872, whose cross sections are D holes shaped, and act as rods to fit in the rotor D holes 925 and 926 and the pulley section D holes 861 and 862.

(Operation of the Invention)

Hereunder is a description of the operation of the third embodiment.

In the case where the industrial endoscope 702 is connected to the drum section 703, as shown in FIG. 40, the direction of the slide section 752 is aligned with the direction of the slide slot 761, and the connector section 709 is slid forward toward the slide section 752 and the slide slot 761 engaged.

Then, the latch 754 moves towards the engagement window as shown in FIG. 41, and the latch 754 approaches the engagement window 763 as shown in FIG. 43. The light guide connector 812 is inserted into the light guide connector receiving section 737, which is omitted in FIG. 43, and the sloping section 756 makes contact with the engagement window 763 as shown in FIG. 44. Then, the bar section 758 is deformed elastically by the pressure due to the connector section 709 being slid forward, and furthermore the latch 754 is inserted into the deep part through the engagement window 763. Then, as shown in FIG. 45, the wall section 757 is engaged with the latch section 762, completing the engagement of the latch 754 and the latch section 762.

Then, as shown in FIG. 42, the hub 857 of the pulley section 853 sits over the top of the rotor 921, and the hub 858 of the pulley section 854 sits over the top of the rotor 922.

As shown in FIG. 37, the connecting rod 871 is inserted into the pulley section D hole 861 and the rotor D hole 923, and the connecting rod 872 is inserted into the pulley section D hole 862 and the rotor D hole 924.

In this state, the connection of the drive unit 734 and the pulling apparatus 791 is complete.

Bending operations as described in the first embodiment are performed in this state.

Next, in order to remove the industrial endoscope 702, after removing the connecting rods 871 and 872, a finger or a bar shaped tool 770 is inserted to press the sloping section 756 as shown in FIG. 46. The bar section 758 is deformed elastically, and the latch section 762 and the wall section 757 are disengaged.

In this state, if the connector section 709 is withdrawn along the direction of engagement of the slide slot 761 of the slide section 752 as shown in FIG. 40, the connector section 709 and the connector installation section 736 are disengaged.

Here, the cross sections of the slide section 752 and the slide slot 761 shown in FIG. 40 are trapezoidal, so the two can only be disengaged in the sliding direction.

(Effects)

According to the third embodiment as described above, the same effects as the first embodiment can be obtained. Furthermore, since the connector section 709 and the connector installation section 736 are assembled not by rotational fixing using fixing knobs, but by linear engagement of the slide section 752 with the slide slot 761, there is an effect of making a simple fixing operation.

Moreover, in the third embodiment, the direction of installation of the connecting section 709 is different from the first embodiment, in that it slides in the horizontal direction. Accordingly, it is possible to check the completion of the connection of the light guide connector 812 and the light guide connector receiving section 737, and the connection of the male image connector 819 and the female image connector 738, by visual observation from above. Therefore, there is an effect that the connector section 709 can be fixed reliably.

In the present embodiment, since the surfaces on which the drive unit 734 and the pulling apparatus 791 are installed do not have protruding shafts and holes, but holes which do not protrude, the connection surfaces are flat. Therefore there is no limitation caused by the direction of shafts protruding, so the connector installation section 736 and the connector section 709 can be assembled in any direction.

Figure 47:
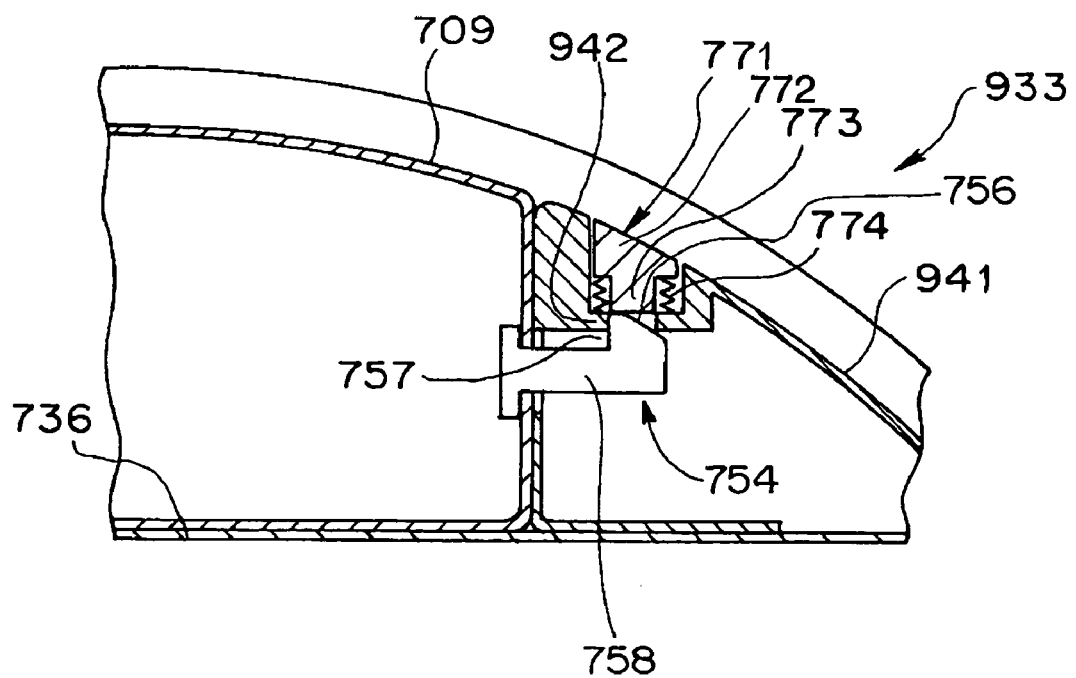
FIG. 47 is a cross-sectional diagram of a drum section showing a modified example of the third embodiment of the present invention.

FIG. 47 is a cross-sectional diagram of a drum section showing a modified example of the third embodiment.

As shown in FIG. 47, a switch 771 is provided near a latch section 942 for pressing the latch 754 latched in the latch section 942 of a tube shaped member 941 of a drum section 933.

A foot section 773 of the switch 771 presses the sloping section 756 of the latch 754 by a push section 772 being pressed. When the pressing of the push section 772 is discontinued, the spring 774 returns the foot section of the switch 771 to its initial state.

According to the modified example as described above, by pressing the push section 772, the latch 754 is removed from the latch section 942, and the connector section 709 can be removed from the connector installation section 736. In the case of this modified example, the tool 770 or the like as shown in FIG. 46 is not required, so there is an effect that the operation is simplified.

Figure 48:
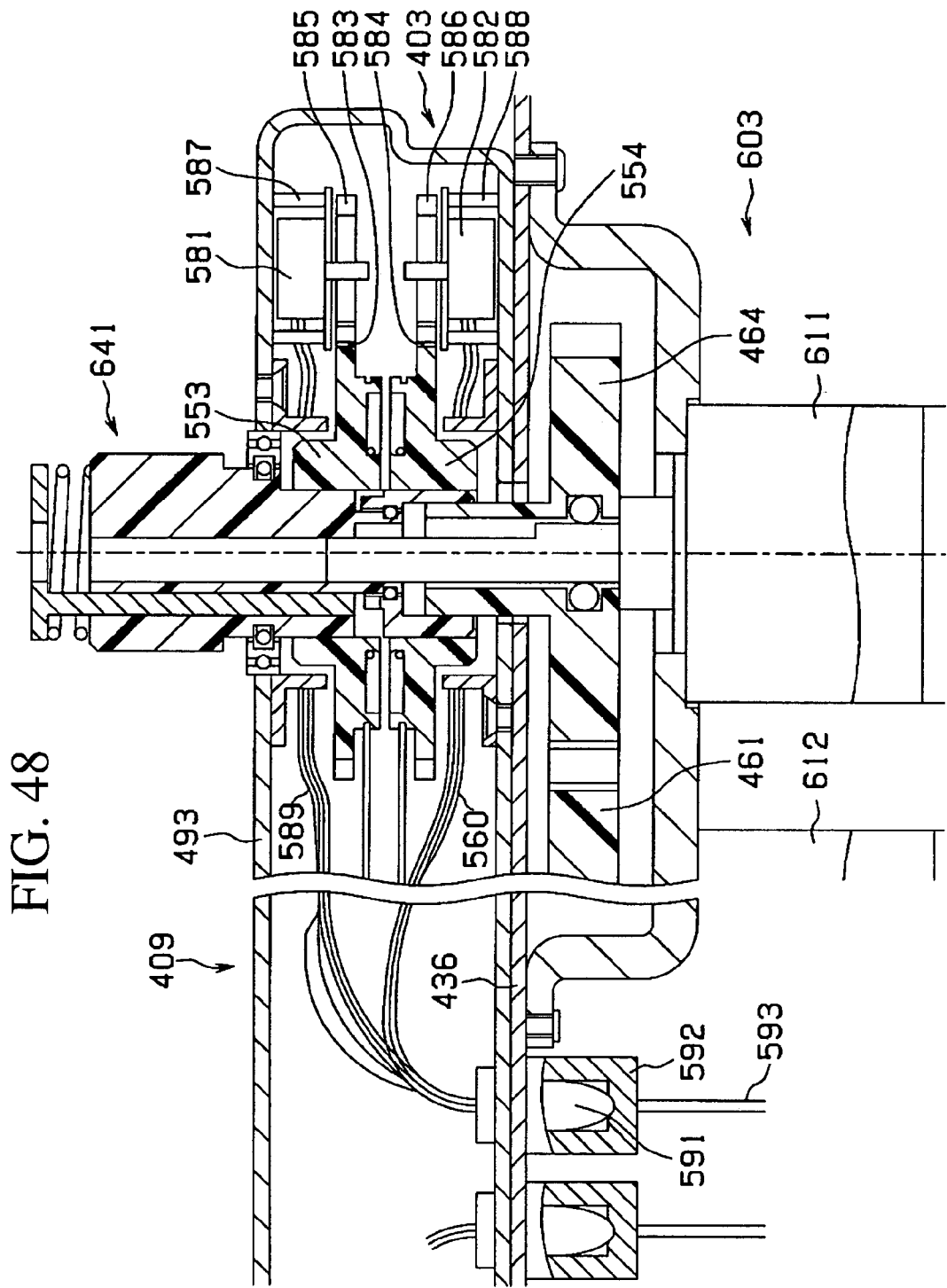
FIG. 48 is an explanatory diagram showing another example of a rotary position detecting device of the second embodiment of the present invention.

FIG. 48 is an explanatory diagram showing another example of a rotary position detecting device of the second embodiment.

In the second embodiment shown in FIG. 21 through FIG. 36, the encoders 219 and 220 are installed directly in the motor units 611 and 612 as rotary position detecting devices. However, potentiometers 581 and 582 may be provided on the connector section 409 side such that they operate together with the pulley sections 553 and 554 as rotary position detecting devices as shown in FIG. 48. In this case, the potentiometers 581 and 582 may be assembled onto the pulley sections 553 and 554 and the output shafts 613 and 614 directly. Furthermore, as shown in FIG. 48, pulley gear sections 583 and 584 may be provided in the pulley sections 553 and 554, and potentiometer gear sections 585 and 586, which engage with the pulley gear sections 583 and 584, may be fixed onto the rotating shafts of the potentiometers 581 and 582. In this case, the potentiometers 581 and 582 are fixed by supporting elements 587 and 588.

In either example, in the case where the potentiometers 581 and 582 are provided on the connector section 409, relay cables 589 and 590 extending from the terminals of the potentiometers 581 and 582 respectively are connected to a male potentiometer connector 591 provided in a connector case 492. In the connector installation section 436, a female potentiometer connector 592 is provided to be connected with the male potentiometer connector 591, and the female potentiometer connector 592 and the electric bending circuit section 35 (refer to FIG. 4) may be connected via a relay cable 593.

In this case, if the connector section 409 and the connector installation section 436 are connected, the electric bending circuit section 35 can always monitor the position information of the potentiometers 581 and 582; thus it can be used to perform bending control.

Here, encoders may be provided on the connector section 709 side instead of the potentiometers 581 and 582.

In the first and the third embodiments, it is also possible to use the potentiometers 581 and 582 as the rotary position detecting devices as shown in FIG. 48.

Furthermore, in the first through the third embodiments, the insertion section side wires 135, 136, 137 and 138 may be wound onto the two pulley sections directly without providing the pulling apparatus side wires 141, 142, 143 and 144.

Figure 49:
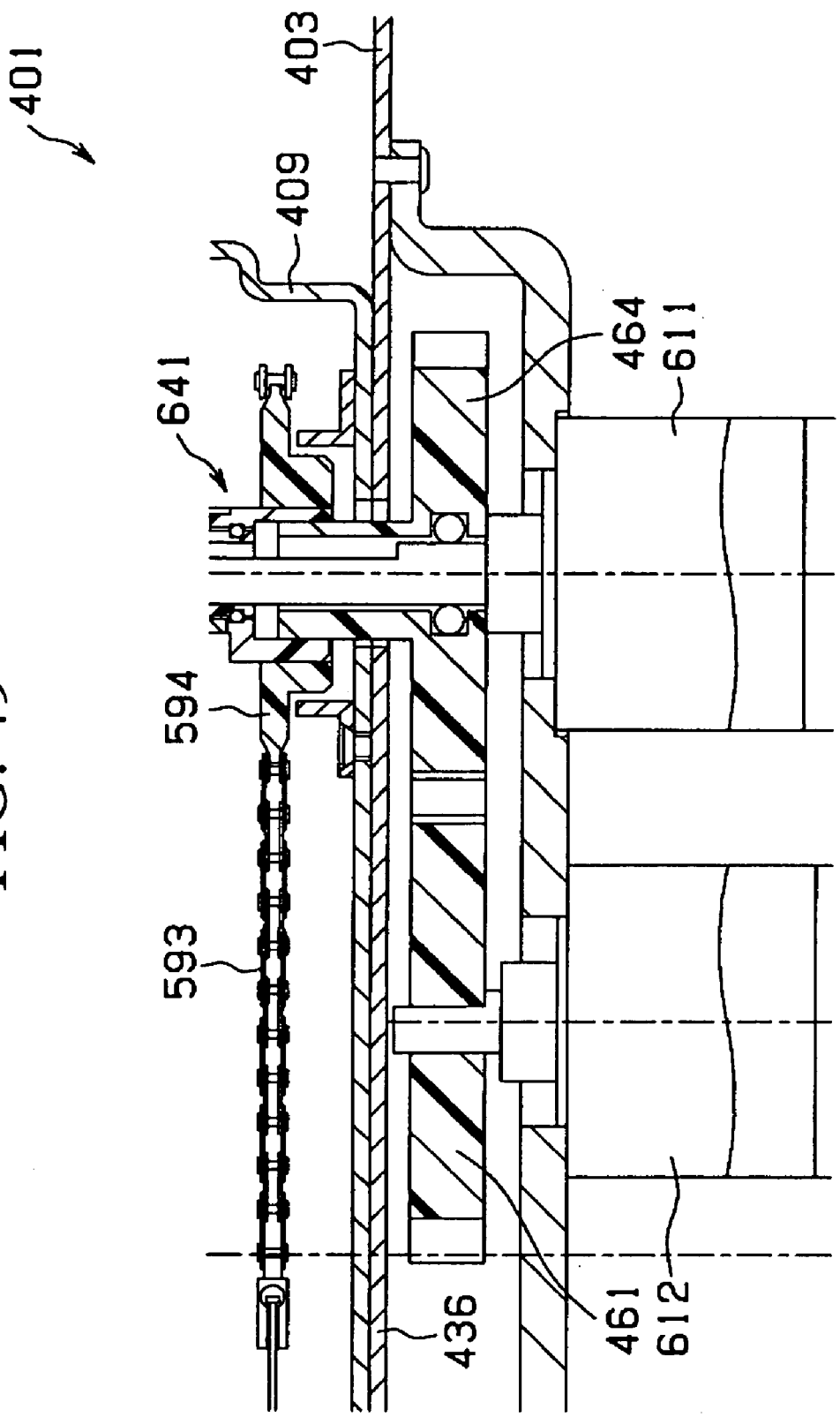
FIG. 49 is an explanatory diagram for the case where a chain is used instead of pulling apparatus side wires of the second embodiment of the present invention.

FIG. 49 is an explanatory diagram for the case where a chain is used instead of the pulling apparatus side wires of the second embodiment.

In the second embodiment, instead of the pulling apparatus side wires 141, 142, 143 and 144 shown in FIG. 21, there is no change to the effects if a chain 593 or a belt is used as shown in FIG. 49, rather than wires, and a sprocket 594 is used as shown in FIG. 49 instead of the pulley sections 553 and 554 shown in FIG. 21.

Moreover, the chain 593 shown in FIG. 49, or belt, may also be used in the first and the third embodiments.

Figure 50:
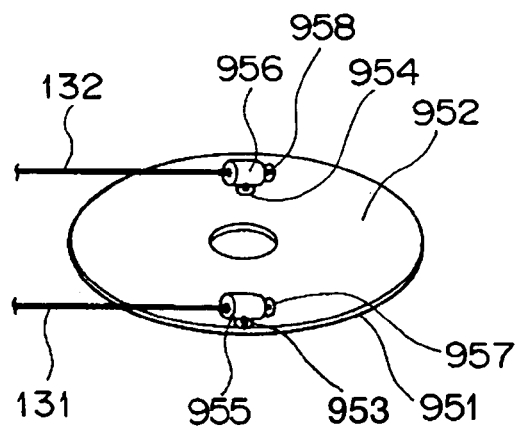
FIG. 50 is a perspective view of a pulley section and pulling apparatus side wires, in a state in which the bending section is not bent, showing another example of a first connection structure of the pulley section and the bending control wires shown in FIG. 1 through FIG. 47.
Figure 51:
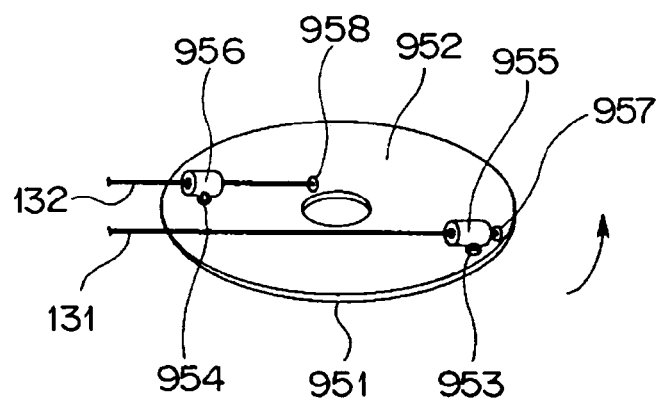
FIG. 51 is a perspective view of the pulley section and the pulling apparatus side wires in a state in which the bending section is bent, showing another example of the first connection structure of the pulley section and the bending control wires shown in FIG. 1 through FIG. 47.
Figure 52:
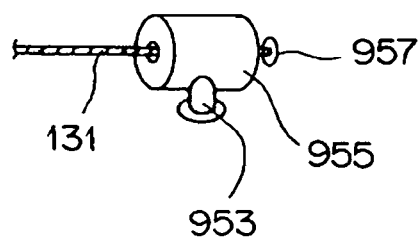
FIG. 52 is an enlarged diagram of a rotating retainer of FIG. 51 and the surrounding area.

FIG. 50 through FIG. 52 are diagrams showing another example of the first connection structure of the pulley section and the bending control wires shown in FIG. 1 through FIG. 47. FIG. 50 is a perspective view of a pulley section and pulling apparatus side wires, in a state in which the bending section is not bent. FIG. 51 is a perspective view of the pulley section and the pulling apparatus side wires in a state in which the bending section is bent. FIG. 52 is an enlarged diagram of a rotating retainer and the surrounding area.

As shown in FIG. 50 through FIG. 52, a pulley 951 can be used as a substitute for the pulley sections 153, 154, 553, 554, 853 and 854 shown in FIG. 1 through FIG. 47.

Holding shafts 953 and 954 are provided in locations at the left and right of the surface 952 of the pulley 951. The holding shafts 953 and 954 hold rotating retainers 955 and 956 such that they can rotate freely. Bending control wires 131 and 132 are inserted through the rotating retainers 955 and 956 respectively. Metal fasteners 957 and 958 are provided at the ends of the bending control wires 131 and 132 respectively, and prevent the bending control wires 131 and 132 from passing through the rotating retainers 955 and 956. In this manner, the pulley 951 performs bending operations of the bending control wires 131 and 132.

In the case of this structure, the bending control wires 131 and 132 do not bend around the pulley 951; the rotating retainers 955 and 956 rotate instead. Therefore, as shown in FIG. 51, the bending control wires 131 and 132 do not get damaged due to repetitive bending, so there is an effect of improving the resistance to fatigue of the bending control wires 131 and 132.

Figure 53:
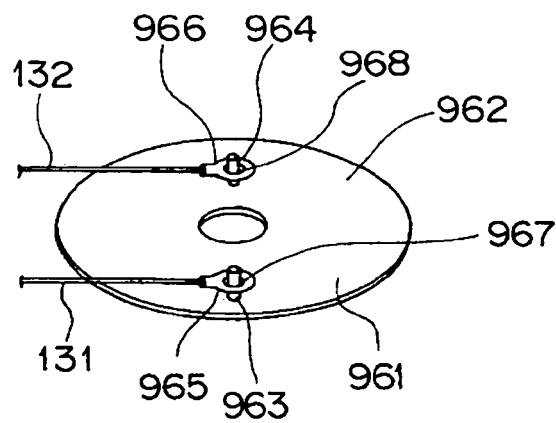
FIG. 53 is a perspective view of a pulley section and pulling apparatus side wires, in a state in which the bending section is not bent, showing another example of a second connection structure of the pulley section and the bending control wires shown in FIG. 1 through FIG. 47.
Figure 54:
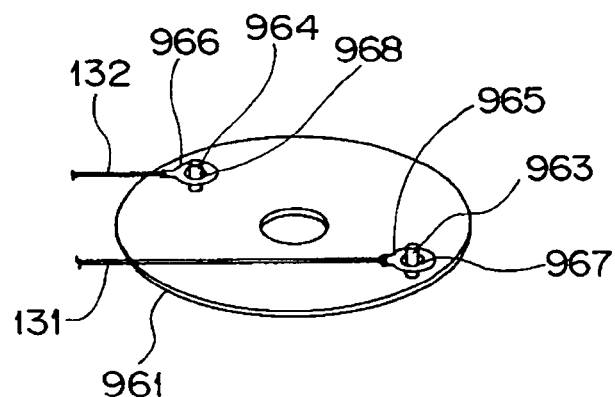
FIG. 54 is a perspective view of a pulley section and pulling apparatus side wires, in a state in which the bending section is bent, showing another example of the second connection structure of the pulley section and the bending control wires shown in FIG. 1 through FIG. 47.
Figure 55:
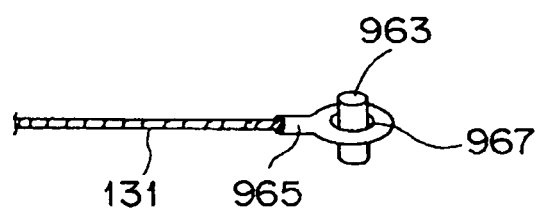
FIG. 55 is an enlarged diagram of a supporting ring of FIG. 53 and the surrounding area.

FIG. 53 through FIG. 55 are diagrams showing another example of a second connection structure of the pulley section and the bending control wires shown in FIG. 1 through FIG. 47. FIG. 53 is a perspective view of a pulley section and pulling apparatus side wires, in a state in which the bending section is not bent. FIG. 54 is a perspective view of the pulley section and the pulling apparatus side wires in a state in which the bending section is bent. FIG. 55 is an enlarged diagram of a supporting ring and the surrounding area.

As shown in FIG. 53 through FIG. 55, a pulley 961 can be used as a substitute for the pulley sections 153, 154, 553, 554, 853 and 854 shown in FIG. 1 through FIG. 47.

Holding shafts 963 and 964 are provided in locations at the left and right of the surface 962 of the pulley 961. The bending control wires 131 and 132 are provided with support rings 965 and 966 respectively. The support rings 965 and 966 contain holes 967 and 968 respectively. The holes 967 and 968 of the support rings 965 and 966 fit onto the holding shafts 963 and 964 provided on the pulley 961 such that they can rotate freely.

In such a structure, it is also possible to obtain the same effects as in the connecting structure shown in FIG. 50 through FIG. 52.

Figure 56:
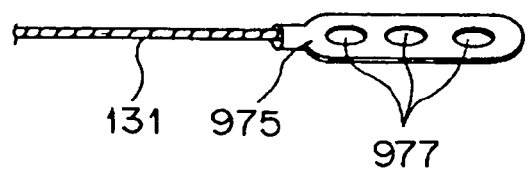
FIG. 56 is a perspective view showing another structure of the supporting ring shown in FIG. 53 through FIG. 55.

FIG. 56 is a perspective view showing another structure of the support rings shown in FIG. 53 through FIG. 55.

As shown in FIG. 56, a plurality of holes 977 may be provided in the support ring 975, so that any hole 977 that fits the holding shaft 963 shown in FIG. 53 through FIG. 55 can be selected from among them.

According to the structure of FIG. 56, there is an effect in that in the case where the bending control wire 131 is stretched due to fatigue, the deterioration in response due to the stretch of the bending control wire 131 can be countered by moving to another hole 977 so as to take up the stretch.

FOURTH EMBODIMENT

Figure 57:
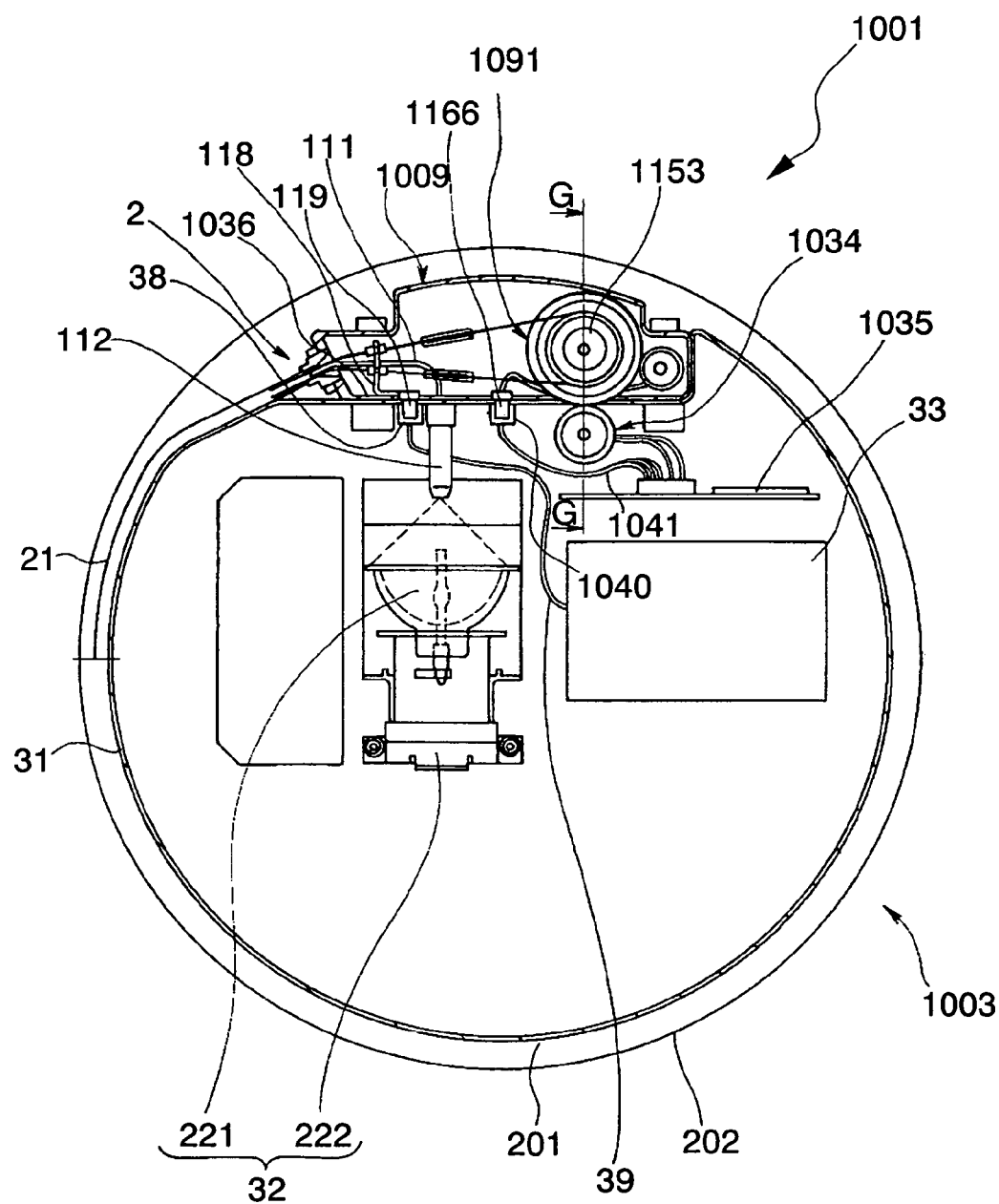
FIG. 57 is a cross-sectional diagram of a drum section, according to the fourth embodiment of the present invention.
Figure 58:
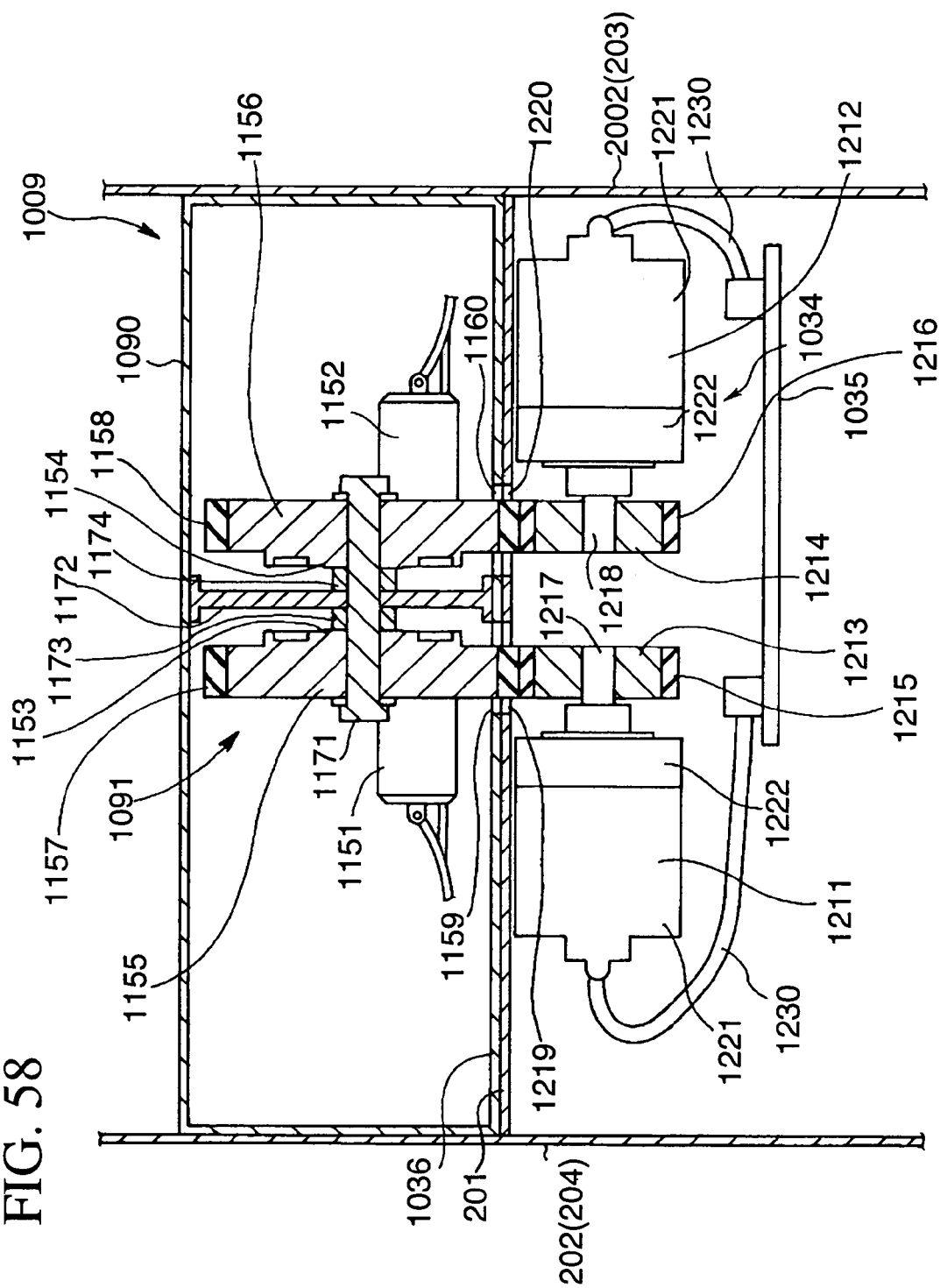
FIG. 58 is an enlarged cross-sectional diagram through line G-G of FIG. 57, according to the fourth embodiment of the present invention.
Figure 59:
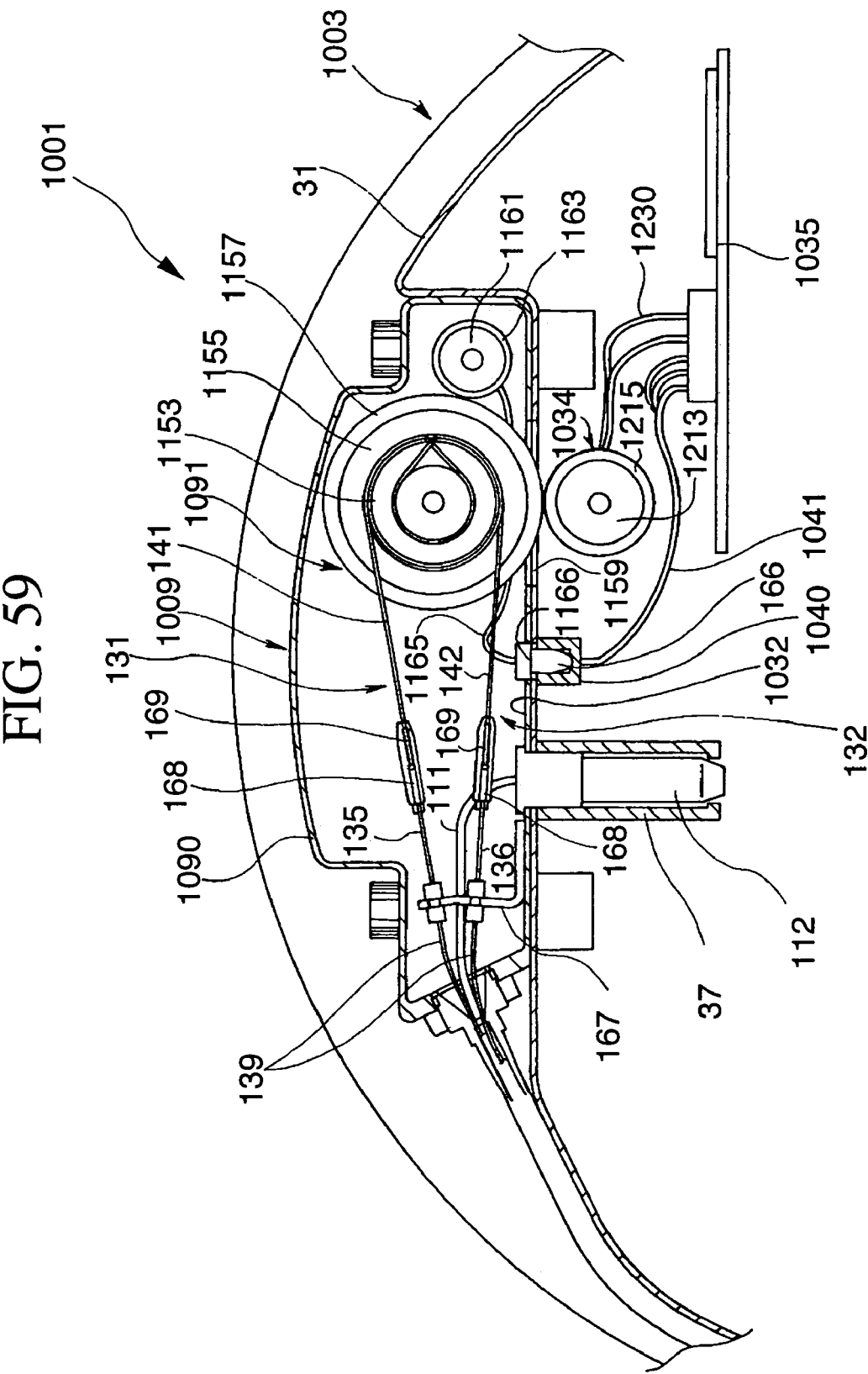
FIG. 59 is an enlarged diagram of a drive unit and a pulling apparatus, according to the fourth embodiment of the present invention.
Figure 60:
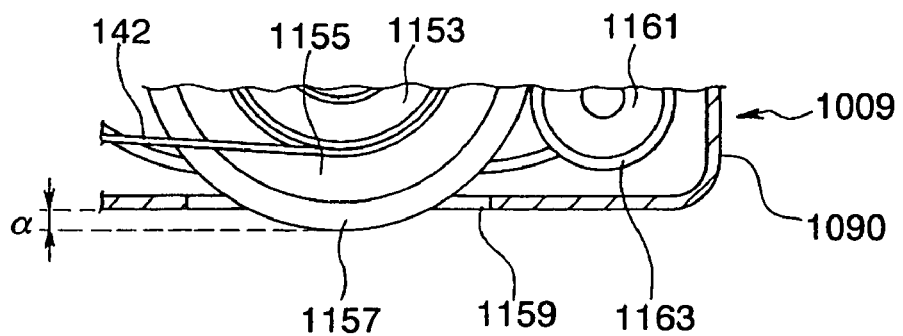
FIG. 60 is a partially enlarged diagram of the main parts of a connector section, according to the fourth embodiment of the present invention.
Figure 61:
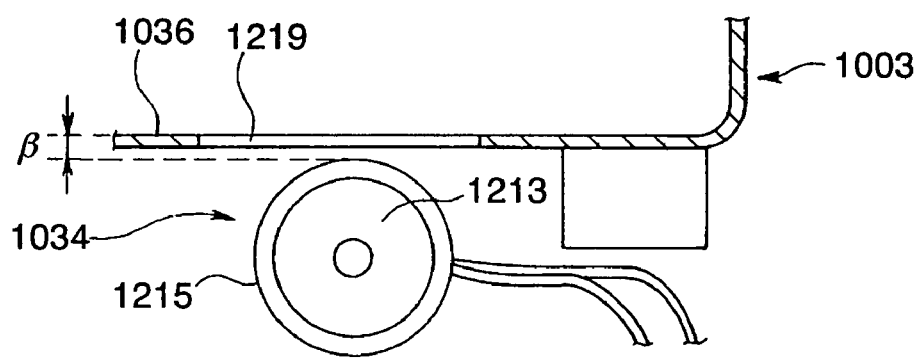
FIG. 61 is a partially enlarged diagram of the main parts of a connector installation section, according to the fourth embodiment of the present invention.
Figure 62:
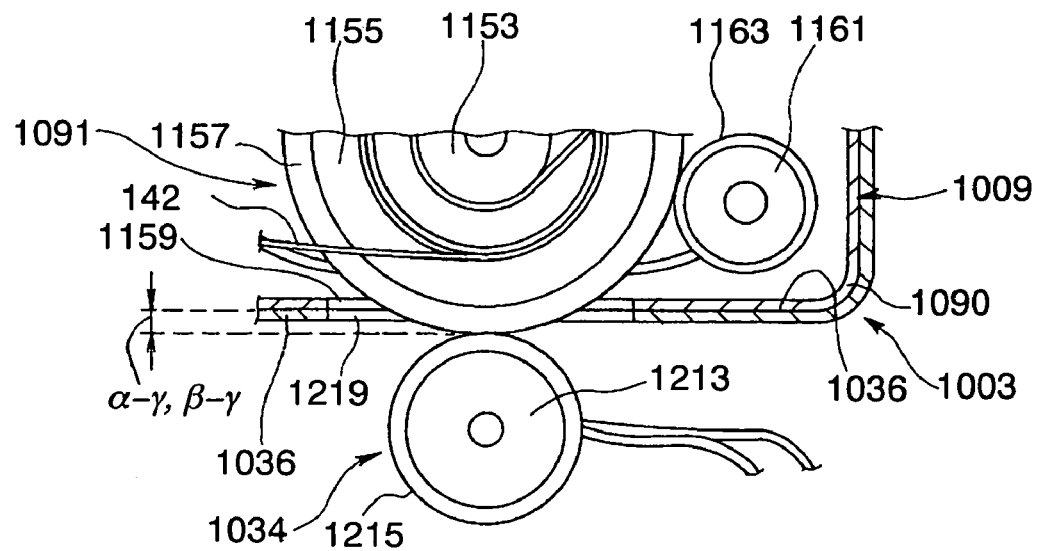
FIG. 62 is a partially enlarged diagram of the main parts in a state in which the connector section is installed in the connector installation section, according to the fourth embodiment of the present invention.
Figure 63:
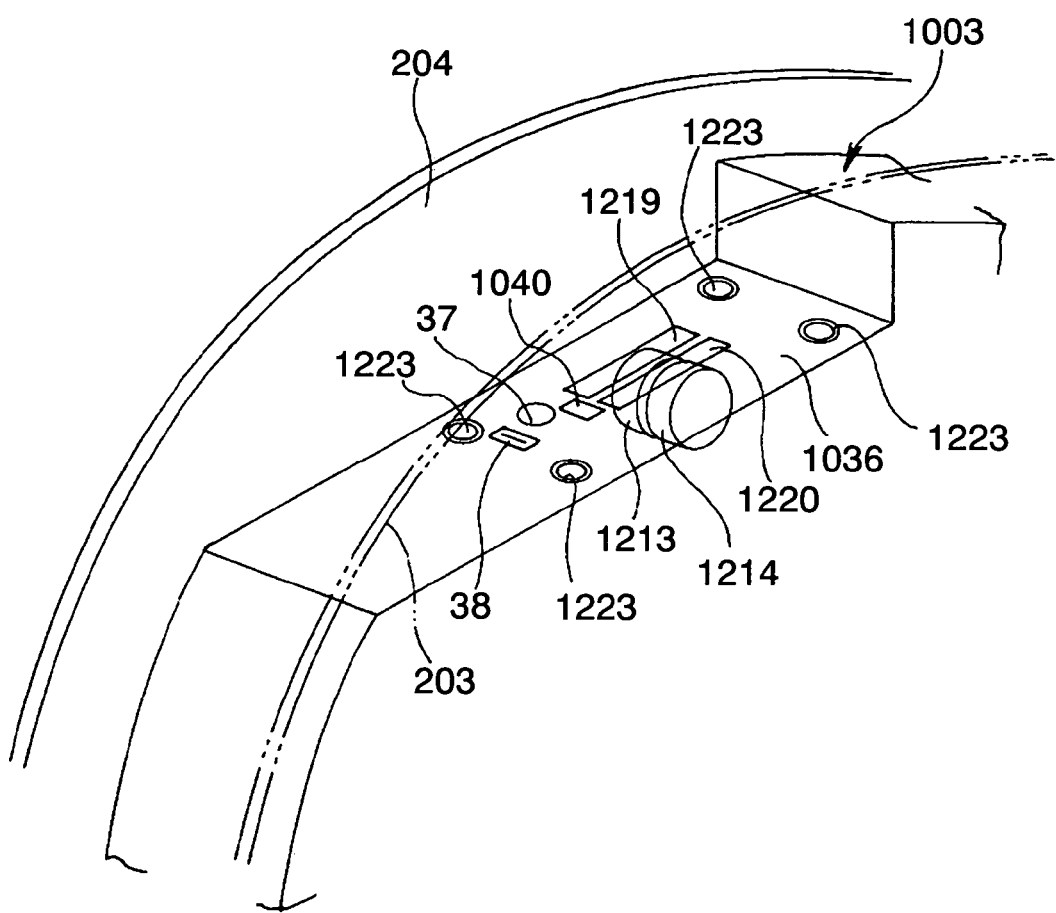
FIG. 63 is a perspective view of the connector installation section, according to the fourth embodiment of the present invention.
Figure 64:
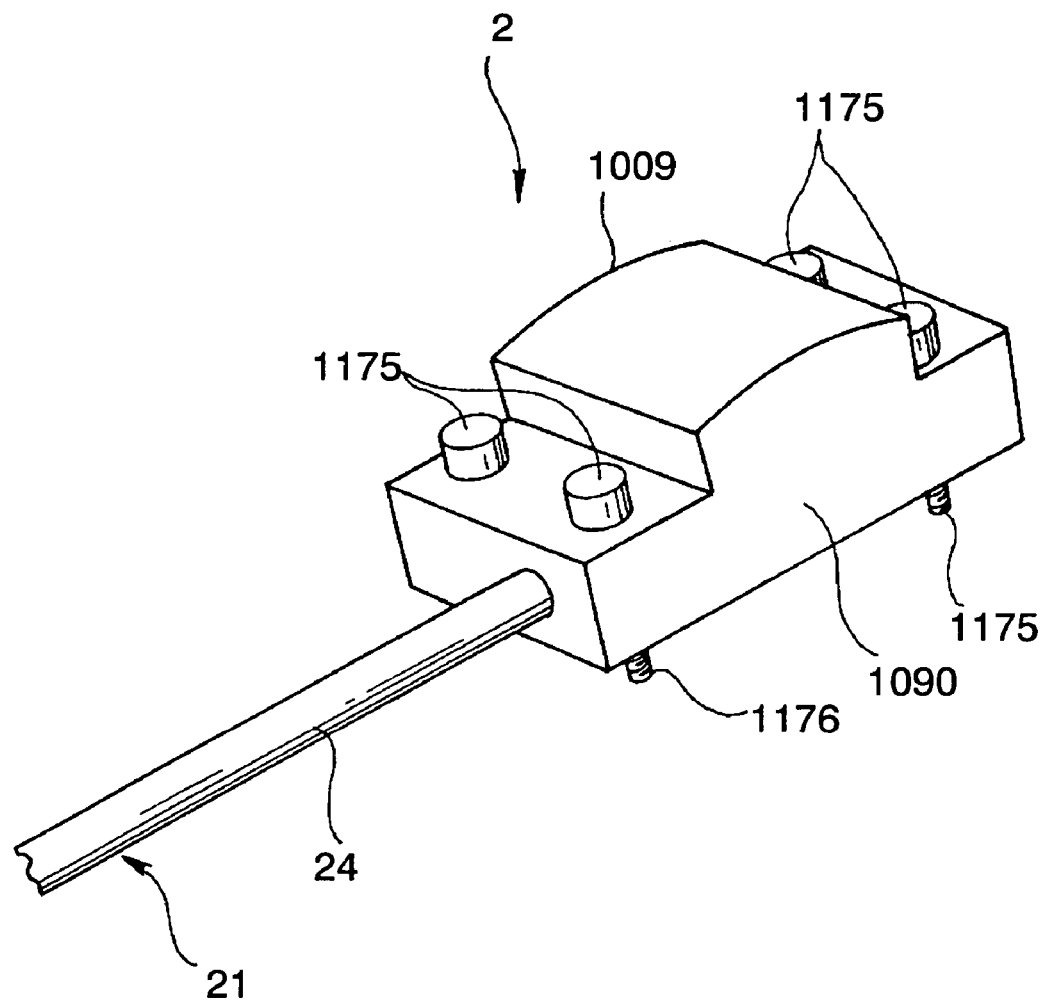
FIG. 64 is a perspective view of the connector section, according to the fourth embodiment of the present invention.
Figure 65:
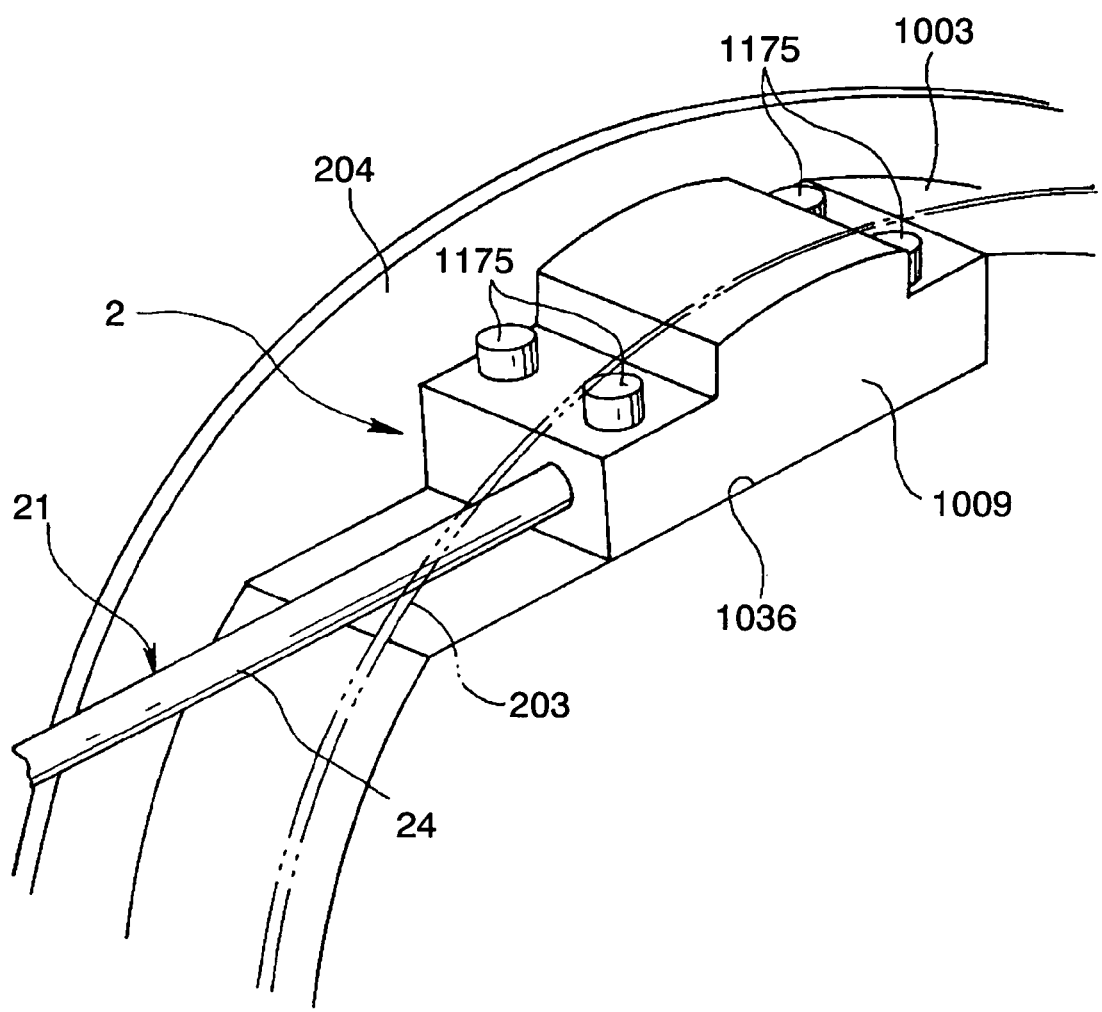
FIG. 65 is a perspective view in a state where the connector section is installed in the connector installation section, according to the fourth embodiment of the present invention.

FIG. 57 through FIG. 65 are diagrams associated with a fourth embodiment of the present invention. FIG. 57 is a cross-sectional diagram of a drum section. FIG. 58 is an enlarged cross-sectional diagram through line G-G of FIG. 57. FIG. 59 is an enlarged diagram of a drive unit and a pulling apparatus. FIG. 60 is a partially enlarged diagram of the main parts of a connector section. FIG. 61 is a partially enlarged diagram of the main parts of a connector installation section. FIG. 62 is a partially enlarged diagram of the main parts in a state in which the connector section is installed in the connector installation section. FIG. 63 is a perspective view of the connector installation section. FIG. 64 is a perspective view of the connector section. FIG. 65 is a perspective view in a state where the connector section is installed in the connector installation section.

Here, the same symbols are used for structures with the same operations and effects as in the above-described first embodiment, and the descriptions are omitted.

(Construction)

In an endoscope apparatus 1001 of the fourth embodiment, an electric bending circuit section 1035 housed in an internal cavity of a drum section 1003 as shown in FIG. 57 controls the drive of motor units 1211 and 1212 of a drive unit 1034 as shown in FIG. 58, serving as an electric bending apparatus, and bends the bending section 23 in a desired direction, based on real time rotary position information of potentiometers 1151 and 1152 as shown in FIG. 58, and a remote control instruction signal transmitted from the joystick 62 of the remote controller 6.

Here, default rotary position information of the potentiometers 1151 and 1152 at the maximum bending angle is stored in the electric bending circuit section 1035. That is, pulley sections 1153 and 1154 described later can be rotated at will up to these values. Although the values of the defaults cannot be permanently changed, it is possible to amend them to desired values using a personal computer connected to a personal computer connector provided in the endoscope apparatus 1001, which is not shown in the figure.

Next is a description of the drive unit 1034 and the pulling apparatus 1091.

Firstly, the pulling apparatus 1091 will be described.

As shown in FIG. 57, a connector section 1009 formed as a housing made of metal or resin is connected to the base end section of the insertion section 21, and the pulling apparatus 1091 is located in this connector section 1009.

Here, since the drive unit 1034 and the pulling apparatus 1091 bend in both the vertical direction and the horizontal direction, these are a type in which two similar mechanisms are used as a pair. However, in this description, the vertical direction is used as the main example, and since the horizontal direction is similar, its description is omitted to a certain degree.

As shown in FIG. 58 and FIG. 59, pulley sections 1153 and 1154, onto which the pulling apparatus side wires 141, 142, etc. connected to the insertion section side wires 135, 136, 137 and 138 (refer to FIG. 11) are wound, are provided in the pulling apparatus 1091. Pulley side roller sections 1155 and 1156 are provided on one surface of the pulley sections 1153 and 1154 respectively. The pulley side roller sections 1155 and 1156 have pulley side elastic tires 1157 and 1158 formed from an elastic material such as urethane, rubber or the like, which form their circumference sections. The pulley side roller sections 1155 and 1156 make contact with motor side elastic tires 1215 and 1216 of the motor side roller sections 1213 and 1214 via the pulley side elastic tires 1157 and 1158.

The pulley side roller sections 1155 and 1156 are arranged such that they protrude by a distance a from the connector side apertures 1159 and 1160 of the connector section 1009 as shown in FIG. 60.

Furthermore, the pulley side elastic tires 1157 and 1158 shown in FIG. 58 contact potentiometer side elastic tires 1163 (only the pulley side elastic tire 1157 is shown in the figure) of potentiometer side roller sections 1161 (only the pulley side elastic tire 1157 is shown in the figure), as well as the motor side elastic tires 1215 and 1216. The potentiometer side roller sections 1161 are provided on the rotating shafts of the potentiometers 1151 and 1152 shown in FIG. 58.

The potentiometer side roller sections 1161 shown in FIG. 59 rotate with the rotation of the pulley side elastic tires 1157 and 1158 shown in FIG. 58.

Each of the potentiometers 1151 and 1152 shown in FIG. 58 has first and second terminals representing the upper limit and lower limit of the values of its resistance, and a third terminal representing the value of resistance corresponding to the rotary position. The three terminals are connected to the male potentiometer connector 1166 which protrudes from a connector installation section 1036 of the connector section 1009, via a cable 1165 as shown in FIG. 59.

Furthermore, as shown in FIG. 59, on the back of the connector installation section 1036 are provided a cable 1041 and a female potentiometer connector 1040, which are connected to the male potentiometer connector 1166 and transmit the information from the three terminals to an electric bending circuit section 1035.

Here, the potentiometers 1151 and 1152 may be single turn type or multiple turn type rotary detecting potentiometers, and a three turn or five turn type is used in the present embodiment.

Next is a description of the drive unit 1034. As shown in FIG. 58, the drive unit 1034 is provided with motor units 1211 and 1212 as drive sources.

The two motor units 1211 and 1212 are installed so as to manage the bending directions of the bending section 23. That is, the motor unit 1211 is for the vertical bending direction, and the motor unit 1212 is for the horizontal bending direction.

Motor side roller sections 1213 and 1214 are provided on the rotating output shafts 1217 and 1218 of the motor units 1211 and 1212. The motor side roller sections 1213 and 1214 make close contact with the pulley side elastic tires 1157 and 1158 respectively due to a pressure mechanism as described later. The motor side roller sections 1213 and 1214 rotate the pulley side roller sections 1155 and 1156 in synchronization with the output shafts 1217 and 1218 respectively. Here, the motor side roller sections 1213 and 1214 are also covered with motor side elastic tires 1215 and 1216 formed from the same elastic material as the pulley side elastic tires 1157 and 1158. Drum side apertures 1219 and 1220 are formed in locations corresponding to the motor side elastic tires 1215 and 1216 of the connector installation section 1036 of the tubular member 201.

Here, as shown in FIG. 61, the motor side roller sections 1213 and 1214 are arranged such that they stand away from the drum side apertures 1219 and 1220 provided in the connector installation section 1036 by a distance β.

As show in FIG. 58, the motor units 1211 and 1212 have positive terminals and negative terminals, and cables 1230 are connected to the electric bending circuit section 1035.

The motor units 1211 and 1212 comprise motor sections 1221, being drive sources for generating driving forces, and reduction gear sections 1222 formed by gear trains such as spur gears, planetary gears, or the like, which transmit the driving forces from the motor sections 1221.

Here, the pulley sections 1153 and 1154 are connected together and fixed to the case 1090 of the connector section 1009 via a shaft 1171 and a fixing plate 1172.

Spacers 1173 and 1174 are provided on the shaft 1171 between the pulley sections 1153 and 1154 and the fixing plate 1172 so as to rotate easily.

Next is a description of the pressure mechanism.

As shown in FIG. 63, four threaded holes 1223 are provided in the connector installation section 1036. As shown in FIG. 64, the connector section 1009 similarly has four fixing knobs 1175 having male screws corresponding to the threaded holes 1223.

A pressure mechanism is formed by the threaded holes 1223 and the fixing knobs 1175.

Here, as shown in FIG. 62, in the state where the connector section 1009 is in close contact with the connector installation section 1036, the locations of the above-described distances α and β are arranged such that the motor side elastic tires 1215 and 1216 and the pulley side elastic tires 1157 and 1158 are deformed elastically by a distance γ to hold them together under pressure.

Using such a construction, the endoscope 2 is provided in the elongated insertion section 22, with a bending section 23 that can be bent at will.

The bending control wires 131, 132, 133 and 134 are arranged such that they protrude from the bending section 23.

The drive unit 1034 has drive sources (motor units 1211 and 1212) for generating driving forces, and is a drive section that can be attached to and removed from the endoscope 2 at will.

The pulling apparatus 1091 pulls the bending control wires 131, 132, 133 and 134 by the driving forces applied, and is a pulling section for bending the bending section 23.

The pulley side roller sections 1155 and 1156 are provided in the drive unit 1034, and are pulling apparatus side transmission devices for transmitting the driving forces from the drive sources.

The motor side roller sections 1213 and 1214 are provided on the drive unit and the pulling apparatus 1091, make contact with the pulley side roller sections 1155 and 1156 respectively, and are drive unit side transmission devices for transmitting the driving forces from the motor units 1211 and 1212.

The threaded holes 1223 and the fixing knobs 1175 form the pressure mechanism for applying pressure to the contact between the drive unit side and the pulling apparatus side transmission devices, and are fixing devices for fixing the pulling apparatus 1091 to the drive unit 1034.

The pulley side roller sections 1155 and 1156 are second rotors provided in the pulling apparatus 1091.

The motor side roller sections 1213 and 1214 are first rotors provided in the drive unit 1034.

Pressure contact parts are provided in the contact areas of the pulley side elastic tires 1157 and 1158 of the pulley side roller sections 1155 and 1156, and the motor side elastic tires 1215 and 1216 of the motor side roller sections 1213 and 1214, for holding them under pressure by the pressure mechanism.

(Operation of the Invention)

Hereunder is a description of the operation of the endoscope apparatus 1001 of the fourth embodiment.

This is normally used in a state where the connector section 1009 is connected to the drum section 1003.

The operation of the endoscope apparatus 1001 when it is set up in this state will be described.

Firstly, the lid 82 of the storage case 8 is opened, the cover panel 55 is opened, and the drum section 1003 is rotated until its connector installation section 1036 can be observed from above. Then, the industrial endoscope 2 to be used is fitted to the connector installation section 1036 of the drum section 1003.

At this time, the light guide connector 112 of the connector section 1009 shown in FIG. 57 and FIG. 59 is fitted in the light guide connector receiving section 37 on the drum section 1003 side as shown in FIG. 63.

Next, the male image connector 119 and the male potentiometer connector 1166 on the connector section 9 as shown in FIG. 57 are plugged into the female image connector 38 on the drum section 1003 side as shown in FIG. 63.

Then, the male screw sections 1176 as shown in FIG. 64 make contact with the threaded holes 1223 of the connector installation section 1036 as shown in FIG. 63. Thus, the connector section 1009 is fastened onto the connector installation section 1036 by turning the fixing knobs 183 and 184. In this manner, the connector section 1009 is installed in the connector installation section 1036.

At this time, the following operations occur in the drive unit 1034 and the pulling apparatus 1091 shown in FIG. 57 through FIG. 59.

As shown in FIG. 60 and FIG. 61, the pulley side roller sections 1155 and 1156 (refer to FIG. 58) protrude by a distance α, and the motor side roller sections 1213 and 1214 (refer to FIG. 58) by a distance β. When the connector section 1009 is assembled on the connector installation section 1036 by the above-described operations, the pulley side roller sections 1155 and 1156, and the motor side roller sections 1213 and 1214 are held together under pressure by a distance γ as shown in FIG. 62. This distance γ is absorbed by the pulley side elastic tires 1157 and 1158, and the motor side elastic tires 1215 and 1216 formed from elastic material, being deformed elastically. That is, close contact between the two is maintained without fail by their mutual elasticity.

In this manner, assembly of the connector section 1009 onto the connector installation section 1036 is complete.

Then, similarly to the first embodiment, by closing the cover panel 55 such that the insertion section 21 is sandwiched by the rubber pieces 53 and 54, the apparatus is now ready for use.

Next is a description of the bending operation during use. The driving operation will be described for the drive unit 1034, being an electric bending apparatus, by control by the remote controller 6.

By manipulating the joystick 62 of the remote controller 6 in a desired vertical or horizontal direction, a signal corresponding to the tilt angle of this joystick 62 is transmitted to the electric bending circuit section 1035 shown in FIG. 58 and FIG. 59. Then, in this electric bending circuit section 1035, the rotation of the motor side roller sections 1213 and 1214 corresponding to the control signal is calculated mathematically, and rotation instruction signals corresponding to the calculated result are transmitted to the motor units 1211 and 1212.

The motor sections 1221 of the motor units 1211 and 1212 rotate according to the rotation instruction signals transmitted from the electric bending circuit section 1035. The rotations of the motor sections 1221 are transmitted to the output shafts 1217 and 1218 via the reduction gear section 1222, and the output shafts 1217 and 1218 rotate. Then, the motor side roller sections 1213 and 1214 rotate as the output shafts 213 and 214 rotate.

At this time, since the pulley side elastic tires 1157 and 1158 of the pulley side roller sections 1155 and 1156, and the motor side elastic tires 215 and 216, are held together under pressure, the pulley side roller sections 1155 and 1156 rotate in synchronization with the rotation of the motor side roller sections 1213 and 1214. Here, potentiometer side roller sections 1161 are provided in the pulley side roller sections 1155 and 1156 such that the pulley side elastic tires 1157 and 1158, and the potentiometer side elastic tires 1163 make contact. Therefore, the potentiometer side roller sections 1161 rotate in synchronization with the rotation of the pulley side roller sections 1155 and 1156, and signals according to the rotary positions are transmitted from the potentiometers 1151 and 1152 to the male potentiometer connector 1166.

That is, the rotations of the output shafts 1217 and 1218 are detected by the potentiometers 1151 and 1152.

That is, the motor sections 1221 operate in a state where the rotary positions of the output shafts 1217 and 1218 are always monitored by the potentiometers 1151 and 1152. Accordingly, the electric bending circuit section 1035 controls such that the operations of the motor sections 1221 are stopped at the point where the calculated values match the rotary positions of the output shafts 1217 and 1218 detected by the potentiometers 1151 and 1152.

Accordingly, when the joystick 62 is manipulated, the bending section 23 is bent as described above, and the tip section body 22 is pointed in a desired direction at the time of examination so that an object can be observed.

Since there is a case where the bending section 23 is bent at a maximum bending angle as required, multiple turn type potentiometers are used as the potentiometers 1151 and 1152. Especially, in the case where the diameter of the potentiometer side roller sections 1161 is smaller than the diameter of the pulley side roller sections 1155 and 1156, since the rotation of the potentiometer side roller sections 1161 increases, a multiple turn type is suitable.

In the case where any of the bending control wires 131, 132, 133 and 134 is pulled by a large amount, such as when the bending section 23 is bent at its maximum bending angle, the motor sections 1211 and 1212 rotate the output shafts 1217 and 1218, in other words the pulley side roller sections 1155 and 1156, by a large rotation angle under the control of the electric bending circuit section 1035, and wind the appropriate bending control wires 131, 132, 133 and 134. At this time, since the potentiometers 1151 and 1152 of the present embodiment are three turn type or five turn type, they rotate a maximum of one and a half revolutions or two and a half revolutions in each direction.

The bending operations performed as the pulley sections 153 and 154 rotate are the same as in the first embodiment.

(Effects)

As described above, the drive unit 1034 and the pulling apparatus 1091 are separated, and industrial endoscopes 2 can be attached to and removed from the drum section 1003 interchangeably; thus it is possible to select a suitable endoscope to use for an examination. In addition, when the drive unit 1034 and the pulling apparatus 1091 are assembled, since the motor side elastic tires 1215 and 1216, and the pulley side elastic tires 1157 and 1158, are held together under pressure, there is no slippage between the drive unit 1034 and the pulling apparatus 1091. Furthermore, in the case where a driving force is transmitted from the drive unit 1034, which can be attached to and removed from the endoscope 2, to the pulling apparatus 1091 to bend the bending section 23 of the endoscope 2, the loss of driving force is reduced, and the driving force is transmitted stably; thus it is possible to increase the stability and accuracy of the bending operation of the bending section 23.

Furthermore, since the drive unit 1034 and the pulling apparatus 1091 are not fastened together by engaged gears, it is possible to dock them together without providing ferrules in both of them.

Here, the combinations of male and female screws are not limited to those used in the first through fourth embodiments and their modified examples; instead the males and females may be reversed.

Moreover, in the first through the fourth embodiments and their modified examples, the bending control wires 131, 132, 133 and 134 are divided into the insertion section side wires 135, 136, 137 and 138, and the pulling apparatus side wires 141, 142, etc. However, the insertion section side wires 135, 136, 137 and 138 may be wound onto the pulley sections directly.

Furthermore, in the fourth embodiment, the elastic tires need not be provided on both the drive unit side and the pulling apparatus side, but may be provided on one side, and the state of being held together under pressure due to elastic deformation may be ensured by that part.

The preferred embodiments of the present invention are described above. However, the present invention is not limited to the embodiments. Changes to the combination of the structures in each embodiment, addition of structures, omission, replacement, and other modifications, are possible. The present invention is not limited by the aforementioned description, but limited only by the scope of the appended claims.

What is claimed is:

1. An endoscope apparatus comprising:
   an endoscope in which a bending section capable of being bent is provided in an elongated insertion section thereof;
   control wires stretching out of said bending section;
   a drive unit, which has a drive source that generates a driving force, and is removably attached to said endoscope;
   a pulling apparatus, which is provided in said endoscope for performing bending operations of said bending section by pulling said control wires using said driving force applied;
   an installation device for installing said pulling apparatus in said drive unit; and
   a transmission device, which is installed in said drive unit and said pulling apparatus so as to be attached and removed at will, separate from said installation device, for transmitting said driving force from said drive source to said pulling apparatus;
   wherein said drive unit has a male component, said pulling apparatus has a female component, said transmission device is a connecting member which connects said male component and said female component, and said connecting member is a cylindrical body which is inserted inside said female component, and is externally fitted to said male component.

2. An endoscope apparatus according to claim 1, wherein said male component is an output shaft of a motor being said drive unit.

3. An endoscope apparatus according to claim 1, wherein said female component is a rotation member which is wound with one of said control wires.

4. An endoscope apparatus according to claim 3, wherein said rotation member is a pulley having a slot section on an outer periphery around which said control wire is wound.

5. An endoscope apparatus according to claim 3, wherein said rotation member is a sprocket around which a chain connected to said control wire is wound.

6. An endoscope apparatus according to claim 3, wherein said control wires include an insertion section side control wire arranged inside said insertion section, and a pulling apparatus side control wire which is connected to said insertion section side control wire inside said pulling apparatus, and said rotation member is wound with said pulling apparatus side control wire.

7. An endoscope apparatus according to claim 1, having a vertical direction bending control wire as one of said control wires and a horizontal direction bending control wire as another one of said control wires, having two female components around which is wound each of said vertical direction bending control wire and said horizontal direction bending control wire, as said female components, and having two male components combined with said two female components, as said male components.

8. An endoscope apparatus comprising:

an apparatus body;

an endoscope in which a bending section capable of being bent is provided in an elongated insertion section thereof, and a connector section is provided on a base end of said insertion section;

control wires stretching out of said bending section;

a drive unit, which is installed in said apparatus body, has a drive source that generates a driving force, and is removably attached to said connector section;

a pulling apparatus, which is installed in said connector section, for performing bending operations of said bending section by pulling said control wires using said driving force applied;

an installation device for installing said connector section in said apparatus body; and a transmission device, which is installed in said drive unit and said pulling apparatus so as to be attached and removed at will, separate from said installation device, for transmitting said driving force from said drive source to said pulling apparatus, wherein said drive unit has a male component, said pulling apparatus has a female component, said transmission device is a connecting member which connects said male component and said female component, and said connecting member is a cylindrical body which is inserted inside said female component, and is externally fitted to said male component.

9. An endoscope apparatus according to claim 8, wherein said male component is an output shaft of a motor being said drive unit.

10. An endoscope apparatus according to claim 8, wherein said female component is a rotation member which is wound with one of said control wires.

11. An endoscope apparatus according to claim 10, wherein said rotation member is a pulley having a slot section on an outer periphery around which one of said control wires is wound.

12. An endoscope apparatus according to claim 10, wherein said rotation member is a sprocket around which a chain connected to one of said control wires is wound.

13. An endoscope apparatus according to claim 10, wherein said control wires include an insertion section side control wire arranged inside said insertion section, and a pulling apparatus side control wire which is connected to said insertion section side control wire inside said pulling apparatus, and said rotation member is wound with said pulling apparatus side control wire.

14. An endoscope apparatus according to claim 8, having a vertical direction bending control wire as one of said control wires and a horizontal direction bending control wire as another one of said control wires, having two female components around which is wound each of said vertical direction bending control wire and said horizontal direction bending control wire, as said female components, and having two male components combined with said two female components, as said male components.

15. An endoscope apparatus according to claim 8, wherein said installation device comprises a screw section.

16. An endoscope apparatus according to claim 15, wherein a male threaded section is provided on said connector section and a female threaded section is provided on said apparatus body, as said screw section.

17. An endoscope apparatus according to claim 8, wherein said installation device comprises an engaging section.

18. An endoscope apparatus according to claim 17, wherein a protruding section is provided on said connector section and a recessed section is provided on said apparatus body side, as said engaging section.

19. An endoscope apparatus according to claim 18, wherein engagement with said engaging section is by a snap fit.

20. An endoscope apparatus according to claim 8, wherein said apparatus body has a drum section which winds said insertion section, and said drive unit is installed in said drum section.

21. An endoscope apparatus comprising:

an apparatus body;

an endoscope in which a bending section capable of being bent is provided in an elongated insertion section thereof, and a connector section is provided on a base end of said insertion section;

control wires stretching out of said bending section;

a drum section, which is installed in said apparatus body, for winding said insertion section;

a drive unit, which is installed in said drum section, has a drive source that generates a driving force, and is removably attached to said connector section;

a pulling apparatus, which is installed in said connector section, for performing bending operations of said bending section by pulling said control wires using said driving force applied;

an installation device for installing said connector section in said drum section; and at least one pair of a drive unit side transmission device and a pulling apparatus side transmission device respectively provided on a drive unit side and a pulling apparatus side, which are contacted with each other for transmitting a driving force from said drive source, wherein said drive unit side transmission device and said pulling apparatus side transmission device comprise at least a first rotation member provided on said drive unit and a second rotation member provided on said pulling apparatus, a first rotation member side elastic tire is provided on the first rotation member, a second rotation member side elastic tire is provided on the second rotation member, and a pressure contact part is provided in a contact area of the first rotation member side elastic tire and the second rotation member side elastic tire.

* * * * *